US012379717B2

(12) United States Patent
Frackowiak et al.

(10) Patent No.: US 12,379,717 B2
(45) Date of Patent: Aug. 5, 2025

(54) SYSTEMS AND METHODS FOR MONITORING AND CONTROLLING INDUSTRIAL PROCESSES

(71) Applicant: Industrial Video Solutions Inc., Fairfax, VA (US)

(72) Inventors: Slawek Frackowiak, Fairfax, VA (US); Leszek Frackowiak, Vienna, VA (US)

(73) Assignee: Industrial Video Solutions Inc., Fairfax, VA (US)

( * ) Notice: Subject to any disclaimer, the term of this patent is extended or adjusted under 35 U.S.C. 154(b) by 0 days.

(21) Appl. No.: 18/600,258

(22) Filed: Mar. 8, 2024

(65) Prior Publication Data
US 2024/0255932 A1 Aug. 1, 2024

Related U.S. Application Data

(63) Continuation-in-part of application No. 18/431,571, filed on Feb. 2, 2024, now Pat. No. 12,130,249, which
(Continued)

(51) Int. Cl.
*G01N 25/56* (2006.01)
*G05B 19/418* (2006.01)

(52) U.S. Cl.
CPC .......... *G05B 19/41875* (2013.01); *G05B 2219/32368* (2013.01)

(58) Field of Classification Search
CPC ............. G05B 19/41875; G05B 2219/32368
See application file for complete search history.

(56) References Cited

U.S. PATENT DOCUMENTS 1,338,094 A * 4/1920 Pope .................... D21F 7/04
  162/360.2
4,988,875 A * 1/1991 Ortiz ................... G01N 21/952
  250/559.46
(Continued)

FOREIGN PATENT DOCUMENTS

JP  08-022320    1/1996
JP  2006-099497  4/2006
(Continued)

OTHER PUBLICATIONS

International Search Report, dated Nov. 21, 2023, from corresponding International Application No. PCT/US2023/029385.
(Continued)

*Primary Examiner* — Aaron W Carter
(74) *Attorney, Agent, or Firm* — Thomas | Horstemeyer, LLP

(57) ABSTRACT

Aspects of the present invention provide methods, systems, and/or the like for: (1) determining temperature data for at least part of an article of manufacture in a manufacturing process; (2) analyzing the temperature data to identify a first portion of the article of manufacture having a temperature that deviates from a surrounding portion of the first portion, the first portion comprising: at least one hot spot, at least one hot streak, at least one cold spot, or at least one cold streak on the article of manufacture; (3) determining, for the first portion of the article of manufacture, a set of properties related to the temperature: (4) processing the set of properties using at least one of a rules-based model, a machine-learning model, or a classification model to produce a defect classification; and (5) providing an indication of the defect classification for display on a computing device.

19 Claims, 27 Drawing Sheets

Related U.S. Application Data is a continuation-in-part of application No. 18/212,548, filed on Jun. 21, 2023, now Pat. No. 11,932,991, which is a continuation-in-part of application No. 18/131,926, filed on Apr. 7, 2023, now Pat. No. 11,846,930.

(60) Provisional application No. 63/470,057, filed on May 31, 2023, provisional application No. 63/394,805, filed on Aug. 3, 2022.

(56) References Cited

U.S. PATENT DOCUMENTS

| | | | |
|---|---|---|---|
| 5,006,722 A * | 4/1991 | Adelson | G01N 21/8851 715/810 |
| 5,233,415 A | 8/1993 | French et al. | |
| 5,389,789 A | 2/1995 | Nguyen | |
| 5,862,608 A | 1/1999 | Kotitschke | |
| 5,942,689 A | 8/1999 | Bonissone et al. | |
| 5,999,636 A | 12/1999 | Juang | |
| 6,075,590 A * | 6/2000 | Edgar | H04N 1/4097 250/341.8 |
| 6,135,000 A | 10/2000 | Caspar et al. | |
| 6,158,287 A | 12/2000 | Satake et al. | |
| 6,299,730 B1 * | 10/2001 | Broek | B65H 26/02 356/429 |
| 6,362,889 B1 | 3/2002 | Mustonen | |
| 6,388,749 B1 | 5/2002 | Yamashita et al. | |
| 6,410,916 B1 | 6/2002 | Jost et al. | |
| 6,463,170 B1 | 10/2002 | Toivonen et al. | |
| 6,466,877 B1 | 10/2002 | Chen et al. | |
| 6,498,993 B1 | 12/2002 | Chen et al. | |
| 6,519,534 B2 | 2/2003 | Chen et al. | |
| 6,522,978 B1 | 2/2003 | Chen et al. | |
| 6,542,852 B2 | 4/2003 | Chen et al. | |
| 6,615,511 B2 | 9/2003 | Augscheller et al. | |
| 6,849,851 B2 | 2/2005 | Komulainen et al. | |
| 6,943,913 B1 | 9/2005 | Jung | |
| 7,138,036 B2 | 11/2006 | Yamashita et al. | |
| 7,494,567 B2 | 2/2009 | Haran | |
| 7,688,079 B2 | 3/2010 | Shioda et al. | |
| 7,750,330 B2 | 7/2010 | Murata | |
| 7,934,722 B2 | 5/2011 | Namikawa | |
| 8,023,843 B2 | 9/2011 | Degruchy et al. | |
| 8,265,498 B2 | 9/2012 | Fan et al. | |
| 8,396,384 B2 | 3/2013 | Hayashihara et al. | |
| 8,477,234 B2 | 7/2013 | Tanigawa et al. | |
| 8,494,384 B2 | 7/2013 | Furuya et al. | |
| 9,401,015 B2 * | 7/2016 | Minekawa | G06F 18/24 |
| 9,838,635 B2 | 12/2017 | Gousev et al. | |
| 10,552,662 B2 | 2/2020 | Chang et al. | |
| 10,591,285 B2 | 3/2020 | Ando | |
| 10,875,024 B2 | 12/2020 | Li et al. | |
| 10,884,401 B2 | 1/2021 | Valkonen | |
| 10,946,675 B2 | 3/2021 | Takeishi | |
| 11,142,422 B2 | 10/2021 | Paanasalo | |
| 11,231,363 B2 | 1/2022 | Shitara | |
| 11,297,388 B2 | 4/2022 | Menendez | |
| 11,816,893 B1 * | 11/2023 | Frackowiak | G06T 7/0004 |
| 11,846,930 B1 * | 12/2023 | Frackowiak | G06T 7/11 |
| 11,932,991 B2 * | 3/2024 | Frackowiak | G06V 10/776 |
| 2002/0023369 A1 * | 2/2002 | Augscheller | D21F 7/04 34/459 |
| 2002/0052699 A1 * | 5/2002 | Chen | G06F 18/21 702/34 |
| 2002/0066545 A1 | 6/2002 | Karjanmaa | |
| 2002/0166970 A1 * | 11/2002 | Komulainen | G01N 33/346 250/340 |
| 2004/0112560 A1 * | 6/2004 | Yamashita | D21F 7/04 162/263 |
| 2004/0218795 A1 * | 11/2004 | Zhou | G06T 7/73 382/129 |
| 2005/0079386 A1 | 4/2005 | Brown et al. | |
| 2005/0094160 A1 | 5/2005 | Murai et al. | |
| 2005/0167620 A1 * | 8/2005 | Cho | G01N 21/95 250/559.45 |
| 2005/0169509 A1 | 8/2005 | Grasslin et al. | |
| 2006/0082763 A1 * | 4/2006 | Teh | G01N 21/9501 356/237.2 |
| 2006/0096726 A1 | 5/2006 | Ahvenainen et al. | |
| 2006/0102839 A1 * | 5/2006 | Bhaskar | G06T 7/0004 250/310 |
| 2006/0143671 A1 | 6/2006 | Ens et al. | |
| 2006/0196621 A1 | 9/2006 | Johansson | |
| 2006/0258246 A1 | 11/2006 | Bomberger et al. | |
| 2007/0058089 A1 | 3/2007 | Wang | |
| 2007/0137823 A1 * | 6/2007 | Haran | G01N 21/3554 250/339.04 |
| 2007/0200568 A1 * | 8/2007 | Shioda | G01N 22/04 324/643 |
| 2007/0294284 A1 * | 12/2007 | Evans | H04L 41/22 707/999.102 |
| 2008/0311416 A1 | 12/2008 | Kelly et al. | |
| 2009/0028416 A1 * | 1/2009 | Floeder | G01N 21/89 382/141 |
| 2009/0028417 A1 * | 1/2009 | Floeder | G06T 7/0004 235/494 |
| 2009/0030544 A1 * | 1/2009 | Floeder | G01N 21/8851 700/122 |
| 2009/0060316 A1 * | 3/2009 | Ruuska | B65H 26/025 382/141 |
| 2013/0120561 A1 * | 5/2013 | Heintze | G01N 25/72 348/135 |
| 2013/0255096 A1 | 10/2013 | Kampris et al. | |
| 2014/0098360 A1 | 4/2014 | Kwon | |
| 2014/0286563 A1 * | 9/2014 | Frackowiak | G06T 7/001 382/141 |
| 2015/0013556 A1 | 1/2015 | Slaats | |
| 2016/0267111 A1 | 9/2016 | Shoaib et al. | |
| 2017/0015832 A1 | 1/2017 | Berlin et al. | |
| 2018/0347970 A1 * | 12/2018 | Sasaki | G01B 11/2513 |
| 2018/0348146 A1 * | 12/2018 | Ando | G01N 21/55 |
| 2019/0129396 A1 * | 5/2019 | Valkonen | G05B 19/41875 |
| 2019/0139212 A1 * | 5/2019 | Hanzawa | G06N 3/08 |
| 2020/0130976 A1 * | 4/2020 | Paanasalo | B65H 26/025 |
| 2020/0184630 A1 * | 6/2020 | Wang | G01N 25/72 |
| 2021/0010954 A1 * | 1/2021 | Adler | G06F 18/214 |
| 2021/0011177 A1 * | 1/2021 | Adler | G01N 23/083 |
| 2021/0025687 A1 | 1/2021 | Ichikawa | |
| 2021/0209745 A1 | 7/2021 | Jiang et al. | |
| 2021/0287354 A1 * | 9/2021 | Kumar | G06T 7/10 |
| 2021/0380364 A1 | 12/2021 | Gumpinger et al. | |
| 2022/0020139 A1 | 1/2022 | Weiss et al. | |
| 2022/0076411 A1 | 3/2022 | Georgescu et al. | |
| 2022/0236176 A1 | 7/2022 | Bolton et al. | |
| 2022/0270229 A1 * | 8/2022 | Nokelby | G06V 30/224 |
| 2023/0074247 A1 * | 3/2023 | Xia | G01R 31/2801 |
| 2023/0137432 A1 * | 5/2023 | Selim | G06N 3/08 706/12 |
| 2023/0147668 A1 * | 5/2023 | Penugonda | G06F 11/0772 714/38.1 |
| 2023/0169642 A1 * | 6/2023 | Floeder | G06T 7/001 382/103 |
| 2023/0237640 A1 * | 7/2023 | Ekawa | G06V 10/87 382/141 |
| 2023/0260413 A1 * | 8/2023 | Lee | G06F 3/0482 434/262 |
| 2023/0286261 A1 | 9/2023 | Condello et al. | |
| 2023/0342907 A1 * | 10/2023 | Katsuyama | G06T 7/0004 |
| 2023/0401589 A1 * | 12/2023 | Panchamgam | G06Q 30/0201 |
| 2024/0044079 A1 * | 2/2024 | Frackowiak | D21G 9/0054 |
| 2024/0046443 A1 * | 2/2024 | Okazaki | G06T 7/0004 |
| 2024/0046617 A1 * | 2/2024 | Adolf | G06T 7/0004 |
| 2024/0071059 A1 * | 2/2024 | Schreiner | G06F 18/217 |
| 2024/0094139 A1 * | 3/2024 | Smith | G01N 21/8914 |
| 2024/0102242 A1 * | 3/2024 | Ramu | D21G 9/0009 |
| 2024/0175831 A1 * | 5/2024 | Frackowiak | G01N 25/56 |
| 2024/0212356 A1 * | 6/2024 | Frackowiak | G06V 10/776 |

(56) References Cited

U.S. PATENT DOCUMENTS

2024/0255932 A1* 8/2024 Frackowiak ............ D21F 7/003
2024/0361756 A1* 10/2024 Frackowiak ......... D21G 9/0054

FOREIGN PATENT DOCUMENTS

| KR | 10-2021-0002142 | 1/2021 |
| KR | 10-2021-0150834 | 12/2021 |
| WO | 2017/037896 | 3/2017 |
| WO | 2022-043024 | 3/2022 |

OTHER PUBLICATIONS

International Search Report, dated Nov. 23, 2023, from corresponding International Application No. PCT/US2023/029389.
Notice of Allowance, dated Aug. 22, 2023, from corresponding U.S. Appl. No. 18/131,920.
Notice of Allowance, dated Nov. 24, 2023, from corresponding U.S. Appl. No. 18/212,548.
Notice of Allowance, dated Oct. 25, 2023, from corresponding U.S. Appl. No. 18/131,926.
Office Action, dated Jul. 13, 2023, from corresponding U.S. Appl. No. 18/131,926.
Office Action, dated Sep. 20, 2023, from corresponding U.S. Appl. No. 18/212,548.
Written Opinion of the International Searching Authority, dated Nov. 21, 2023, from corresponding International Application No. PCT/US2023/029385.
Written Opinion of the International Searching Authority, dated Nov. 23, 2023, from corresponding International Application No. PCT/US2023/029389.
Office Action, dated Apr. 22, 2024, from corresponding U.S. Appl. No. 18/431,571.
Office Action, dated May 30, 2024, from corresponding U.S. Appl. No. 18/600,272.
Notice of Allowance, dated Jun. 26, 2024, from corresponding U.S. Appl. No. 18/431,571.
Notice of Allowance, dated Sep. 19, 2024, from corresponding U.S. Appl. No. 18/600,272.
Notice of Allowance, dated Oct. 11, 2024, from corresponding U.S. Appl. No. 18/767,569.

* cited by examiner

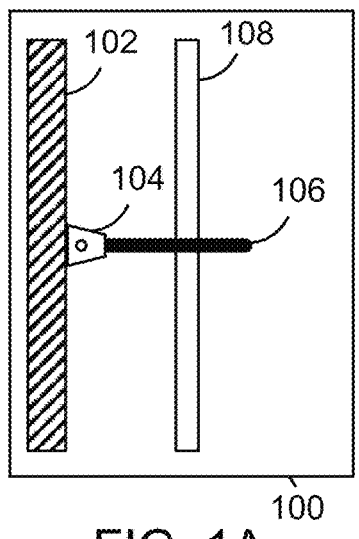 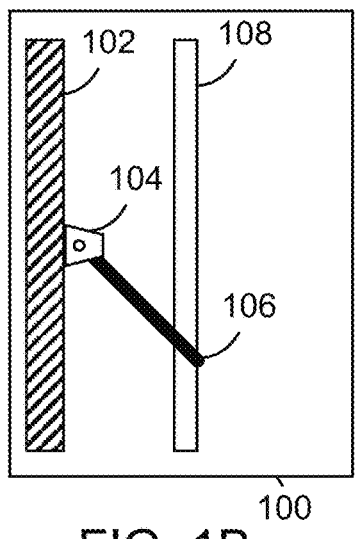 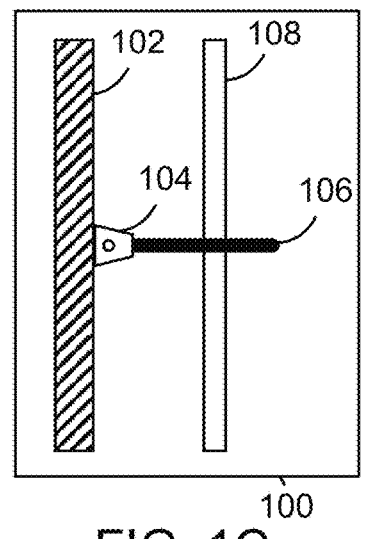
FIG. 1A    FIG. 1B    FIG. 1C
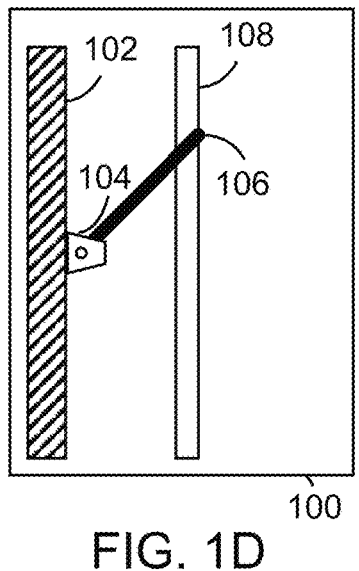 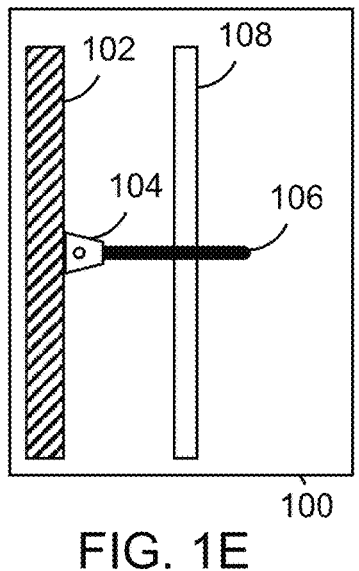 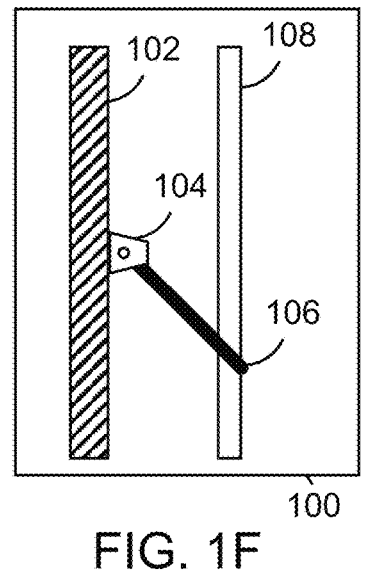
FIG. 1D    FIG. 1E    FIG. 1F

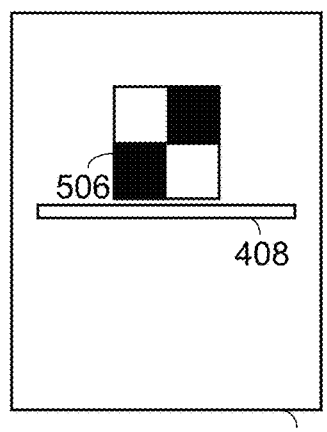 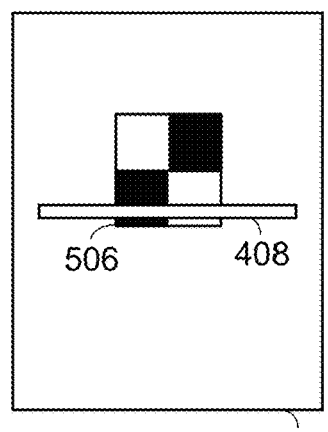
FIG. 5A   FIG. 5B
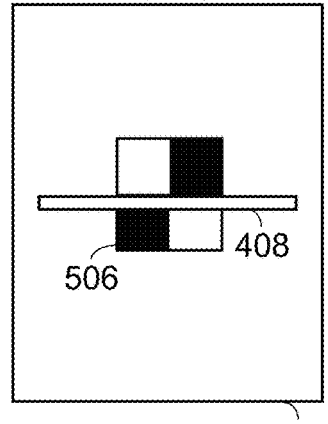 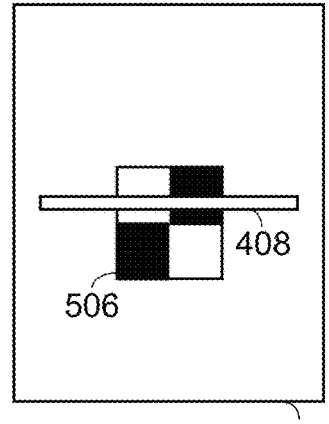
FIG. 5C   FIG. 5D
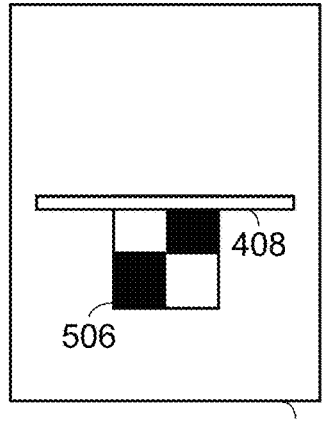 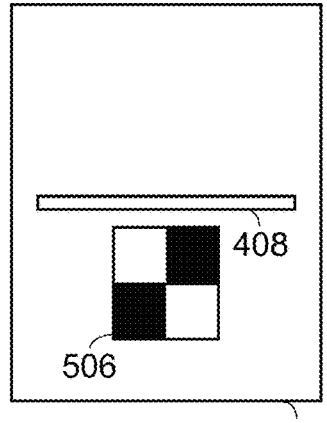
FIG. 5E   FIG. 5F
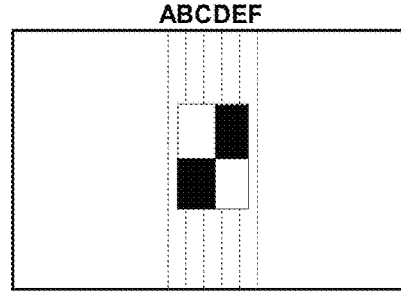
FIG. 5G

SYSTEMS AND METHODS FOR MONITORING AND CONTROLLING INDUSTRIAL PROCESSES

CROSS-REFERENCE TO RELATED APPLICATIONS

This application is a continuation-in-part of U.S. patent application Ser. No. 18/431,571, filed Feb. 2, 2024, which is a continuation-in-part of U.S. patent application Ser. No. 18/212,548, filed Jun. 21, 2023, which claims the benefit of U.S. Provisional Patent Application Ser. No. 63/470,057 filed May 31, 2023, and is also a continuation-in-part of U.S. patent application Ser. No. 18/131,926, filed Apr. 7, 2023, now U.S. Pat. No. 11,846,930, issued Dec. 19, 2023, which claims the benefit of U.S. Provisional Patent Application Ser. No. 63/394,805, filed Aug. 3, 2022. The disclosures of all of the above patents and patent applications are hereby incorporated herein by reference in their entirety.

TECHNICAL FIELD

The present disclosure is generally related to data processing systems and methods for the automated analysis of media or recognition of a pattern for the purpose of monitoring and/or controlling industrial processes and/or components thereof.

BACKGROUND

Industrial processes, such as processes used in manufacturing items (e.g., food, consumer goods, chemicals, etc.), often include complex manufacturing equipment, assembly equipment, fabrication equipment, and/or the like operating with tight tolerances. In addition, such equipment may also operate at high speed, such as for mass-produced items. In many cases, entities, such as manufacturers, who are performing these industrial processes will implement still image surveillance equipment to monitor the equipment used within these industrial processes and/or items produced by these industrial processes that can prove to present technical challenges in identifying and remedying malfunctioning of the equipment and/or damaging of items during performance of the industrial processes. For example, a food manufacturer may perform quality assurance checks of completed food packages by using an automated camera and image processing system to identify malformed or damaged items. However, although such a system may be able to detect large problems in individual items, still images generated by these systems often fail to reveal variations over time in the items (e.g., variations in the properties of the items), thus preventing diagnosis and remediation of manufacturing process issues and/or item issues.

In other cases, entities may use closed-circuit television systems to monitor equipment used in the industrial processes and/or items produced by these industrial processes for the purpose of detecting malfunctioning equipment and/or damaging of items. However, these closed-circuit television systems also present technical challenges in that the real-time surveillance provided through these systems may fail to reveal gradual variations over time in a manufacturing process, or minor variations in rapid processes. For example, an arm of a machine may sporadically shift over time, such that an observer (e.g., a human) watching a video produced in real-time through a closed-circuit television system may find it very difficult to notice variations in movement. In another example, a component of a manufacturing process may move with a certain frequency such that a frame rate produced by a real-time surveillance system that is too slow and/or alias with the frequency may prevent an observer from detecting abnormal component movement.

In addition to monitoring, entities, such as manufacturers, who are performing these industrial processes may also implement control systems for measuring properties of equipment components and/or items being manufactured during performance of the industrial processes for the purpose of using the measurements of the properties in controlling the equipment. Again, these control systems can present technical challenges in that the control systems can often operate at too slow of a rate to timely correct processing parameters of the equipment, leading to the manufacturing of defective items at a large quantity.

For example, equipment used in manufacturing paper may include a set of actuators that feeds pulp to the equipment. In addition, the equipment may also include one or more steam boxes to reduce the paper moisture by increasing the sheet temperature. Here, an entity operating the equipment may use a quality control system (QCS) to control the actuators and/or steam boxes to ensure uniform distribution (profiles) of several properties that define the specification of a given paper grade for the paper manufactured by the equipment. The equipment may include multiple scanners that use different scanner configurations to measure properties important to the process at given locations.

However, a scanner can often take ten to thirty seconds to provide a full width profile for a measured property. As a result, the QCS may receive the measurements of the properties (e.g., the full width profiles) at too slow of a rate that can result in manufacturing of defective paper at a significant quantity due to delayed control adjustments made to the actuators and/or steam boxes. Accordingly, there is a need for systems and methods that aid in timely identification of deviations from baseline movements of components of equipment and/or items produced through manufacturing and other industrial processes.

SUMMARY

In general, various embodiments of the present disclosure provide methods, apparatuses, systems, computing devices, computing entities, and/or the like for monitoring and/or controlling one or more processing parameters for an industrial process. In accordance with various embodiments, a method is provided that comprises: receiving, by computing hardware, media of a processing region of an industrial process, wherein: the processing region comprises at least one object, the media comprises a plurality of media elements, and each media element of the plurality of media elements comprises a field of view of the at least one object; identifying, by the computing hardware and based on an area of interest, a set of pixels, wherein the field of view comprises the area of interest; for each media element of the plurality of media elements: extracting, by the computing hardware, an attribute value from each pixel of the set of pixels found in the media element; and constructing, by the computing hardware, a respective array comprising each attribute value; combining, by the computing hardware, each of the respective arrays in a data structure; and analyzing, by the computing hardware, the data structure to provide data on a processing parameter associated with the industrial process.

In particular embodiments, analyzing the data structure comprises facilitating generation and transmission of a graphical representation of the data structure to a user device for display. In particular embodiments, the respective arrays are indexed in the data structure according to a sequence of the plurality of media elements found in the media, and the graphical representation comprises a visual representation displaying each respective array being arranged at least substantially sequentially along an axis of the graphical representation according to how the respective arrays are indexed in the data structure.

In particular embodiments, the media comprises an interstitial portion, and the method further comprises: determining, by the computing hardware, a beginning media element of the interstitial portion; determining, by the computing hardware, an ending media element of the interstitial portion; and excluding, by the computing hardware, media elements between the beginning media element and the ending media element from the plurality of media elements. In some embodiments, determining the beginning media element of the interstitial portion comprises receiving a first trigger signal indicating an ending of a movement cycle of the at least one object; and determining the ending media element of the interstitial portion comprises receiving a second trigger signal indicating a beginning of the movement cycle of the at least one object. In some embodiments, determining the beginning media element of the interstitial portion comprises detecting a first change in the attribute value for a particular pixel of the set of pixels; and determining the ending media element of the interstitial portion comprises detecting a second change in the attribute value for the particular pixel of the set of pixels. In some embodiments, the second change corresponds to the beginning media element of a processing portion, the first change corresponds to the ending media element of the processing portion, and the method further comprises: determining, by the computing hardware, an elapsed time of the processing portion; removing, by the computing hardware, media elements of the plurality of media elements based at least in part on the elapsed time being greater than a baseline processing time; and adding, by the computing hardware, media elements to the plurality of media elements based at least in part on the elapsed time being less than the baseline processing time.

In accordance with various embodiments, a system is provided comprising a non-transitory computer-readable medium storing instructions and a processing device communicatively coupled to the non-transitory computer-readable medium. The processing device is configured to execute the instructions and thereby perform operations comprising: receiving media of a processing region involving processing of an object, wherein: the media comprises a plurality of media elements, and each media element of the plurality of media elements comprises a field of view of the object; identifying, based on an area of interest, a set of pixels, wherein the field of view comprises the area of interest; for each media element of the plurality of media elements: extracting an attribute value for the object from the set of pixels found in the media element; and constructing a respective array comprising each attribute value; combining each of the arrays into a data structure; and analyzing the data structure to provide data on a property of the object.

In particular embodiments, the media is received at least substantially in real time from recording equipment, and the operations further comprise: receiving a speed measurement indicating a speed at which the object is being processed; and adjusting a frame rate of the recording equipment based on a difference between the speed measurement and a baseline speed. In particular embodiments, the operations further comprise: retrieving a template data structure representing a baseline attribute value; generating a difference data structure by subtracting the data structure from the template data structure; and facilitating transmission of a graphical representation of the difference data structure to a user device for display.

In particular embodiments, the operations further comprise: retrieving a template data structure representing baseline attribute value; generating a difference data structure by subtracting the data structure from the template data structure; and modifying an industrial process associated with processing the object based on determining that an aspect of the difference data structure satisfies a threshold. In some embodiments, modifying the industrial process comprises at least one of: facilitating discarding production of the object; or facilitating adjustment of a processing parameter of the industrial process.

In particular embodiments, the operations further comprise: identifying a location of the object in each of a plurality of arrays; constructing a dataset comprising the locations and corresponding times; and determining a frequency of movement of the object by performing a Fourier transform on the dataset. In particular embodiments, the system further comprises at least one motion sensor communicatively coupled to the processing device, and the operations further comprise: determining a beginning media element of an interstitial portion based on a first trigger signal from the at least one motion sensor, the first trigger signal indicating an end of a movement cycle of the object; determining an ending media element of the interstitial portion based on a second trigger signal from the at least one motion sensor, the second trigger signal indicating a beginning of the movement cycle of the object; and excluding media elements between the beginning media element and the ending media element from the plurality of media elements.

In accordance with various embodiments, a non-transitory computer-readable medium storing computer-executable instructions is provided. The computer-executable instructions, when executed by computing hardware, configure the computing hardware to perform operations comprising: receiving media of an industrial process, wherein: the media comprises a plurality of media elements, and each media element of the plurality of media elements comprises a field of view of at least one object; identifying a set of pixels within the field of view; for each media element of the plurality of media elements: extracting an attribute value for the at least one object from the set of pixels found in the media element; and constructing a respective array comprising each attribute value; combining each of the arrays into a data structure; and analyzing the data structure to provide data on a processing parameter associated with the at least one object.

In particular embodiments, the at least one object comprises at least one of a component of equipment or an item being manufactured. In particular embodiments, analyzing the data structure comprises facilitating generation and transmission of a graphical representation of the data structure to a user device for display. In particular embodiments, the respective arrays are indexed in the data structure according to a sequence of the plurality of media elements found in the media, and the graphical representation comprises a visual representation displaying each respective array being arranged at least substantially sequentially along an axis of the graphical representation according to how the respective arrays are indexed in the data structure.

In particular embodiments, the operations further comprise: retrieving a template data structure representing baseline attribute value; generating a difference data structure by subtracting the data structure from the template data structure; and modifying the industrial process based on determining that an aspect of the difference data structure satisfies a threshold. In some embodiments, modifying the industrial process comprises at least one of: facilitating discarding production of the at least one object; or facilitating adjustment of the processing parameter of the industrial process.

In accordance with various embodiments, a method is provided that comprises: receiving, by computing hardware, media of a processing region of an industrial process, wherein: the processing region comprises at least one object, the media comprises a plurality of media elements, and each media element of the plurality of media elements comprises a field of view of the at least one object; identifying, by the computing hardware and based on an area of interest, a set of pixels, wherein the field of view comprises the area of interest; and for each media element of the plurality of media elements: extracting, by the computing hardware, an attribute value from each pixel of the set of pixels found in the media element; constructing, by the computing hardware, an attribute profile comprising the attribute value for each pixel of the set of pixels; mapping, by the computing hardware, the attribute profile to a mapped profile, wherein the mapped profile comprises at least one property value that correlates to at least one attribute value of the attribute profile; and providing, by the computing hardware, the mapped profile to a control system, wherein the control system uses the mapped profile in controlling one or more processing parameters of the industrial process.

In particular embodiments, the at least one object comprises at least one of a component of equipment or an item being manufactured. In some embodiments, the industrial process comprises a manufacturing process for paper, the at least one attribute value comprises a measure of brightness of at least one pixel of the set of pixels, the at least one property value comprises a measure of a thickness of the paper, and the one or more processing parameters comprise an amount of pulp fed by one or more actuators during the manufacturing of the paper. In some embodiments, the industrial process comprises a manufacturing process for paper, the at least one attribute value comprises a measure of temperature of at least one pixel of the set of pixels, the at least one property value comprises a measure of moisture of the paper, and the one or more processing parameters comprise an amount of steam provided by one or more steam boxes to a surface of the paper during the manufacturing of the paper.

In particular embodiments, the method further comprises: averaging, by the computing hardware, the at least one attribute value found in the attribute profile constructed for each media element of the plurality of media elements in a time domain to produce an average attribute value; and analyzing, by the computing hardware, the average attribute value to determine a variation in the one or more processing parameters of the industrial process. In some embodiments, the method further comprises providing data on the variation to personnel to use in identifying a problem with equipment performing the industrial process.

In particular embodiments, mapping the attribute profile to the mapped profile comprises using a rules-based model to map the at least one attribute value to the at least one property value, and the rules-based model uses at least one of a table, graph, or rules sets in identifying the at least one property value. In particular embodiments, the method further comprises: identify, by the computing hardware, a correlation strength that identifies how well the at least one attribute value correlates to the at least one property value; and providing, by the computing hardware, the correlation strength along with the mapped profile to the control system, wherein the control system determines, based on the correlation strength, to use the mapped profile in controlling the one or more processing parameters of the industrial process.

In accordance with various embodiments, a system is provided comprising a non-transitory computer-readable medium storing instructions and a processing device communicatively coupled to the non-transitory computer-readable medium. The processing device is configured to execute the instructions and thereby perform operations comprising: receiving a media element of a processing region of an industrial process, wherein: the processing region comprises at least one object, and the media element comprises a field of view of the at least one object; identifying, based on an area of interest, a set of pixels, wherein the field of view comprises the area of interest; and extracting an attribute value from each pixel of the set of pixels found in the media element; constructing an attribute profile comprising the attribute value for each pixel of the set of pixels; and mapping the attribute profile to a mapped profile, wherein the mapped profile comprises at least one property value that correlates to at least one attribute value of the attribute profile, and the at least one property value is used by a control system in controlling one or more processing parameters of the industrial process.

In some embodiments, the industrial process comprises a manufacturing process for paper, the at least one attribute value comprises a measure of brightness of at least one pixel of the set of pixels, the at least one property value comprises a measure of a thickness of the paper, and the one or more processing parameters comprise an amount of pulp fed by one or more actuators during the manufacturing of the paper. In some embodiments, the industrial process comprises a manufacturing process for paper, the at least one attribute value comprises a measure of temperature of at least one pixel of the set of pixels, the at least one property value comprises a measure of moisture of the paper, and the one or more processing parameters comprise an amount of steam provided by one or more steam boxes to a surface of the paper during the manufacturing of the paper.

In particular embodiments, the operations further comprise providing the mapped profile to the control system to use the mapped profile in controlling the one or more processing parameters of the industrial process. In particular embodiments, mapping the attribute profile to the mapped profile comprises using a rules-based model to map the at least one attribute value to the at least one property value. In particular embodiments, the operations further comprise: identify a correlation strength that identifies how well the at least one attribute value correlates to the at least one property value; and providing the correlation strength along with the mapped profile to the control system, wherein the control system determines, based on the correlation strength, to use the mapped profile in controlling the one or more processing parameters of the industrial process.

In accordance with various embodiments, a non-transitory computer-readable medium storing computer-executable instructions is provided. The computer-executable instructions, when executed by computing hardware, configure the computing hardware to perform operations comprising: receiving a media element of a processing region of an industrial process, wherein: the processing region comprises at least one object, and the media element comprises a field of view of the at least one object; identifying, based on an area of interest, a set of pixels, wherein the field of view comprises the area of interest; extracting an attribute value from each pixel of the set of pixels found in the media element; and mapping at least one attribute value for at least one pixel of the set of pixels to a mapped profile, wherein the mapped profile comprises at least one property value that correlates to the at least one attribute value, and the at least one property value is used by a control system in controlling one or more processing parameters of the industrial process.

In some embodiments, the industrial process comprises a manufacturing process for paper, the at least one attribute value comprises a measure of brightness of at least one pixel of the set of pixels, the at least one property value comprises a measure of a thickness of the paper, and the one or more processing parameters comprise an amount of pulp fed by one or more actuators during the manufacturing of the paper. In some embodiments, the industrial process comprises a manufacturing process for paper, the at least one attribute value comprises a measure of temperature of at least one pixel of the set of pixels, the at least one property value comprises a measure of moisture of the paper, and the one or more processing parameters comprise an amount of steam provided by one or more steam boxes to a surface of the paper during the manufacturing of the paper.

In particular embodiments, the operations further comprise providing the mapped profile to the control system to use the mapped profile in controlling the one or more processing parameters of the industrial process. In particular embodiments, mapping the at least one attribute value to the mapped profile comprises using a rules-based model to map the at least one attribute value to the at least one property value. In particular embodiments, the operations further comprise: identifying a correlation strength that identifies how well the at least one attribute value correlates to the at least one property value; and providing the correlation strength along with the mapped profile to the control system, wherein the control system determines, based on the correlation strength, to use the mapped profile in controlling the one or more processing parameters of the industrial process.

A computer-implemented data processing method for improving prediction and automated, active prevention of paper break on a paper manufacturing line, in various aspects, comprises: (1) receiving, by computing hardware, current thermal imaging data for a portion of a paper web in the paper manufacturing process; (2) determining, by the computing hardware, force data for the portion of the paper web; (3) accessing, by the computing hardware, paper profile data for the paper manufacturing line; (4) processing, by the computing hardware to produce a first data analysis result, current thermal imaging data, the force data, and the paper profile data using a machine-learning model trained with respective historical thermal imaging data, respective historical force data, and respective paper profile data for each respective prior paper breakage event in a set of prior paper breakage events; (5) generating, by the computing hardware based on the first data analysis result, a prediction as to an occurrence of the paper break on the portion of the paper web; (6) identifying, by the computing hardware, a preventative action based on the prediction; and (7) facilitating, by the computing hardware, performance of the preventative action. In some aspects, the preventative action comprises at least one of: modifying an operating parameter of at least one machine component used in the paper manufacturing line; activating a cleaning component for the paper manufacturing line; or (8) at least temporality ceasing production of paper on the paper manufacturing line.

In some aspects, the method further comprises: (1) determining, by the computing hardware, a paper break result indicating whether the paper break occurred subsequent to the performance of the preventative action; and (2) transmitting, by the computing hardware, the paper break result, the preventative action, the current thermal imaging data, and the force data to an external computing system as additional training data for the machine-learning model. In various aspects, the current thermal imaging data identifies a current moisture profile of the paper web. In some aspects, the preventive action further comprises at least one of activating a siren or generating an alert and transmitting the alert to a computing device. In particular aspects, the method comprises: (1) identifying, by the computing hardware, a component of the paper manufacturing process that is a predicted cause of the occurrence of the paper break; (2) identifying, by the computing hardware, a manufacturer of the component; and (3) transmitting, by the computing hardware, data associated with the prediction to a computing system associated with the manufacturer of the component. In various aspects, the method further comprises: (1) receiving, by the computing hardware from the computing system associated with the manufacturer, one or more modified operating parameters for the component; and (2) facilitating, by the computing hardware, implementation of the one or more modified operating parameters for the component.

In particular aspects, identifying the preventative action based on the prediction comprises processing the prediction using a second machine-learning model trained with respective preventive action success data for each respective prior paper breakage predictions in a set of prior paper breakage predictions. In some aspects the respective historical thermal imaging data indicates paper weak spot properties for each respective prior paper breakage event in the set of prior paper breakage events. On other aspects, the respective historical force data indicates paper web process frequency data or paper web amplitude data for each respective paper web during each respective prior paper breakage event in a set of prior paper breakage events. In particular aspects, the machine learning model comprises an artificial neural network using the paper weak spot properties for each respective prior paper breakage and the paper web process frequency data or paper web amplitude data a set of inputs to establish a set of causation relationships between the set of inputs and the set of prior paper breakage events.

A system, in some aspects, comprises: (1) a non-transitory computer-readable medium storing instructions; and (2) a processing device communicatively coupled to the non-transitory computer-readable medium. In various aspects, processing device is configured to execute the instructions and thereby perform operations comprising: (1) determining moisture data for a portion of a paper web in a paper manufacturing line; (2) determining force data for the portion of the paper web; (3) accessing paper profile data for the paper manufacturing line; (4) accessing historical paper breakage event data; (5) processing the moisture data, the force data, the paper profile data, and the historical paper breakage event data using at least one of a rules-based model or a machine-learning model to generate a prediction of an occurrence of a paper break on the portion of the paper web; and (6) responsive to the prediction of the occurrence of the paper break, facilitating performance of a preventative action. In some aspects, the preventative action comprises at least one of: (A) modifying an operating parameter of at least one machine component used in the paper manufacturing line; (B) activating a cleaning component for the paper manufacturing line; (C) activating a siren; (D) generating an alert and transmitting the alert to a computing device; and/or (E) at least temporality ceasing production of paper on the paper manufacturing line.

In some aspects, the operations further comprise processing the prediction and historical preventative action success data using at least one of a rules-based model or a machine-learning model to select the preventative action. In other aspects, the operations further comprise: (1) identifying a component on the paper manufacturing line identified by the prediction; (2) identifying a manufacturer of the component; and (3) transmitting data associated with the prediction to a computing system associated with the manufacturer of the component.

In particular aspects, the operations further comprise: (1) receiving from the computing system associated with the manufacturer, one or more modified operating parameters for the component; and (2) facilitating implementation of the one or more modified operating parameters for the component on the paper manufacturing line.

In a particular aspect, the preventative action comprises activating the cleaning component for the paper manufacturing line. In such aspects, activating the cleaning component may comprise washing one or more felt components on the paper manufacturing line. In some aspects, activating the cleaning component occurs automatically in response to the prediction of the occurrence of the paper break. In various aspects, the operations further comprise: (1) determining whether the prediction of the occurrence of the paper break was derived from the force data or the moisture data or both; and (2) selecting the preventative action based on whether the prediction of the occurrence of the paper break was derived from the force data or the moisture data or both. In various aspects, determining the moisture data comprises deriving the moisture data from one or more thermal images of the paper web.

A non-transitory computer-readable medium, in various embodiments, has program code that is stored thereon, the program code executable by one or more processing devices for performing operations comprising: (1) receiving image data for a portion of a paper web in a paper manufacturing line; (2) determining force data for the portion of the paper web; (3) accessing paper profile data for the paper manufacturing line; (4) accessing historical paper breakage event data, the historical paper breakage event data being derived from a set of historical paper breakage events for a plurality of paper manufacturing lines, wherein the plurality of paper manufacturing lines: (A) each have at least one common piece of machinery as the paper manufacturing line; and (B) produce paper that shares the paper profile data for the paper manufacturing line; (5) processing the image data, the force data, the paper profile data, and the historical paper breakage event data using at least one of a rules-based model, a machine-learning model, or an artificial neural network to generate an output comprising a prediction of an occurrence of a paper break on the portion of the paper web; and (6) responsive to the prediction of the occurrence of the paper break, facilitating performance of a preventative action, wherein the preventative action comprises at least one of: (A) modifying an operating parameter of at least one machine component used in the paper manufacturing line; (B) activating a cleaning component for the paper manufacturing line; (C) activating an alarm; (D) generating an alert and transmitting the alert to a computing device; or (E) at least temporality ceasing production of paper on the paper manufacturing line. In some aspects, processing the image data, the force data, the paper profile data, and the historical paper breakage event data using at least one of the rules-based model, the machine-learning model, or the artificial neural network to generate the prediction of the occurrence of the paper break on the portion of the paper web comprises providing the historical paper breakage event data as a set of inputs to the artificial neural network to establish a causation relationship between the set of inputs and the set of historical paper breakage events, the historical paper breakage event data comprising at least one of paper moisture spot property data during each breakage event in the set of historical paper breakage events, paper web process frequency data during each breakage event in the set of historical paper breakage events, or paper web amplitude data during each breakage event in the set of historical paper breakage events. In some aspects, the rules-based model, the machine-learning model, or the artificial neural network provide predictive breakage outputs that are specific to the at least one common piece of machinery when used to produce paper that shares the paper profile data. In other aspects, the operations further comprise providing the image data and force data as training data to the rules-based model, the machine-learning model, or the artificial neural network.

In various aspects, the operations further comprise: (1) identifying a component on the paper manufacturing line identified by the prediction; (2) identifying a manufacturer of the component; (3) transmitting data associated with the prediction to a computing system associated with the manufacturer of the component; (4) receiving, from the computing system associated with the manufacturer, one or more modified operating parameters for the component; and (5) facilitating implementation of the one or more modified operating parameters for the component on the paper manufacturing line. In particular embodiments, the operations further comprise processing the prediction and historical preventative action success data using at least one of the rules-based model, the machine-learning model, or the artificial neural network to select the preventative action.

BRIEF DESCRIPTION OF THE DRAWINGS

In the course of this description, reference will be made to the accompanying drawings, which are not necessarily drawn to scale, and wherein:

FIGS. 1A-1H provide an example of a representation of an analysis of movement of a component used within an industrial process in accordance with various embodiments of the disclosure;

FIGS. 5A-5G provide another example of a representation of an analysis of a change in a property of an item handled within an industrial process in accordance with various embodiments of the disclosure;

DETAILED DESCRIPTION

Figure 1G:
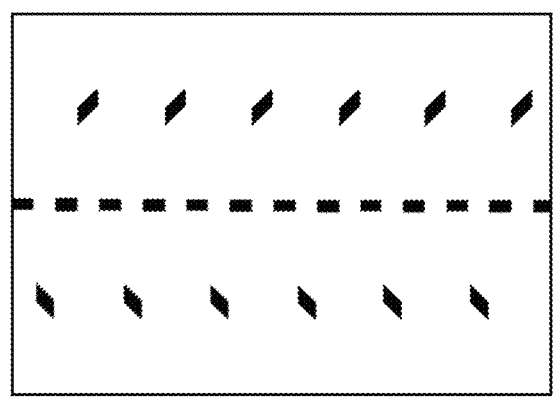

Various embodiments of the disclosure now will be described more fully hereinafter with reference to the accompanying drawings. It should be understood that the disclosure may be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

For the purpose of this disclosure, the term "industrial process" may describe a process by which an item is handled. For example, "handling" an item can involve manufacturing or altering the item such as assembling the item, packaging the item, forming the item, stamping the item, and/or the like. An industrial process may include, for example, a process to handle (e.g., manufacture and/or package) items such as food or drinks. An industrial process may also include handling of non-edible items such as electronics, clothing, furniture, machinery, chemicals, etc. Further still, an industrial process may also include processes to improve items, such as a painting process. An industrial process may be discrete (e.g., producing one unit of an item at a time) or continuous (e.g., producing an item continuously, such as wire, yarn, or chemicals). Thus, in general, an industrial process may include processes by which equipment (e.g., machine(s)) handles items in a substantially repetitive manner.

In industrial processes, equipment components may move in order to handle items, for instance in a periodic manner starting at a beginning position, moving to perform an operation on an item, and returning to a beginning position to reperform the operation on a subsequent item. In some cases, the process may require precise timing and positioning of equipment components in order to produce consistent quality. Rapid mass manufacturing may heighten these requirements, which, if not met, may result in wasted items that do not comply with manufacturing tolerances.

For instance, an industrial process such as a compact disc manufacturing process may include operations to apply a label to a front side of the compact disc with an arm. The arm may move between a starting position to an application position, and back to the starting position in a fraction of a second to maximize production rates. If the arm is misaligned, mistimed, or otherwise falls out of manufacturing tolerances, the arm may cause manufacturing defects such as the labels being applied incorrectly, which can result in a significant portion of manufactured discs being discarded. Similarly, if the compact discs, themselves, become misaligned, then the arm may apply the labels incorrectly, which can also result in a significant portion of manufactured discs being discarded. Likewise, if properties or conditions of the compact discs change so that the surface of the compact discs becomes warped or distorted, then the arm may apply the labels incorrectly, which can result in a significant portion of manufactured discs being discarded.

However, diagnosing the cause of such manufacturing defects can be difficult to perform. For example, diagnosing that the arm is applying labels mid-movement such that precise timing or flexing of the arm during accelerations of the application movement affects proper label placement can be difficult to perform. Further, collecting measurements of certain properties of the arm and/or the disc to allow for adjustments to be made in controlling arm movement in a timely fashion to correct or avoid such manufacturing defects can be difficult to perform.

Accordingly, various embodiments of the present disclosure aid in the diagnostic and/or control process by providing systems and methods for visualizing and analyzing movement of equipment (e.g., machine components) and/or items during an industrial process by extracting focused image data from media such as video, images, and/or the like. For example, FIGS. 1A-1H provide a representation of an analysis of an industrial process that can be performed according to various embodiments of the disclosure. Specifically, various embodiments of the disclosure involve a method that can be performed to record sequential elements of media to capture movement of one or more objects associated with an industrial process as the one or more objects pass through a field of view 100 of the recording equipment. For example, as shown in FIGS. 1A-IF, the method can involve recording sequential elements of media to capture movement of an object such as an arm 106 secured to a wall 102 by a hinge 104 that are part of an industrial process. Here, the method may involve using various types of recording equipment such as, for example, visual cameras such as an area camera recording sequential frames of video, a line scan camera recording sequential line images, and/or the like. In other instances, the method may involve using other types of recording equipment such as, for example, non-visual cameras such as a short-wave infrared camera, a mid-wave infrared camera, a long-wave infrared camera, and/or the like.

In the example shown in FIGS. 1A-IF, the method is used in recording the sequence of media elements demonstrating the arm 106 rotating about the hinge 104. The arm 106 begins in a position that is essentially perpendicular to the wall 102, as shown in FIG. 1A, swings down approximately forty-five degrees, as shown in FIG. 1B, and returns to a position that is essentially perpendicular to the wall 102, as shown in FIG. 1C. Further, the arm 106 continues to swing up approximately forty-five degrees, as shown in FIG. 1D. Subsequently, the arm 106 returns to a position that is essentially perpendicular, as shown in FIG. 1E, to restart the rotation cycle, as shown in FIG. 1F. Thus, the arm 106 in this simplified and exaggerated example rotates up and down about the hinge 104 periodically.

In various embodiments, the method involves recording the arm 106, throughout its movement, as the arm passes through an area of interest 108 that lies within the field of view 100. For example, an operator may indicate the area of interest 108 by making a selection of pixels within the field of view 100 that captures the movement of the arm 106. Accordingly, the area of interest 108 can be composed of various shapes, configurations, sizes, and/or the like. For example, the area of interest 108 shown in FIGS. 1A-IF is represented as a rectangle (e.g., a line of pixels).

In various embodiments, the method involves assembling one or more attribute values (e.g., brightness, color, etc.) gathered from pixels of the media that are found in the area of interest 108 into one or more graphical representations 110 of the movement of the one or more objects. In some embodiments, the method may involve arranging attribute values of the position of the one or more objects as the one or more objects pass through the area of interest. For example, the method may involve assembling media elements (e.g., video frames) of the positions of the arm 106 shown in FIGS. 1A to 1F as the arm 106 passes through the area of interest. In this example, the method may involve assembling a graphical representation, as shown in FIG. 1G, of a repeated pattern of the first set of pixels (e.g., left-most mark) that illustrates the arm 106 shown in the area of interest 108 in FIG. 1A that is essentially in a horizontal position and substantially centered in the area of interest 108.

In some embodiments, the method may involve arranging attribute values of pixels from subsequent frames sequentially in a representation of the periodic movement of the one or more objects as the one or more objects move through the area of interest. For example, the method may involve assembling media elements (e.g., video frames) of the periodic movement of the arm 106 shown in FIGS. 1A to 1F as the arm 106 moves through the area of interest. In this example, the method may involve assembling a graphical representation 110, as shown in FIG. 1G, that illustrates the periodic movement of the arm 106 as a middle mark, a lower mark, a middle mark, an upper mark, a middle mark, and a lower mark, respectively, that correspond to the media elements (e.g., video frames) illustrated in FIGS. 1A, 1B, IC, ID, 1E, and 1F, respectively.

Figure 1H:
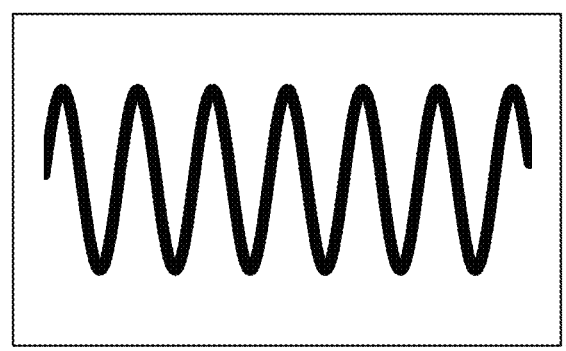
Figure 2A:
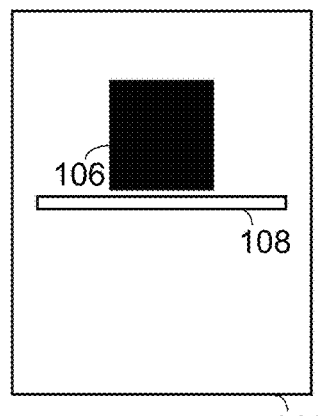
FIGS. 2A-2G provide an example of a representation of an analysis of movement of an item handled within an industrial process in accordance with various embodiments of the disclosure.
Figure 2B:
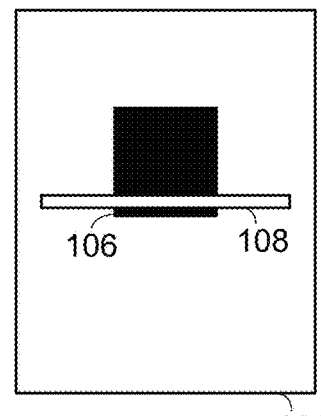
Figure 2C:
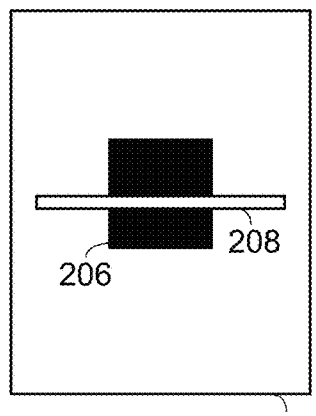
Figure 2D:
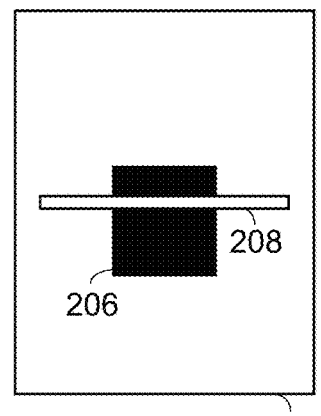
Figure 2E:
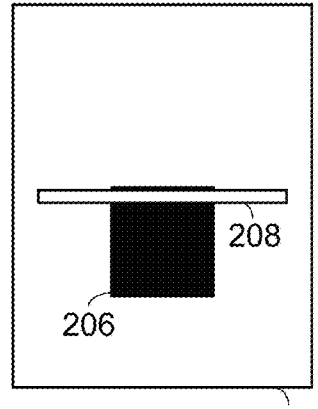
Figure 2F:
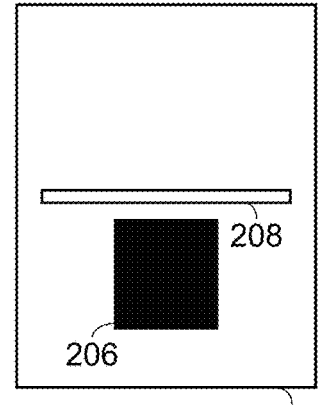
Figure 2G:
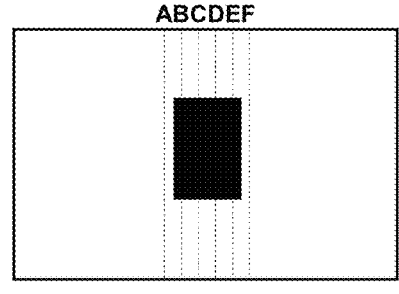

In some embodiments, the method may involve arranging attribute values of pixels from subsequent frames sequentially in a representation of a movement cycle of the one or more objects. For example, the method can involve assembling media elements (e.g., video frames) of the periodic movement of the arm 106 shown in FIGS. 1A to 1F as the arm 106 moves through the area of interest. In this example, the method may involve assembling a graphical representation 110, as shown in FIG. 1H, that illustrates the periodic movement of the arm 106 in a wave motion (e.g., a sine wave motion). Accordingly, the graphical representations shown in FIGS. 1G and 1H can provide the movement, periodic movement, and/or movement cycle of the arm 106, and may appear similar to a graph depicting the position of the arm 106 over time. In some instances, an operator may define multiple areas of interest. In these instances, the method may involve assembling multiple graphical representations of the movement, allowing a comparison of the movement between multiple objects.

Accordingly, an operator may use a graphical representation of the movement of one or more objects in determining problems, errors, defects, and/or the like in the operation (e.g., the movement) of the one or more objects involved in the industrial process. In other instances, an automated process may be performed that uses a graphical representation of the movement of one or more objects in determining problems, errors, defects, and/or the like in the operation of the one or more objects. For example, an operator or automated process may use a graphical representation of the movement of the arm 106 (e.g., pixel arrangements thereof shown in the representation) in determining that the arm 106 does not complete a full movement cycle (e.g., does not fully rotate upward), deviates from a baseline movement frequency (e.g., slower than the baseline movement frequency), jitters during movement (e.g., does not have a smooth movement), and/or the like.

Thus, various embodiments of the disclosure can overcome several technical challenges encountered in using conventional processes to determine errant movements of one or more objects involved in industrial processes. For example, various embodiments of the disclosure can provide a graphical representation of the movement of one or more objects that can facilitate detection of errant movements more quickly over conventional processes such as conventional processes that involve an operator tediously and slowly progressing through a video attempting to compare individual frames in their entirety to detect errant movements. Moreover, various embodiments of the disclosure can provide a graphical representation of the movement of one or more objects that can facilitate detection of errant movements more effectively over conventional processes where the movement of the one or more objects involves an extended movement cycle (e.g., a movement cycle where a thousand frames may lie between a beginning of a cycle and a beginning of the next cycle).

In additional or alternative embodiments, the method can involve carrying out the same analysis with respect to the movement of items being handled (e.g., manufactured) within an industrial process. For example, the process may involve carrying out an analysis to identify a change in movement of items as they are processed through a particular area, part, portion, and/or the like of the industrial process. FIGS. 2A-2G provide an example of a representation of an analysis of a particular item 206 moving through an industrial process according to various embodiments. Here, the method may involve capturing particular movement of the item 206 through the industrial process as the item 206 passes through the area of interest 208 that lies within the field of view 200. FIGS. 2A-2F illustrate sequential elements of media (e.g., sequential frames and/or images) capturing movement of the item 206 as the item 206 moves through a particular area, part, portion, and/or the like of the industrial process.

In some embodiments, the method may involve recording one or more attribute values (e.g., brightness, color, etc.) from pixels in the area of interest 208 and assembling the one or more attribute values into one or more graphical representations of the movement of the item 206. For example, the method may involve assembling the one or more attribute values into the graphical representation 210 shown in FIG. 2G of the movement of the item 206 through the area, part, portion, and/or the like of the industrial process. In additional or alternative embodiments, the method may involve conducting a comparison of graphical representations of the movement of different items 206 to identify a change in the movement of the items 206 as they are processed through the area, part, portion, and/or like of the industrial process.

Figure 3A:
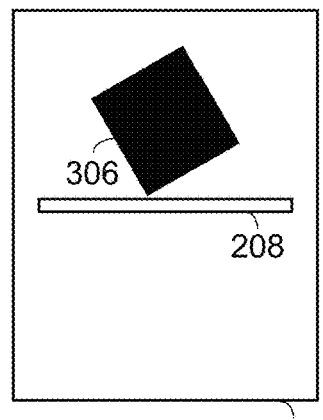
FIGS. 3A-3G provide another example of a representation of an analysis of movement of an item handled within an industrial process in accordance with various embodiments of the disclosure.
Figure 3B:
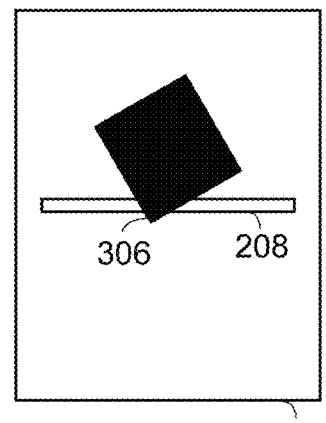
Figure 3C:
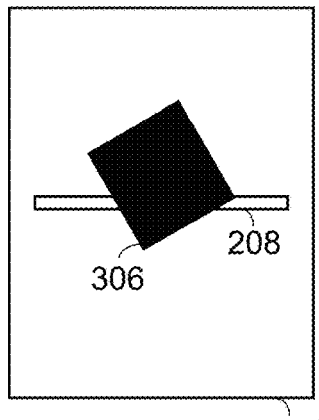
Figure 3D:
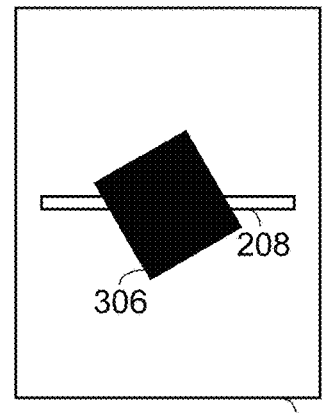
Figure 3E:
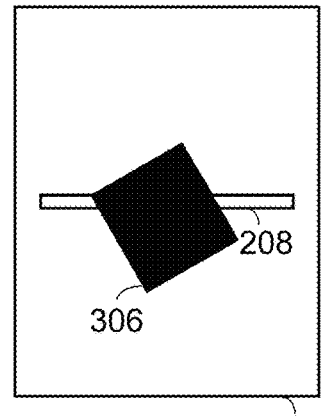
Figure 3F:
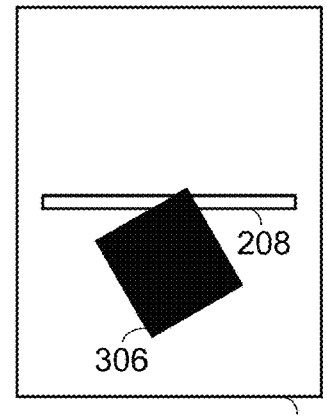
Figure 3G:
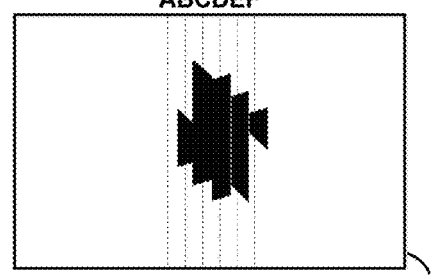

For example, FIGS. 3A-3F illustrate an example of sequential elements of media (e.g., sequential frames and/or images) capturing movement of a second, different item 306 as the second item 306 moves through the particular area, part, portion, and/or the like of the industrial process. Here, movement of the item 306 is captured, as shown in the sequence of media elements of FIGS. 3A-3F, as the item 306 passes through the area of interest 208 that lies within the field of view 200. In this instance, the second item 306 is moving at an angle, as opposed to the first item 206 that moved more in a straight line through the particular area, part, portion, and/or the like of the industrial process. Therefore, the method may involve assembling a graphical representation 310, as shown in FIG. 3G, of the movement of the second, different item 306, and then comparing the graphical representation 210 of the movement of the first item 206 to the graphical representation 310 of the movement of the second item 306 to detect that the movement of the items 206, 306 has changed through the particular area, part, portion, and/or the like of the industrial process.

Thus, various embodiments of the disclosure can be used in monitoring and/or analyzing positioning and/or movement of items in a process such as, for example, monitoring and/or analyzing a location and arrangement of a series of items during manipulation by equipment components. Accordingly, the method can be used in various embodiments to perform such an analysis in helping diagnose item characteristics affecting how an equipment component interacts with the items during manufacture.

Figure 4A:
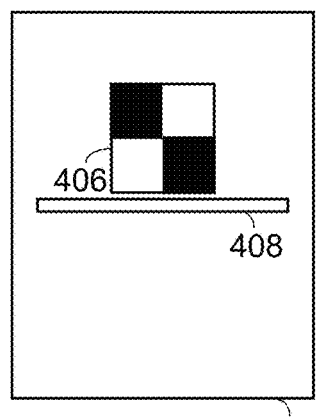
FIGS. 4A-4G provide an example of a representation of an analysis of a change in a property of an item handled within an industrial process in accordance with various embodiments of the disclosure.
Figure 4B:
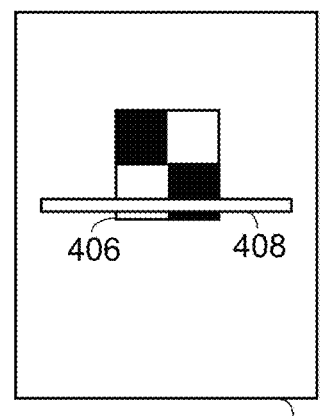
Figure 4C:
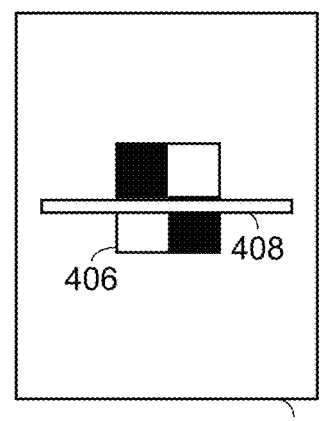
Figure 4D:
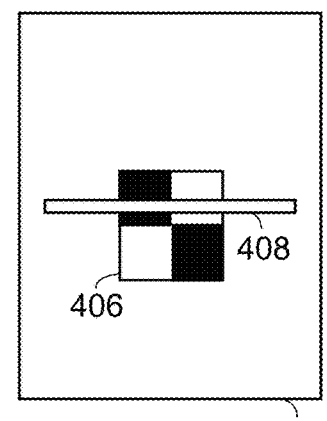
Figure 4E:
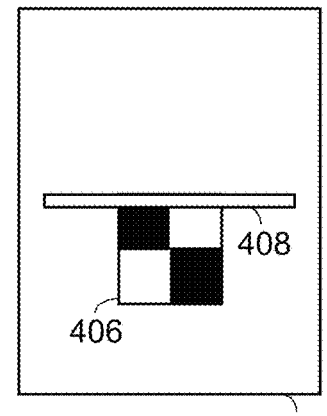
Figure 4F:
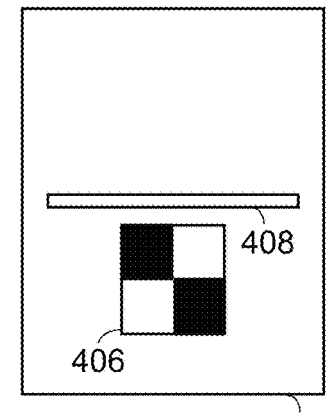
Figure 4G:
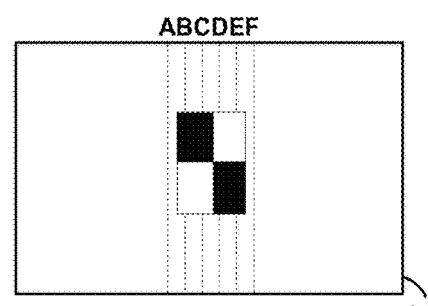

In additional or alternative embodiments, the method may involve carrying out the same analysis with respect to properties of items being handled within an industrial (e.g., manufacturing) process. For example, the process may involve carrying out the analysis to identify a change with respect to a property of items that are handled within an industrial process. FIGS. 4A-4G provide an example of a representation of an analysis of a property of a particular item 406 moving through an industrial process according to various embodiments. In this example, the method involves monitoring the property with respect to a pattern associated with the items as they pass through the industrial process. Here, for example, the pattern may involve a quality, texture, shape, and/or the like of the surface of the items. As shown in the sequence of media elements of FIGS. 4A-4F, the method involves capturing the item 406 as the item 406 passes through an area of interest 408 that lies within the field of view 400 as the item 406 moves through the industrial process. In various embodiments, the method may involve recording attribute values (e.g., brightness, color, etc.) from pixels in the area of interest 408 and assembling the attribute values into a graphical representation 410 representing the property (e.g., the pattern) of the item 406, as shown in FIG. 4G. In some embodiments, the method may involve assembling and comparing graphical representations 410 representing the property (e.g., the pattern) of other items 406 that pass through the industrial process to identify a change in the property (e.g., the pattern) of the items 406.

For example, FIGS. 5A-5F illustrate an example of the sequential elements of media (e.g., sequential frames and/or images) capturing the pattern of a second, different item 506 as the item 506 moves through the particular area, part, portion, and/or the like of the industrial process. Here, the pattern of the item 506 is captured, as shown in the sequence of media elements of FIGS. 5A-5F, as the item 506 passes through the area of interest 408 that lies within the field of view 400 as the item 506 moves through the industrial process. In this instance, the pattern on the second item 506 is different than the pattern on the first item 406 that moved through the particular area, part, portion, and/or the like of the industrial process. Therefore, the method may involve assembling a graphical representation 510 representing the pattern of the second, different item 506, as shown in FIG. 5G, and comparing the graphical representation 410 representing the pattern of the first item 406 with the graphical representation 510 of the pattern of the second item 506 to detect that the pattern (e.g., surface texture) on the items 406, 506 has changed.

Thus, various embodiments of the disclosure can be used in monitoring and/or analyzing properties of items in a process such as, for example, monitoring and/or analyzing values, characteristics, patterns, and/or the like of a property for a series of items during manipulation by machine components. Accordingly, the method can be used in various embodiments to perform such an analysis in helping diagnose item properties, characteristics, and/or the like affecting how an equipment component interacts with items during manufacture.

In additional or alternative embodiments, the method may involve capturing one or more attribute values for pixels with respect to media recorded for one or more equipment components and/or items being handled within an industrial (e.g., manufacturing) process that correlate to one or more properties used in controlling one or more processing parameters of the industrial process. As previously noted, an entity may wish to measure certain properties of equipment components and/or items being handled (referred to as objects) during performance of an industrial process for the purpose of using the measurements to control the equipment.

For example, equipment used in manufacturing paper may include a set of actuators that feeds pulp to the equipment. In addition, the equipment may also include one or more steam boxes after the press section of the equipment to reduce the paper moisture by increasing the sheet temperature. These steam boxes can be non-profiling and/or profiling. A non-profiling steam box applies steam evenly across the entire width of the equipment. A profiling steam box is divided into sections across the width of the equipment and the steam flow to each section can be adjusted to produce a uniform CD (cross direction) moisture profile.

In many cases, an entity operating the equipment will use a quality control system (QCS) to control the actuators and/or steam boxes to ensure uniform distribution (profiles) of several properties that define the specification of a given paper grade for the paper manufactured by the equipment. For example, the QCS may use properties such as moisture, caliper (thickness), and/or basis weight (paper weight). The entity may use one or more scanners to measure these properties. For example, the equipment may include multiple scanners that use different scanner configurations to measure properties important to the process at given locations along the manufacturing process. Here, for example, each of the scanners may have a measurement head travelling across the paper web, and the measurement head may have various sensors that measure different attributes.

In various embodiments, the method involves extracting a set of pixels from media recorded of one or more monitored objects (e.g., one or more equipment components and/or items). In some instances, the method may involve extracting multiple sets of pixels from multiple media recorded on the one or more monitored objects. For example, the method may involve extracting the multiple sets of pixels from media recorded by multiple recording equipment located at different points, locations, and/or the like along the industrial process. As a specific example, the method may involve extracting a first set of pixels from media recorded on the one or more monitoring objects using a video camera at a first location along the industrial process and a second set of pixels from media recorded on the one or more monitoring objects using an infrared camera at a second location along the industrial process.

In addition, the method may further involve generating one or more attribute profiles from the sets of pixels. For example, the method may involve generating a first attribute profile based on attribute values, such as color, brightness, etc., extracted from a first set of pixels. In addition or alternatively, the method may involve generate a second attribute profile based on attribute values, such as temperature, reflection, etc., extracted from a second set of pixels.

Accordingly, the attribute profiles may have either a linear or a non-linear correlation to mapped profiles of measurements for one or more properties used by the entity in controlling the one or more processing parameters of the industrial process. For example, the method may involve generating a brightness profile from extracting brightness values from a set of pixels found in media recorded of a paper web using a video camera that may correlate to a profile of thickness measurements normally generated by a caliber gauge during manufacturing of paper. Likewise, the method may involve generating a temperature profile from extracting temperature value from a set of pixels found in media recorded of the paper web using an infrared camera that may correlate to a profile of moisture measurements normally taken by a moisture sensor during manufacturing of paper. Accordingly, the one or more attribute profiles generated from the set of pixels can be mapped to profiles (referred to as mapped profiles) of the properties used in controlling the one or more processing parameters of the industrial process. These mapped profiles can then be used in controlling the one or more processing parameters.

In particular embodiments, the method may involve performing the mapping of the attribute profiles (attribute values therein) to the mapped profiles, and then providing the mapped profiles to the QCS to be used in controlling the one or more processing parameters of the industrial process. In additional or alternative embodiments, the method may involve providing the attribute profiles to the QCS, and the QCS then performs the mapping of the attribute profiles to the mapped profiles for use in controlling the processing parameters of the industrial process.

Therefore, returning to the example involving manufacturing paper, the equipment used in manufacturing the paper may have a set of actuators that feeds pulp to the equipment, as well as one or more steam boxes used to reduce paper moisture by increasing the sheet temperature. Here, an entity operating the equipment may be using a QCS to control the actuators and/or steam boxes to ensure uniform distribution (profiles) of several properties that define the specification of a given paper grade for the paper manufactured by the equipment such as moisture, caliper (thickness), and/or basis weight (paper weight).

Figure 6:
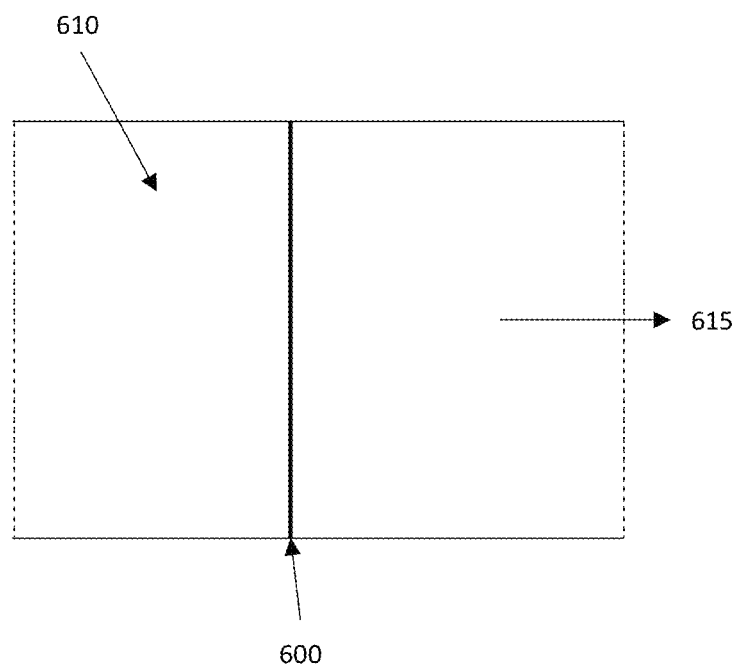
FIG. 6 provides an example of a slice line of pixels that can be use in providing a measurement profile in accordance with various embodiments of the disclosure.

In this example, the method may involve initially defining one or more slice lines 600 for the paper web 610 that are perpendicular to the web movement 615 and spanning between both edges of the paper web 610, as shown in FIG. 6. For example, each of the slice lines 600 may be associated with a camera recording media and positioned at a particular location along the manufacturing process. For example, a first slice line 600 may be defined for a first camera positioned at a location downstream in the manufacturing process from the set of actuators and a second slice line 600 may be defined for a second camera positioned at a location downstream in the manufacturing process from the one or more steam boxes.

Continuing, the method may involve extracting brightness values from a first set of pixels defined by the first slice line 600 from media recorded on the paper web to generate a brightness profile that represents the brightness distribution across the paper web. In addition, the method may involve extracting temperature (heat) values from a second set of pixels defined by the second slice line 600 from media recorded of the paper web to generate a temperature (heat) profile that represents the temperature distribution across the paper web. For example, the one or more slice lines 600 may span fifty pixels, and produce an attribute profile similar to the profile 700 shown in FIG. 7.

Figure 8:
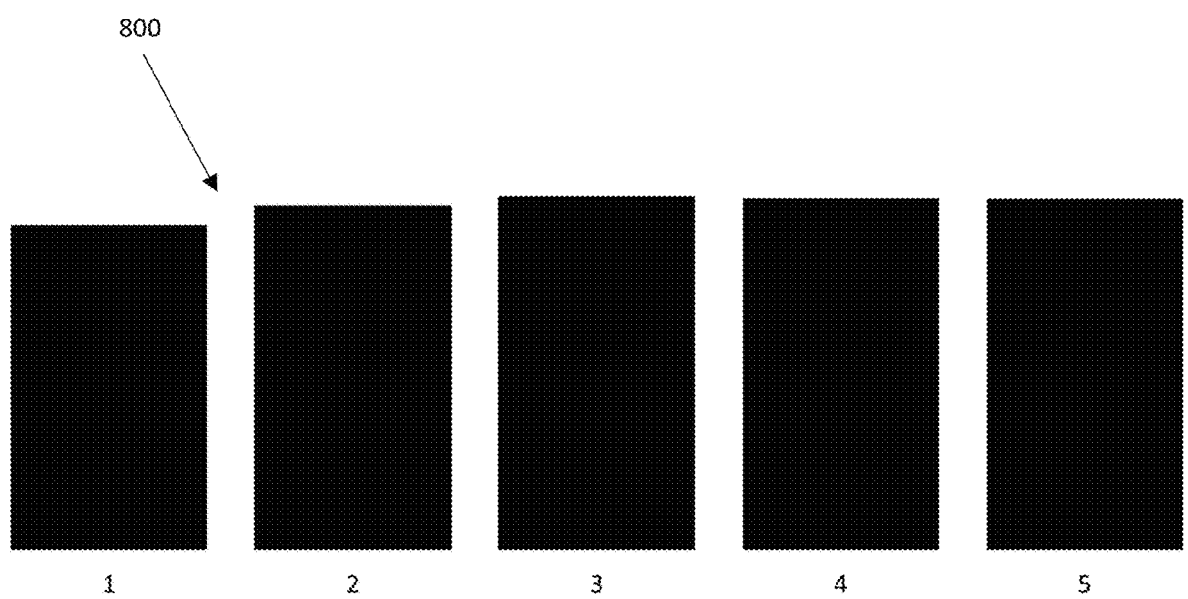
FIG. 8 provides an example of a mapped profile in accordance with various embodiments of the disclosure.

At this point, the method may involve mapping the attribute profiles to mapped profiles that can be used in controlling the actuators and/or steam boxes. For example, the method may involve mapping the brightness profile to a correlated thickness profile that represents a thickness distribution across the paper web. Likewise, the method may involve mapping the temperature profile to a correlated moisture profile representing a moisture distribution across the paper web. For example, assuming there are five actuators, the method may involve mapping the brightness profile to a mapped profile 800 with values corresponding to the average, minimum, maximum, median, and/or the like pixel values of all pixels mapped to a given actuator as shown in FIG. 8.

In some embodiments, the method may involve providing the mapped profiles (e.g., the thickness profile and the moisture profile) to the QCS so that the QCS can use the mapped profiles in controlling the actuators and/or steam boxes. In other embodiments, the method may involve providing the attribute profiles (e.g., the brightness profile and the temperature profile) to the QSC to map the attribute profiles to the mapped profiles and then use the mapped profiles in controlling the actuators and/or steam boxes.

For example, the method may involve providing the mapped (thickness and/or moisture) profiles for the actuators and/or steam boxes in real-time so that the profiles can be continuously displayed and/or used for controlling the actuators and/or steam boxes in between scanner cycles. In addition, the method may involve processing the mapped profiles to alarm on deviations from a uniform profile. Here, such alarms may be used to control one or more processing parameters found after the corresponding camera location. For example, one or more mapped profiles may be compared to a uniform profile to detect coater wet streaks and process an alarm. Accordingly, the alarm may lead to triggering the opening of a calendar nip to prevent calendar sheet breaks.

In another example, the method may involve continuously monitoring attribute and/or mapped profiles to detect problems, issues, and/or the like within the industrial process. As a specific example, the method may involve continuously monitoring subsequent temperature profiles to detect an uneven temperature distribution in the cross direction and/or machine direction. Here, the uneven temperature distribution may signal issues with felts, rolls, dryer cans, and/or the like.

In particular embodiments, the method may involve averaging the attribute profiles in the time domain where the attribute value for each pixel is averaged over several media elements (e.g., frames). In addition, the method may involve analyzing the individual points on an attribute profile or each attribute profile in the time domain to determine variations in the direction of the web movement. Such variations can be used, for example, in identifying issues with equipment prior to the corresponding camera location.

Accordingly, the method in various embodiments can provide the mapped profiles needed to control the one or more processing parameters of the industrial process at a faster rate than conventional control systems can provide correlating profiles. As a result, various embodiments of the method help to address the technical challenges that can be encountered by entities in using controls systems that operate at too slow of a rate to timely correct the processing parameters, and avoid the manufacturing of defective items at a large quantity.

Note that embodiments of the method may be used in various other industrial environments for the same purpose of controlling one or more processing parameters of an industrial process. For example, embodiments of the method may be utilized in the steel industry. As a specific example, embodiments of the method may be used in galvanized steel production to control the spray nozzles on the zinc bath used in applying the zinc to the steel. More specifically, embodiments of the method may be used in capturing reflective attributes from media recorded of the coated surface of the steel that correlates to thickness properties of the zinc coating that can be used in controlling the spray nozzles. In another example, embodiments of the method may be used in the automotive industry. As a specific example, embodiments of the method may be used in automotive stamping operations to control processing parameters of the stamping press. More specifically, embodiments of the method may be use in capturing movement attributes from media recorded of an arm of a stamping press placing blanks into the press that correlates to a stamping cycle property for the press that can be used in controlling the pressure plates for the press. Accordingly, embodiments of the method can be used in other industrial environments that will be apparent to those of ordinary skill in the art in light of this disclosure.

Industrial Process Monitoring Module

Figure 9:
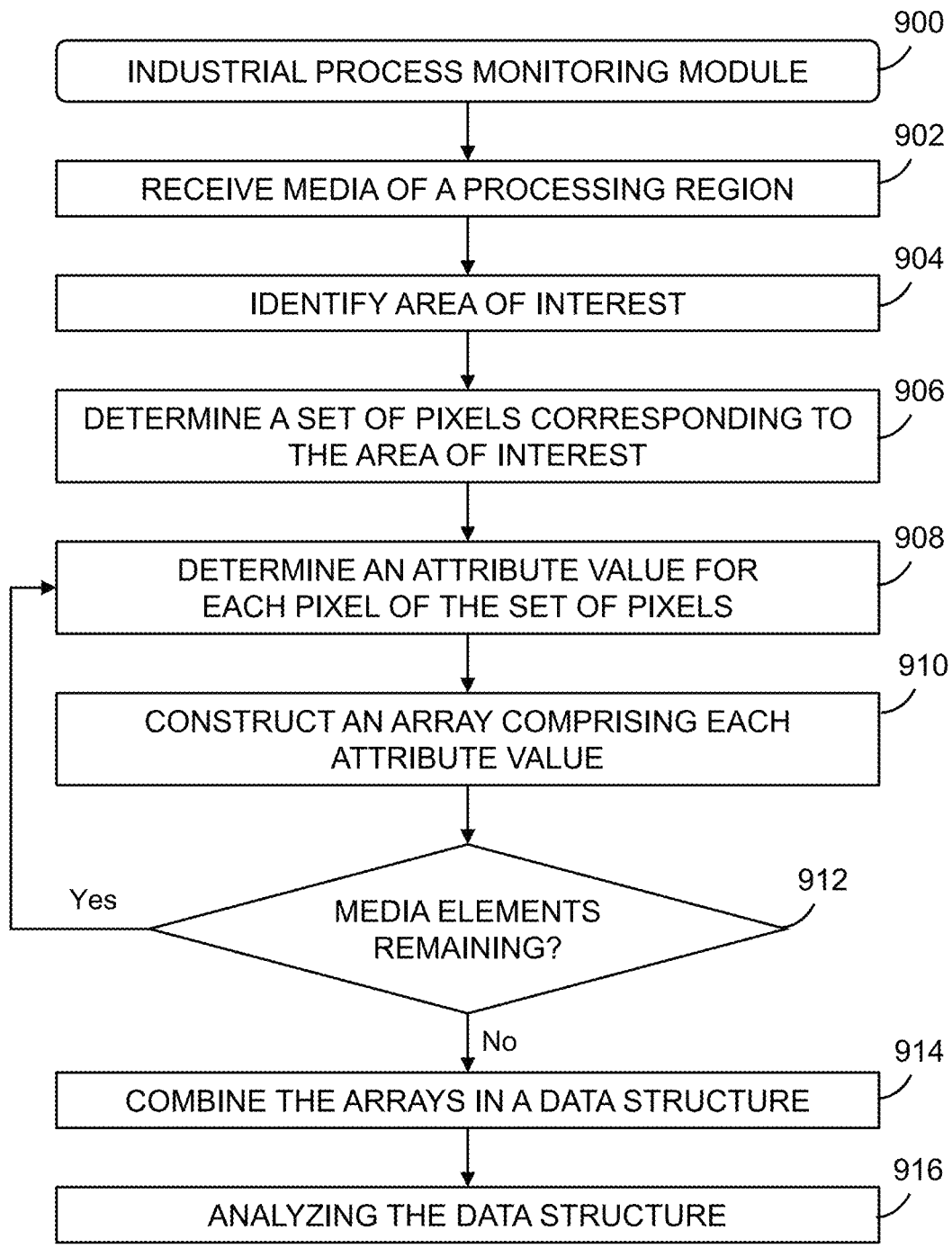
FIG. 9 depicts an example of a process for monitoring an industrial process in accordance with various embodiments of the disclosure.

Turning now to FIG. 9, additional details are provided regarding an industrial process monitoring module 900 for monitoring an industrial process in accordance with various embodiments of the disclosure. For instance, the flow diagram shown in FIG. 9 may correspond to operations carried out, for example, by computing hardware as described herein, as the computing hardware executes the industrial process monitoring module 900.

Figure 7:
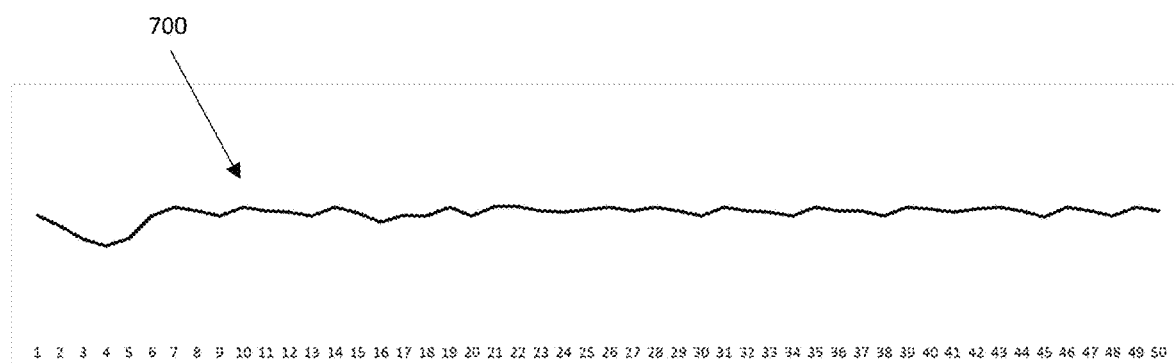
FIG. 7 provides an example of a measurement profile in accordance with various embodiments of the disclosure.

In various embodiments, the industrial process monitoring module 900 may be used for monitoring one or more processing parameters associated with an industrial process and generating data on the one or more processing parameters to assist in diagnosing any defects, errors, problems, and/or the like that may be occurring with respect to the industrial process. For example, the module 900 may be used to construct a timing diagram, such as the graphical representations 110, 210, 310, 410, 510 shown in FIGS. 1G, 2G, 3G, 4G, and 5G. In additional or alternative embodiments, the industrial process monitoring module 900 may be used for monitoring one or more properties of objects associated with an industrial process to be used in controlling one or more processing parameters of the industrial process. For example, the module 900 may be used to construct an attribute profile and/or a correlating mapped profile, as shown in FIGS. 7 and 8, that can be used in controlling the one or more processing parameters of the industrial process.

The process involves the industrial process monitoring module 900 receiving media at operation 902. For example, the media may involve a video, images, and/or the like of a processing region of an industrial process, in which the media comprises a field of view. The media may be provided in real-time (e.g., live-streamed) as the industrial process is being performed, or may be provided after the industrial process has been performed such as, for example, the media may be a recorded media that is uploaded from a storage medium.

At operation 904, The industrial process monitoring module 900 identifies an area of interest found within at least a portion of the field of view. For example, the area of interest may be a line of pixels (e.g., one pixel wide), a square of pixels (e.g., a set number of pixels), a rectangle of pixels (e.g., multiple pixels wide), and/or the like. In some embodiments, the industrial process monitoring module 900 receives an indication from an operator who identifies the area of interest by drawing the area on a graphical user interface as an overlay of the media. In other embodiments, the industrial process monitoring module 900 identifies the area of interest through another source such as metadata, a profile, and/or the like provided along with the media.

At operation 906, the industrial process monitoring module 900 determines a set of pixels corresponding to the area of interest. For example, the module 900 may perform this particular operation by determining the set of pixels underlying the overlay provided by the operator or some other source at operation 904. In some embodiments, the industrial process monitoring module 900, or some other module, may store identification of the pixels associated with the overlay (e.g., grid locations, etc.) in a memory to assist in determining the set of pixels.

At operation 908, the industrial process monitoring module 900 continues with performing an iterative process of analyzing the set of pixels through a plurality of media elements (e.g., frames, images, stills, and/or the like) of the media. In various embodiments, the industrial process monitoring module 900 performs an iteration of the iterative process by determining one or more attribute values for each pixel of the set of pixels in a particular media element, such as, for example, a brightness, a color, an intensity, a temperature, etc. In addition, the industrial process monitoring module 900 may determine a numerical representation of the brightness, color, intensity, temperature, etc. Next, the industrial process monitoring module 900 continues the iteration at operation 910 with constructing a respective array for the media element comprising each of the one or more attribute values for each pixel in the set of pixels. For example, the area of interest may involve a width of one pixel. Therefore, the industrial process monitoring module 900 may construct the array as one-dimensional such as a column vector with each element of the vector providing one or more representations (e.g., one or more numerical values) of the attribute(s) of the corresponding pixel. At operation 912, the industrial process monitoring module 900 determines if media elements remain for the media (i.e., if the video has unanalyzed portions remaining). If media elements remain, then the industrial process monitoring module 900 returns to Operation 908 to analyze the next media element. If no media elements remain, then the industrial process monitoring module 900 proceeds to Operation 914.

At operation 914, the industrial process monitoring module 900 combines each of the respective arrays for each of the media elements into a data structure. In some embodiments, the industrial process monitoring module 900 combines each of the respective arrays into a data structure that is two-dimensional such as a matrix, with each column of the matrix holding an array produced during operations 908 and 910 for a particular element of the media, and each row of the matrix corresponding to a particular pixel of the plurality of pixels found in the area of interest Thus, the arrays can be respectively indexed in the data structure according to a sequence of the plurality of elements for the media, with each array corresponding to a particular element of the plurality of media elements found in the sequence. That is to say, the industrial process monitoring module 900 can arrange the arrays in a sequential order in the data structure, such that a later array in the data structure corresponds to a media element occurring later in the media than a media element corresponding to an earlier array in the data structure. In additional or alternative embodiments, the industrial process monitoring module 900 arranges the arrays in the data structure with an index indicating order, as opposed to being sequentially ordered in the data structure. For example, the industrial process monitoring module 900 can store the data structure in a JSON format with a field indicating media element order for each array.

At operation 916, the industrial process monitoring module 900 conducts an analysis of the data structure to provide data (information) on one or more processing parameters associated with the industrial process. In some instances, the processing parameters may involve parameters associated with movement of a component of equipment (e.g., a machine). For example, a processing parameter may involve a drive force setting, a speed setting, a movement range setting, and/or the like for the component. Additionally or alternatively, the processing parameters may involve parameters associated with movement of items handled within the industrial process. For example, a processing parameter may involve a placement angle, movement speed, process alignment, and/or the like of the items as the items progress through the industrial process. Additionally or alternatively, the processing parameters may involve parameters associated with properties of the items handed within the industrial process, and/or the like. For example, a processing parameter may involve a surface quality, a paint color, a reflective measure, a temperature, and/or the like of the items as the items progress through the industrial process.

In particular embodiments, the industrial process monitoring module 900 conducts the analysis by facilitating generation and transmission of a graphical representation of the data structure to a user device for display. For example, the industrial process monitoring module 900 may facilitate generation and transmission of a graphical representation that is similar to the graphical representations 110, 210, 310, 410, 510 shown in FIGS. 1G, 2G, 3G, 4G, and 5G by providing a visual representation of each array, with each array arranged substantially parallel to a first axis of the graphical representation, and arranged at least substantially sequentially along a second axis of the graphical representation according its respective index of the arrays.

In some embodiments, the industrial process monitoring module 900 provides the graphical representation to an operator for viewing. This can allow the operator to readily discern how an object, such as a component of a machine and/or an item being handled within the industrial process, moves throughout a cycle, and/or determine whether there is a deviation from an expected movement (e.g., the object's range of motion, the object's movement timing, the object's location at certain times in the movement, etc.). In addition, the industrial process monitoring module 900 providing the graphical representation to an operator for viewing can allow the operator to readily discern a change in a property of objects, such as an items being handled within an industrial process, as the items progress through the industrial process. Accordingly, the operator can then take one or more actions to address the change in the property. Further, such a graphical representation can assist an operator in optimizing processes and/or the handling of items, such as assist the operator in identifying timing sequences that can improve processing speed, identifying adjustment in placement of items within an industrial process that can improve manufacturing quality, and/or the like.

In addition, the industrial process monitoring module 900 providing the graphical representation, along with graphical representations generated for other points in time of the industrial process, can provide synchronized views of the process with respect to time in that the industrial process monitoring module 900 can generate the different graphical representations for different points in time from data structures that are produced from the same plurality of media elements gathered through the same area of interest (e.g., the same field of view) for the different points in time. Therefore, in some instances, the industrial process monitoring module 900 can allow for an operator to readily detect variations in the industrial process and/or items manufactured through the industrial process, as well as detect variations in properties of items manufactured through the industrial process.

Alternatively or additionally, the industrial process monitoring module 900 conducts the analysis of the data structure (and/or graphical representation) by providing additional context that may aid an operator in noticing deviations in one or more objects (e.g., deviations in movement of one or more machine components and/or items), as well as deviations in one or more attributes of one or more objects. In some embodiments, the industrial process monitoring module 900 retrieves a template (e.g., master) data structure representing baseline attribute values. For example, the template data may represent an "ideal" or as-designed movement of an object. The industrial process monitoring module 900 may calculate a difference data structure by subtracting the data structure from the template data structure. For example, the industrial process monitoring module 900 may conduct an object-wise subtraction of the data structure and the template data structure to calculate the difference data structure.

In some embodiments, the industrial process monitoring module 900 may provide a feature analysis of the difference data structure (e.g., graphical blob analysis). In additional or alternative embodiments, the industrial process monitoring module 900 may facilitate transmission of a graphical representation of the difference data structure to the user device for display. Here, the graphical representation of the difference data structure may provide an operator with a readily ascertainable, visual indication of deviations in object movement from a baseline.

Alternatively or additionally, the industrial process monitoring module 900 conducts the analysis by facilitating generation and transmission of an attribute profile and/or a correlated mapped profile based on the data structure to a system (e.g., QCS) for the purpose of controlling one or more processing parameters of an industrial process. For example, the industrial process monitoring module 900 may facilitate generation and transmission of an attribute profile and/or mapped profile that are similar to the attribute profile 700 and mapped profile 800 shown in FIGS. 7 and 8, respectively.

In instances where the industrial process monitoring module 900 is being used for this purpose, the industrial process monitoring module 900 may process media, or a portion thereof, having limited data (e.g., frames, images, and/or the like) on the processing region. For example, the industrial process monitoring module 900 may process a media element such as a single frame, image, etc. Therefore, the industrial process monitoring module 900 may analyze a limited number of sets of pixels, and the data structure may comprise a limited array of attributes. In some embodiments, the industrial process monitoring module 900 may perform Operations 914 and 916 within the iterations so that these operations are carried out for each of the plurality of media elements. Here, the industrial process monitoring module 900 may be configured to perform as such so that the industrial process monitoring module 900 can provide attribute profiles and/or mapped profiles to the system timelier so that the system can use the attribute profiles and/or mapped profiles to control the one or more processing parameters of the industrial process in a more-timely (e.g., quicker) fashion.

As previously noted, the data structure includes attribute values extracted from a set of pixels found in media recorded of one or more objects (e.g., one or more components of equipment and/or items). The attribute values may be correlated to property measurements used for the purpose of controlling one or more processing parameters of the industrial process. For example, in a paper manufacturing process, the moisture on the paper may be measured for the purpose of controlling a steam box to reduce the moisture by increasing the sheet temperature. In this example, the attribute values provided in the data structure may be temperature values that can be correlated to moisture measurements that are typically taken to control the steam box.

In particular embodiments, the data structure, itself, may be considered the attribute profile for the attribute. In other embodiments, the industrial process monitoring module 900 may generate one or more attribute profiles from the data structure. For example, the data structure may comprise values for multiple attributes (e.g., brightness, reflectivity, etc.), and the industrial process monitoring module 900 may generate an attribute profile for each type of attribute found in the data structure.

In some embodiments, the industrial process monitoring module 900 provides the one or more attributes profiles to the system (e.g., QCS) that is controlling the one or more processing parameters for the industrial process. Here, the system may then map the one or more attribute profiles to one or more correlating mapped profiles of property values (e.g., paper moisture) that correlated to the attribute values found in the one or more attribute profiles (e.g., temperature). The system can then use the one or more mapped profiles in controlling the one or more processing parameters.

In other embodiments, the industrial process monitoring module 900 carries out the mapping of the one or more attribute profiles to the one or more mapped profiles. In some embodiments, the industrial process monitoring module 900 may use a rules-based model in mapping the attribute values found in the one or more attribute profiles to correlated property values for the one or more mapped profiles. For example, the rules-based model may make use of one or more tables, graphs, rules sets, and/or the like in identifying the correlated property values for the one or more mapped profiles based on the attribute values provided in the one or more measurement profiles.

In some embodiments, the industrial process monitoring module 900 may identify a correlation strength (e.g., a correlation strength value) that identifies how well the attribute values found in the one or more attribute profiles correlate to the property values found in the one or more mapped profiles. For example, the rules-based model may provide a correlation strength for each attribute value based on how well the rules-based model is able to "match" an attribute value from an attribute profile to a property value for a mapped profile. The industrial process monitoring module 900 may then generate an overall correlation strength for the mapped profile by taking the average, mean, median, and/or the like for all the correlation strengths (e.g., values), or the industrial process monitoring module 900 may provide all of the correlation strengths along with the mapped profile. Accordingly, the system may then use the correlation strength in determining whether to use a particular mapped profile in controlling the one or more processing parameters.

Continuing on, alternatively or additionally, the industrial process monitoring module 900 conducts the analysis to aid in optimizing an industrial process by altering the industrial process in real time. In some embodiments, the industrial process monitoring module 900 may use one or more mapped profiles in the same manner as the system (e.g. QSC) in controlling one or more processing parameters of the industrial process. In other embodiments, the industrial process monitoring module 900 may modify the industrial process based on determining that an aspect of the difference data structure, previously discussed, exceeds a threshold.

As a specific example, an aspect of the difference data structure may include a timing delay of a periodic movement of an object (e.g., machine component and/or item) of the industrial process in comparison to a baseline periodic movement of the object. Here, the periodic movement of the object may be the placing of a label on a bottle and the timing delay may involve the placing of the label on a set of bottles which resulted in the label being misplaced on the set of bottles. Therefore, in this example, the industrial process monitoring module 900 may cause a modification to be made to the industrial process by facilitating discarding the set of bottles that were produced during the timing delay. In some embodiments, the industrial process monitoring module 900 can facilitate adjusting a processing parameter of the industrial process, such as a driving force, speed, etc.

Alternatively or additionally, the industrial process monitoring module 900 conducts the analysis of the data structure (and/or a graphical representation) to facilitate operator review by identifying a location of an object (e.g., machine component and/or item) for the industrial process in each of a plurality of arrays. In some embodiments, the industrial process monitoring module 900 may conduct the analysis by identifying an object based on a transition in brightness. For example, referencing FIG. 1G, the industrial process monitoring module 900 may identify the edge of the arm 106 based on a transition from white to black in an array.

In additional or alternative embodiments, the industrial process monitoring module 900 may conduct the analysis by constructing a dataset comprising the locations and corresponding times. For example, referencing FIG. 1G, the industrial process monitoring module 900 may construct a dataset with a sequence of positions of the arm 106 along the vertical axis. In a more complex scenario, the industrial process monitoring module 900 may construct the dataset to include a position (i.e., pixel) along the vertical axis of a brightest pixel, a darkest pixel, or a brightness gradient indicating an edge of a moving object versus time.

Alternatively or additionally, the industrial process monitoring module 900 conducts the analysis by determining a frequency of movement of the object by performing a Fourier transform on the dataset. For example, an operator may use the determined frequency in diagnosing and optimizing the industrial process by determining a vibration frequency of a machine component. In some embodiments, the industrial process monitoring module 900 may also, or instead, conduct the analysis by verifying a graphical representation against other graphical representations, or alternatively verifying a data structure against other data structures, corresponding to various operating conditions, thus further aiding diagnosis and optimization of the industrial process.

Figure 10:
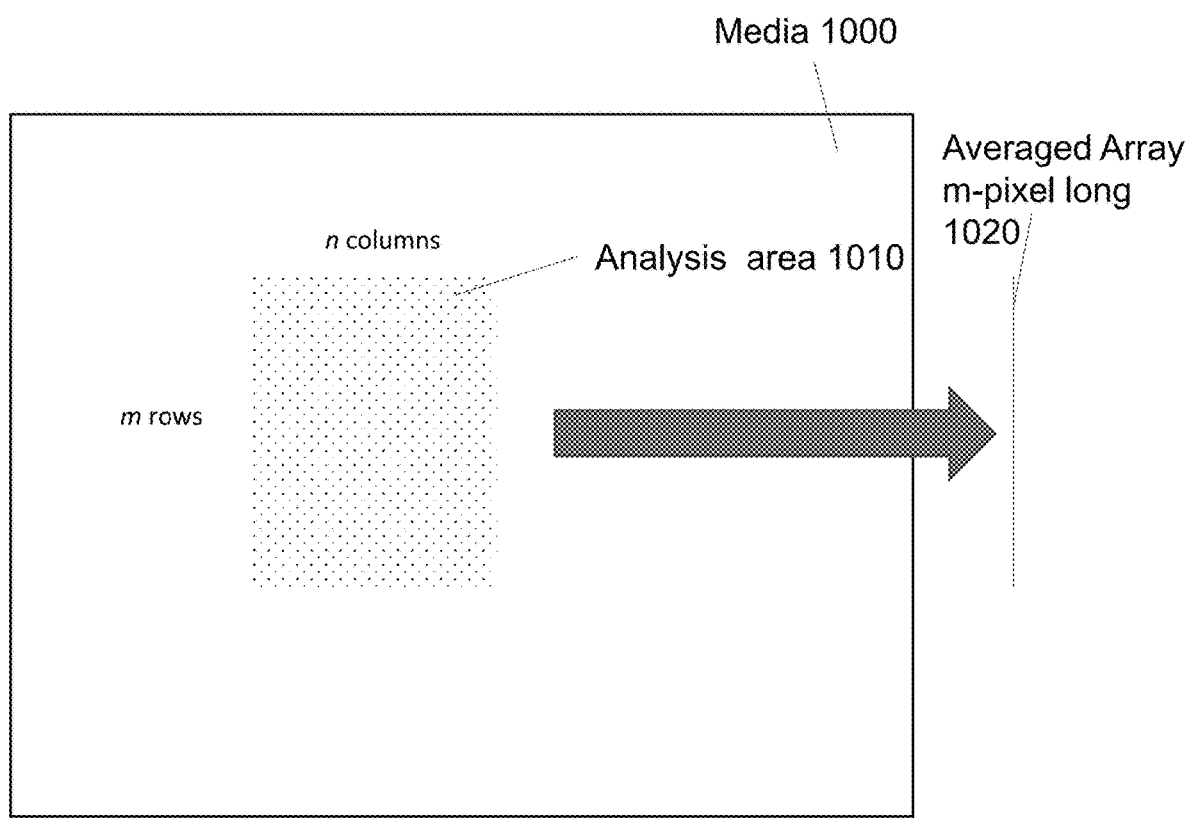
FIG. 10 provides an example of sampling pixels in accordance with various embodiments of the disclosure.

Alternatively or additionally, the industrial process monitoring module 900 conducts the analysis by sampling the pixels for an array to provide further data on one or more processing parameters associated with an industrial process. For example, turning to FIG. 10, the industrial process monitoring module 900 may perform an averaging of values recorded for various pixels over a plurality of arrays found in a data structure. Here, the averaging is shown in the horizontal position. Therefore, the area of interest 1010 captured in media 1000 is shown as a data structure having a plurality of arrays organized in m rows and n columns with each array representing a particular media element (e.g., particular frame and/or image) recorded for the area of interest 1010 in the media 1000. Therefore, the industrial process monitoring module 900 may generate, for each row of pixels (m), an average attribute value, such as brightness, of all the pixels that belong to the row (m) across the plurality of arrays. The result is an averaged array 1020 having each resulting average attribute value generated for each row (m) provided as a value of a single pixel, with the length of the averaged array 1020 equal to the number of rows (m) in the data structure. Accordingly, the averaged array 1020 can represent the attribute values of the entire data structure. Such an averaged array 1020 may be used by an operator in conducting further analysis on the industrial process.

Figure 11:
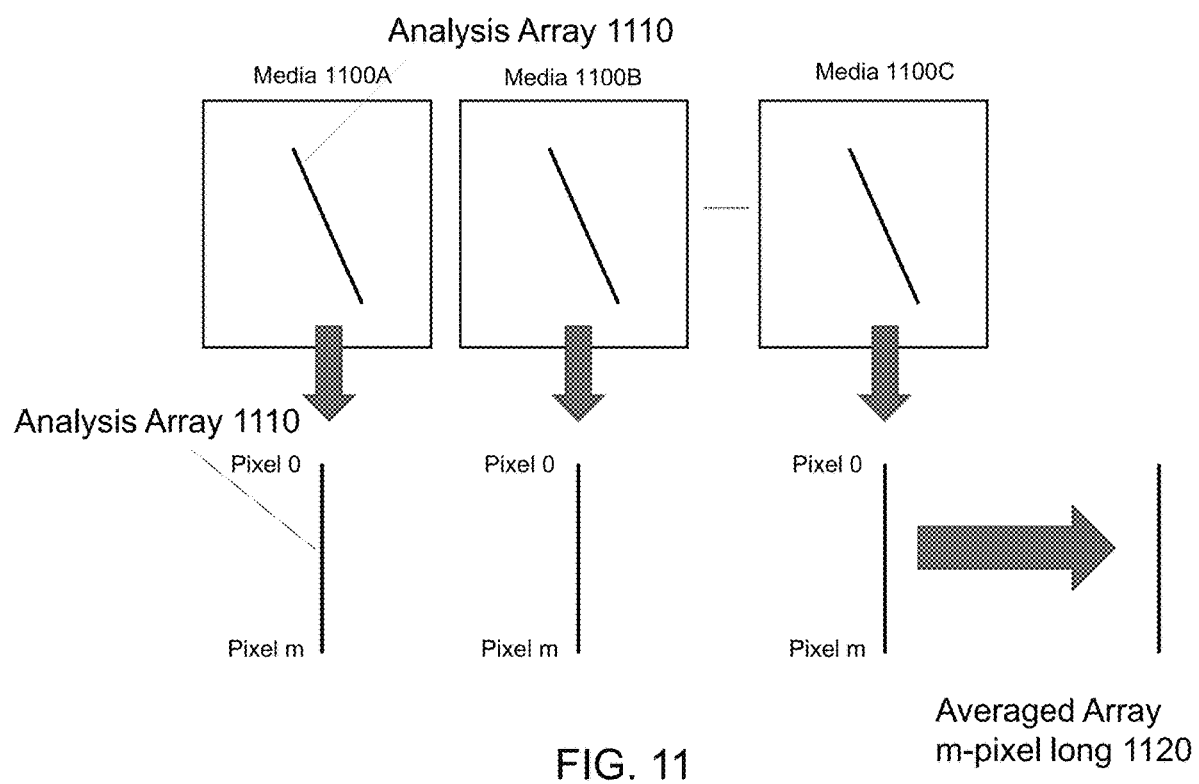
FIG. 11 provides another example of sampling pixels in accordance with various embodiments of the disclosure.

In another example, shown in FIG. 11, the industrial process monitoring module 900 may perform an averaging of values recorded for various pixels over a particular array representing a particular media element found in a plurality of data structures. Again, the averaging is shown in the horizontal position. The area of interest has been captured in a plurality of media 1100A, 1100B, 1100C in which a data structure has produced for each media 1100A, 1100B, 1100C. Here, each data structures includes a particular array 1110 having m pixels representing a particular media element captured in the corresponding media 1100A, 1100B, 1100C. An n set of the particular array 1110 is provided across the plurality of media 1100A, 1100B, 100C. Therefore, the industrial process monitoring module 900 generates, for each location of corresponding pixels found within the n set of the particular array 1110, an average attribute value, such as brightness, of all the corresponding pixels that belong to each of the particular arrays 1110 across the n set of particular arrays 1110. The result is an averaged array 1120 having each resulting average attribute value generated for each location of corresponding pixels provided as a value of a single pixel, with the length of the averaged array 1120 equal to the number of pixels (m) in the particular array 1110. Accordingly, the averaged array 1120 can represent the attribute values of the entire data structures generated for the plurality of media 1100A, 1100B, 1100C recorded for the entire area of interest. Again, such an averaged array 1120 may be used by an operator in conducting further analysis on the industrial process.

In some instances, the media may include processing portions and interstitial portions such as, for example, portions where a component or item is moving, and portions where the component does not move, or no items are present. In a periodic process, the media may capture alternating processing and interstitial portions (e.g., processing-interstitial-processing-interstitial-etc.). In these instances, the industrial process monitoring module 900 may process the interstitial portions to introduce arrays that do not necessarily contain meaningful data and/or obscure underlying, meaningful data representing a component and/or item movement that is useful in diagnosing and analyzing a process. Therefore, in some embodiments, the industrial process monitoring module 900 may remove the interstitial portions of media by determining a beginning media element (e.g., frame, image, and/or the like) of an interstitial portion and an ending media element of the interstitial portion, and excluding such media elements from the plurality of elements analyzed during Operations 908-914.

For example, the examined industrial process may be periodic (e.g., the process may have a processing portion, followed by an interstitial portion, and then another processing portion). Here, the industrial process monitoring module 900 may determine a beginning media element of an interstitial portion based at least in part on receiving a first trigger signal indicating an ending of a movement cycle of an object of the industrial process. Further, the industrial process monitoring module 900 may determine an ending frame of the interstitial portion based at least in part on receiving a second trigger signal indicating a beginning of the movement cycle of the object of the industrial process. The industrial process monitoring module 900 may then exclude the media elements between the beginning media element and the ending media element from the media elements analyzed during Operations 908-914.

Alternatively or additionally, the industrial process monitoring module 900 may determine the beginning and ending media elements of an interstitial portion based at least in part on features identified within the media itself. For example, the industrial process monitoring module 900 may involve determining a beginning media element of an interstitial portion by detecting a first change in an attribute value of a particular pixel. As a specific example, such as a change can indicate that an object has returned to a beginning ("home") position, or such a change can indicate that an item is no longer in a processing region within the field of view. Similarly, the industrial process monitoring module 900 may determine an ending media element of the interstitial portion by detecting a second change in the attribute value of the particular pixel. For example, such as a change can indicate that an object has started movement away from the beginning position, or such a change can indicate that an item has entered the processing region. Depending on the embodiment, the industrial process monitoring module 900 may determine the first change and/or the second change based on pixel attributes either inside or outside of the area of interest. For example, a first area of interest may indicate a beginning and an ending of a processing cycle, and the industrial process monitoring module 900 analyzes pixel attributes from a second area of interest.

In some instances, the industrial process monitoring module 900 may analyze a periodic process where the second change (indicating an ending of an interstitial portion) indicates a beginning media element of a processing portion, and the first change (indicating a beginning of the interstitial portion) indicates an ending media element of the processing portion. Here, the industrial process monitoring module 900 may determine an elapsed time of the processing portion, for instance based on a property such as a frame rate of the media, a number of frames between the second change and the first change, and/or the like.

In some instances, the industrial process monitoring module 900 may analyze a periodic process where a duration of a processing portion may vary. For instance, a manufacturer may set a manufacturing speed based on a desired output rate of a final item. When this occurs, media, such a video with a constant frame rate, may capture more frames than would be captured for a faster manufacturing speed. For example, a video capturing frames at sixty frames per second can capture twice as many frames as a result of a change in processing speed causing a process to take two seconds, rather than one second. Without correction, such cases can, for example, lead to an altered graphical representation being displayed, potentially leading to an operator mistakenly suspecting a deviation from a baseline movement.

In various embodiments, the industrial process monitoring module 900 can address these cases by removing (downsampling) or adding (upsampling) media elements (e.g., frames, images, and/or the like) corresponding to a processing portion based on an elapsed time. For example, the industrial process monitoring module 900 can remove elements from the plurality of media elements in response to the elapsed time exceeding a baseline processing time (e.g., the industrial process monitoring module 900 can remove every other media element in response to the elapsed time being twice as long as a baseline processing time). Alternatively, the industrial process monitoring module 900 can add elements to the plurality of media elements in response to the elapsed time being less than the baseline processing time (e.g., the industrial process monitoring module 900 can duplicate every media element, and incorporate the duplicated media elements into the data structure adjacent the original media element, in response to the elapsed time being half as long as a baseline processing time).

In some embodiments, the industrial process monitoring module 900 may perform Operation 902 by receiving the media at least substantially in real time. In these embodiments, rather than upsampling or downsampling the media, the industrial process monitoring module 900 may alter a property of the device (e.g., camera) providing the media such as, for example, altering the camera frame rate. For example, the industrial process monitoring module 900 may receive a speed measurement indicating a speed at which an object of the industrial process is moving (e.g., a speed of an object such as a conveyer). Here, the industrial process monitoring module 900 may adjust a frame rate of the camera based on a difference between the speed measurement and a baseline speed. In this manner, the industrial process monitoring module 900 can capture a substantially equal number of media elements for each processing cycle, regardless of processing speed.

Movements of machine components during a process may obscure or expose light. Changes in light and shadows may hide features in the movement of a component or item in the industrial process. For example, returning to FIGS. 1A-IF, a shadow covering the lower half of the field of view may preclude identification of arm movements below horizontal. Therefore, in particular embodiments, the industrial process monitoring module 900 can identify a control area of the field of view that comprises control pixels corresponding to a non-moving object of the industrial process. For example, the control area may include pixels that do not fall in a shadow, or pixels that are in a shadow simultaneous with an object of interest. In some embodiments, the industrial process monitoring module 900 can determine a metric of respective attribute values of the control pixels over a set of media elements corresponding to a movement cycle of an object of the industrial process, such as an average brightness. In addition, the industrial process monitoring module 900 can include calibrating the attribute values of the plurality of pixels corresponding to the area of interest based on the metric, for instance, by subtracting or scaling attribute values of pixels within an area of interest based on the metric of the control pixels. In this manner, the industrial process monitoring module 900 can allow accurate representations of movements to be obtained despite variations in illumination.

Example Computing Hardware

Figure 12:
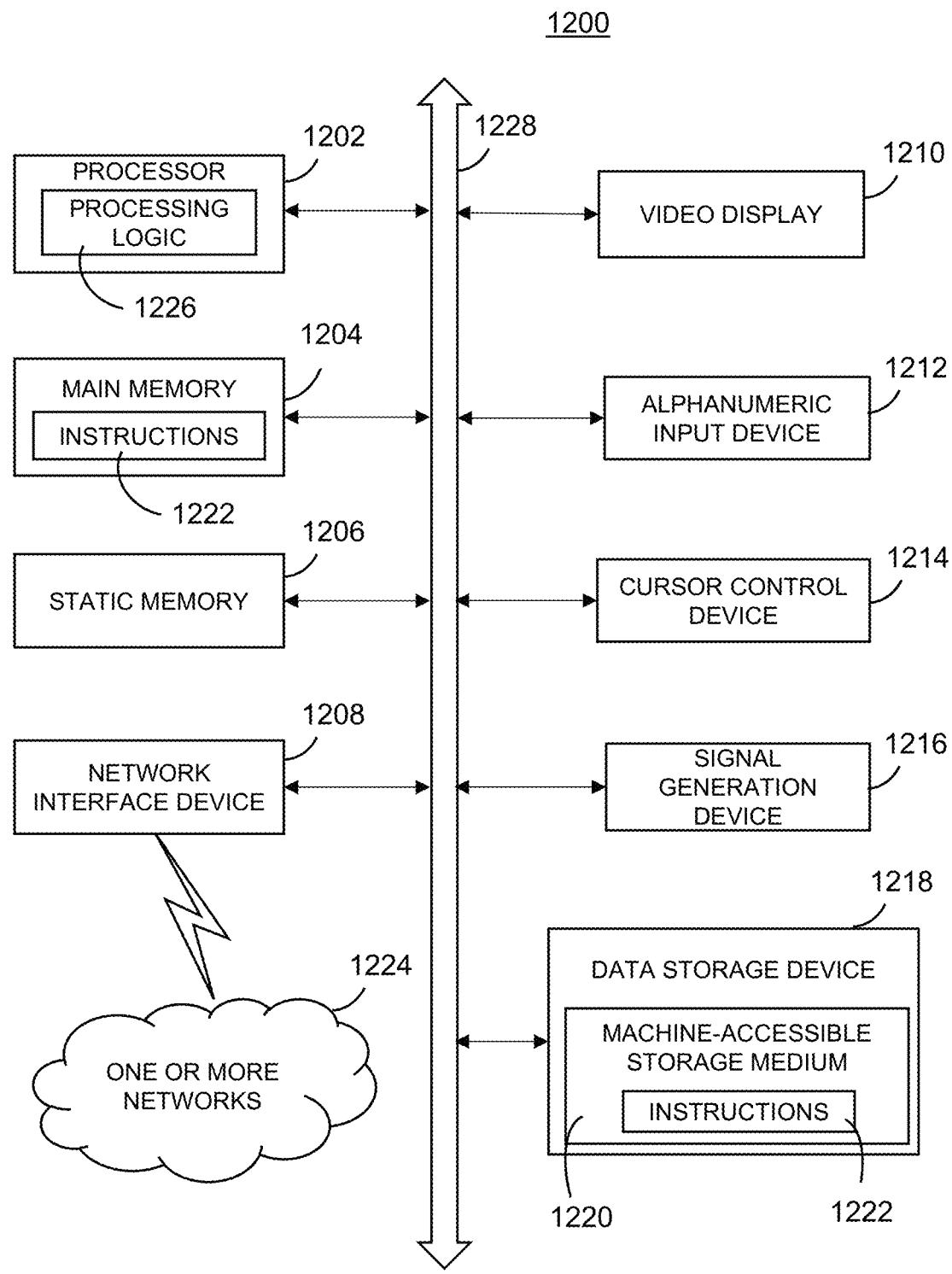
FIG. 12 is a diagram illustrating an example of computing hardware that can used in accordance with various embodiments of the disclosure.

FIG. 12 illustrates a diagrammatic representation of a computer architecture of computing hardware 1200 that may be used in practicing various embodiments of the present disclosure. In particular embodiments, the computing hardware 1200 may be suitable to receive input data from various types of devices, sensors, etc., as well as store, process, and transmit data.

In particular embodiments, the computing hardware 1200 may be connected (e.g., networked) to one or more other computers using Bluetooth, NFC, another form of short-range wireless communications, and/or other wireless communications technologies. The computing hardware 1200 may also, or instead, be communicatively connected to one or more other computers using a physical connection and/or cable (e.g., USB, mini-USB, micro-USB, standard USB of any type, etc.). The computing hardware 1200 may also, or instead, connect to other computers using a LAN, an intranet, an extranet, and/or the Internet (e.g., using any wired and/or wireless communications connection). The computing hardware 1200 may be, or may be based on, any type of device having one or more processors and data storage capabilities and capable of executing a set of instructions (sequential or otherwise) that specify actions to be taken by that computer. Further, while only a single computer is illustrated, the term "computer" shall also be taken to include any collection of computers that individually or jointly execute a set (or multiple sets) of instructions to perform any one or more of the methodologies discussed herein, such as the data compression and/or decompression methods described in more detail below.

The computing hardware 1200 may include a processing device 1202 (e.g., one or more computer processors) and a main memory 1204 (e.g., read-only memory (ROM), random access memory (RAM), flash memory, dynamic random access memory (DRAM) such as synchronous DRAM (SDRAM) or Rambus DRAM (RDRAM), etc.) storing instructions 1222 that may be executed by the processing device 1202. The computing hardware 1200 may also include a static memory 1206 (e.g., flash memory, static random-access memory (SRAM), etc.) and a data storage device 1218. All such components of the computing hardware 1200 may communicate with each other via a bus 1228.

The processing device 1202 represents one or more general-purpose processing devices such as a microprocessor, a central processing unit, and the like. More particularly, each processing device of the processing device 1202 may be a complex instruction set computing (CISC) microprocessor, reduced instruction set computing (RISC) microprocessor, very long instruction word (VLIW) microprocessor, Scalar Board, a processor implementing other instruction sets, or a processor implementing a combination of instruction sets. Each processing device of the processing device 1202 may also, or instead, be one or more special-purpose processing devices such as an application specific integrated circuit (ASIC), a field programmable gate array (FPGA), a digital signal processor (DSP), a network processor, and the like. The processing device 1202 may be configured to execute processing logic 1226 for performing various operations and steps discussed herein.

The computing hardware 1200 may further include a network interface device 1208 that may include one or more NFC components, Bluetooth components, any other type of short-range wireless communications components, and/or any other wireless communications components that may allow communication directly with any other device and/or via any type of network. The network interface device 1108 may also, or instead, include one or more wired communications components that may facilitate wired communications via a physical connection to one or more other devices (e.g., USB, mini-USB, micro-USB, standard USB of any type, etc.). The computing hardware 1200 also may include a video display unit 1210 (e.g., a flexible computer display, a liquid crystal display (LCD), an LED display, or any other suitable display), an alphanumeric or other type of input device 1212 (e.g., a keyboard, a touchscreen, etc.), a cursor control or other input device 1214 (e.g., touch-sensitive input device, or other suitable input device, etc.), and a signal generation device 1216 (e.g., a speaker, function generator, etc.).

The data storage device 1218 may include a non-transitory computer-accessible storage medium 1220 (also known as a non-transitory computer-readable storage medium or a non-transitory computer-readable medium) on which may be stored one or more sets of instructions 1222 (e.g., software) embodying any one or more of the methodologies or functions such as the industrial process monitoring module 900 as described herein. The instructions 1222 may also reside, completely or at least partially, within the main memory 1204 and/or within the processing device 1202 during execution thereof by the computing hardware 1200. The main memory 1204 and the processing device 1202 may also constitute computer-accessible storage media. The instructions 1222 may further be transmitted or received directly from another device and/or over a network (e.g., one or more networks 1224) via the network interface device 1208.

While the computer-accessible storage medium 1220 is shown in an exemplary embodiment to be a single medium, the terms "computer-accessible storage medium," "computer-readable storage medium," and "computer-readable medium" should be understood to include a single medium or multiple media (e.g., a centralized or distributed database and/or associated caches and servers) that store the one or more sets of instructions. The terms "computer-accessible storage medium," "computer-readable storage medium," and "computer-readable medium" should also be understood to include any medium that is capable of storing, encoding, or carrying a set of instructions for execution by the computer and that cause the computer to perform any one or more of the methodologies of the present invention. The terms "computer-accessible storage medium," "computer-readable storage medium," and "computer-readable medium" should accordingly be understood to include, but not be limited to, solid-state memories, optical media, magnetic media, etc.

Also, while the computing hardware 1200 is shown in FIG. 12 as including various components, it should be understood that the computing hardware 1200 may include greater or fewer components in other embodiments. For example, in certain embodiments, the computing hardware 1200 may not include a video display unit 1210, signal generation device 1216, or other components shown in FIG. 12.

Example System Architecture

Figure 13:
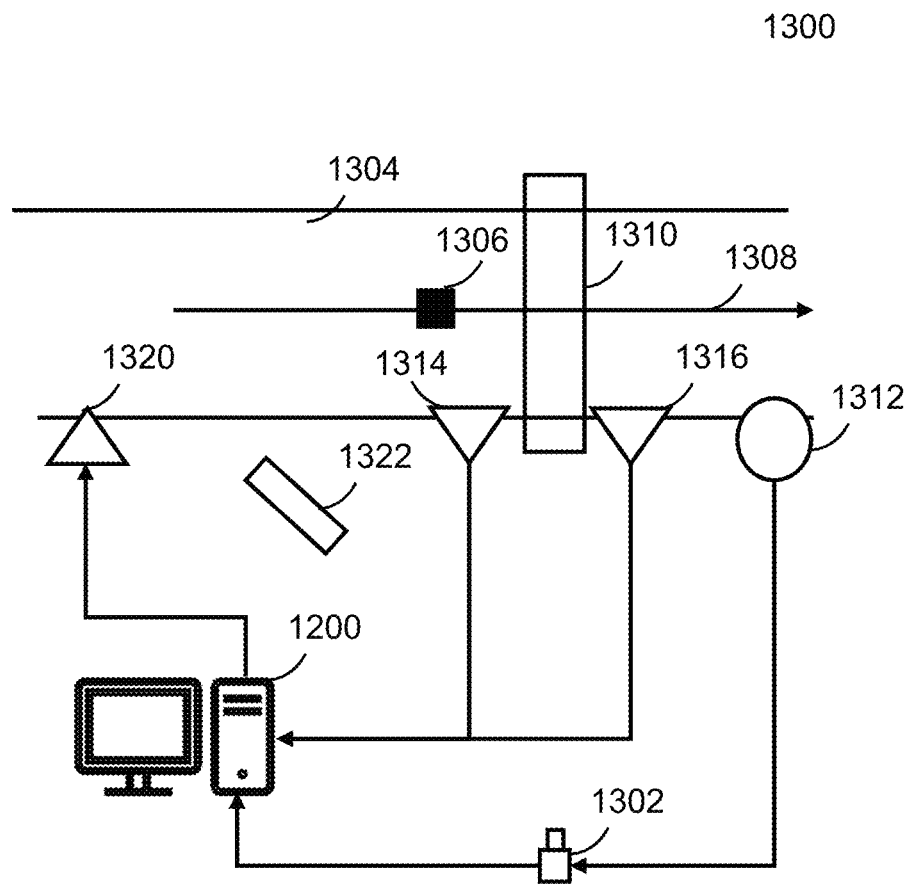
FIG. 13 is a diagram illustrating an example of a system environment in which various embodiments of the disclosure may be implemented.

FIG. 13 is a diagram illustrating an example of a system architecture 1300 in which various embodiments of the disclosure may be implemented. As shown in FIG. 13, the system architecture 1300 may include recording equipment 1302 such as, for example, an area scan camera, a line scan camera, an infrared camera, and/or the like that is pointed at a dynamic processing region 1304. For example, the dynamic processing region 1304 may include an area, location, and/or the like of an industrial process where an item 1306 handled within the industrial process is transferred along a path 1308 and processed within a field of view of the recording equipment 1302.

In various embodiments, computing hardware 1200 may execute the industrial process monitoring module 900, as described herein, to monitor aspects of the industrial process via an area of interest 1310 within the field of view (e.g., manipulation of the item 1306). Accordingly, the area of interest 1310 may be based on the recording equipment's view and process behavior being monitored. For example, the area of interest 1310 may be based on encapsulating motion of a monitored object (e.g., the item 1306 and/or a component of a machine) while avoiding interference from inconsequential motion.

The system architecture 1300 may also include other components such as, for example, a speed encoder 1312 for measuring movement of the item 1306, an acquisition start trigger 1314, and/or an acquisition end trigger 1316. For example, the acquisition start trigger 1314 and/or the acquisition end trigger 1316 may include a Hall effect sensor, sonic proximity sensor, laser proximity sensor, continuity or voltage sensor, etc. In some embodiments, data from the speed encoder 1312 may be used to control the frame rate of the recording equipment 1302, frequency of the recording equipment 1302, and/or the like to facilitate visualization of the process in substantially equal increments of distance traveled by the item 1306.

The acquisition start trigger 1314 and/or acquisition end trigger 1316 may be connected to the computing hardware 1200 to facilitate the computing hardware 1200 in capturing processing portions and excluding interstitial portions of video. Further, an output module 1320 may provide results of process verification to other systems (e.g. QCS), process controls, and/o the like, as well as personnel, to alter processing parameters of the industrial process that may lie upstream and/or downstream of the recording equipment 1302. The system architecture 1300 may further include a light 1322 to aid in constant and even illumination. As described above, the computing hardware 1200 may be configured to execute the industrial process monitoring module 900 without input from the acquisition start trigger 1314 and/or the acquisition end trigger 1316 (e.g., using features of the captured video to identify a start and stop of a process).

In certain embodiments, resolution of the recording equipment 1302 may be set to a high resolution for a given model and frame rate. In some instances, the pixel resolution and field of view may influence the resolution of a graphical representation and/or a measurement profile. For instance, a smaller field of view and/or higher pixel resolution may result in higher spatial resolution of the graphical representation and/or measurement profile. Other recording equipment settings such as gain, exposure, etc., may be set to maximize the ability to monitor the industrial process within the view of the recording equipment 1302.

Manufacturing Process Failure Prediction and Prevention Systems and Methods

Overview

Sheet breaks are one of the most common runnability issues on pulp, paper, and tissue machines (e.g., paper machines). Paper machines may be equipped with camera systems that helps operators identify the location where the break started and provide an image of a developing break. Often operators may use this information to identify the root cause of the break. For example, if a break is caused by a lump of fiber embedded in paper, one can deduce that the problem is with paper formation. However, in most cases operators can identify the type of defect but not the root cause. Often, defect identification often occurs after a break occurs. As such, it can be technically challenging to identify potential breaks prior to them occurring, in order to reduce paper machine downtime.

Various aspects of the systems describe herein comprise visual and infrared cameras that may be configured to predict the probability of a break based on the camera input. In general, the prediction may include a prediction as to whether a sheet break may occur when paper is not strong enough to withstand forces exerted by a particular paper machine. For example, a wet spot detected by an IR camera in otherwise dry paper may create a weak spot which can turn into a hole or an edge crack, depending on the wet spot location, and this can happen even if the forces exerted on the paper web are within normal operating conditions. As such, the system may use one or more IR cameras to identify wet spots in order to generate a prediction as to a likelihood of a sheet break based on a position of the wet spot, size of the wet spot, etc. Alternatively, a defect free paper web subjected to excessive forces in a particular paper machine location may exceed what the paper web can withstand and result in a sheet break. Additionally, a combination of weak spots and excessive forces may result in a high probability that a sheet break will occur.

In particular embodiments, the system is configured to analyze and process video from one or more visual cameras to determine amplitudes and frequencies of the paper web movements caused by the forces of the paper machine process. For example, by measuring the amplitudes and frequencies of a press release point, the system can analyze the dynamic forces impacting the web at the press location and identify the machine components that produce forces at a given frequency. The same approach may apply to paper edge and dry line movements, along with many other parameters measurable by one or more imaging devices. Therefore, being able to track frequencies and amplitudes in real time may provide data for generating a prediction as to which point the paper is likely to break may allow the system to predict sheet breaks caused by undue forces.

The system may use LWIR (long wave infrared) cameras to generate heat maps that represent paper web temperature distribution. Since paper temperature is proportional to paper moisture content temperature data can be used to generate a prediction as to whether a particular sheet may break (e.g., due to a wet spot). This is because the paper strength depends mainly on the inter-fiber bonding which, when disrupted by water immersion, may leave only about 2-3% of the dry tensile strength. As such, in various aspects, the system may be configured to generate a prediction that a sheet break is likely to originate at or near a wet spot even if the forces exerted by the paper machine are normal. The system is configured to process heat maps in substantially real time to detect areas of lower temperature and the system then classifies these areas by their location on the paper web, size, intensity (net difference in temperature) and gradient (the degree of change from normal temperature). The CD (cross direction) location of the weak spot is important since a weak spot can be tolerated inside of the paper web but not at the paper edges. The size is important because a larger spot has a higher probability of being subjected to destructive forces. The intensity is important since a lower temperature corresponds to a higher moisture content and thus lower tensile strength. The gradient is important since the paper is more likely to break near a high gradient point. Other parameters such as shape, edge uniformity, etc., can also be used to fully classify the weak spot.

Process frequencies and amplitudes and weak spot classifications can be used to set operational limits automatically using an artificial neural network (ANN). Additional information such as manufactured paper grade, machine speed, etc., is used to refine the analysis.

In various aspects, the system 1400 may process the heat maps, identified, moisture locations, moisture size and shape, and amplitude and frequencies of paper web movement using a rules-based model, a machine-learning model, or both to generate a prediction as to a likelihood of a break. For example, the rules-based model, machine learning model, or combination of both may be configured to process the heat maps, identified, moisture locations, moisture size and shape, amplitude and frequencies of paper web movement, and/or the like in determining the likelihood that a particular break will occur in a particular location. For example, the rules-based model, machine learning model, or combination of both may be configured to generate a prediction based on the location of a wet spot, current vibration levels, etc.

For example, according to particular aspects, the system may use a rules-based model to generate the prediction. The rules-based model may comprise a set of rules that assigns respective breakage risks to each of a plurality of paper factors (e.g., paper grade, identified wet spot location etc.). For example, the set of rules may define one or more rules for assigning impact values based on material type, manufacturing process, etc. Accordingly, the system may maintain the set of rules in some type of data storage, from which the system can access the set of rules for generating the prediction as to the likelihood of a break.

According to other aspects, system may utilize a machine learning model in generating the prediction (or identifying a potential and/or likely break). Here, the machine learning model may be trained using historical data on prior breaks and material factors, identified wet spots, and other sensor readings leading up to the break. In various aspects, the training data may be derived from a plurality of industrial systems across plurality of locations. Accordingly, the machine learning model may be configured using a variety of different types of supervised or unsupervised trained models such as, for example, support vector machine, naive Bayes, decision tree, neural network, and/or the like.

In particular embodiments, the system may implement one or more neural networks to perform any of the big data processing techniques described herein. A neural network, according to various embodiments, comprises: (1) a plurality of nodes that mimic the operation of the human brain; (2) a training mechanism that analyzes supplied information, and (3) a paper break prediction engine for predicting a potential breakage. In various embodiments, each of the nodes comprises one or more weighted input connections, at least one transfer function that combines the inputs, and an output connection. In particular embodiments, the neural network is a variational AE neural network, a denoising AE neural network, or any other suitable neural network.

In various embodiments, the machine learning model and/or neural network may utilize one or more of: (1) frequencies and amplitudes of paper machine components (representing the forces exerted on the paper); (2) detected weak spots (representing paper vulnerabilities); (3) paper machine speed; (4) manufactured paper grade; (5) any other paper machine parameter pertaining to machine runnability; and/or (6) any other suitable factors. In some aspects, the system may use these factors as inputs related to predicting paper breaks. In particular aspects, the training data may enable the neural network and/or other machine learning model to apply identified relationships between the forces exerted on the paper, paper vulnerabilities, and the sheet breaks to identify future sheet breaks before they occur (e.g., by determining a causal relationship between the set of inputs discussed herein and past paper breakage incidents). Applying these operations, the system may determine the probability of a sheet break for the current paper machine conditions and alert the operator or take a prescribed corrective action.

In some aspects, in response to identifying a potential sheet break, the system is configured to automate a response. In some aspects, the automated response may include one or more of: (1) triggering an alarm; (2) stopping a paper machine; (3) modifying an operating speed of at least one paper machine component; (4) reducing pressure on one or more machine components (e.g., rolls); (5) washing one or more felt components; and (6) etc.

In various embodiments, the system is configured to transmit historical data to one or more manufacturers of paper machines. In some aspects, the manufacturers may identify weak points in the machine to provide feedback for potential re-designs of equipment to reduce an instance of paper breakage on a particular machine. In some aspects, the system comprises a communications network accessible by different industrial control systems at different plant locations. In various embodiments, the communications network is configured to share historical data regarding breakage and associated imaging data, sensor measurements, etc.

In still other aspects, the system is configured to generate customized user interfaces for use by manufacturing process operators to identify potential runnability issues, defects, potential sheet breaks, sheet break causes, and the like. As discussed herein, entities may use closed-circuit television systems to monitor equipment used in the industrial processes and/or items produced by these industrial processes for the purpose of detecting malfunctioning equipment and/ or damaging of items (e.g., paper breakages that have already occurred or may potentially occur as a result of current operating conditions). However, these closed-circuit television systems also present technical challenges in that the real-time surveillance provided through these systems may fail to reveal gradual variations over time in a manufacturing process, or minor variations in rapid processes. These systems may further fail to reveal component variations and conditions that may not be visible to an operator whose view is limited to imaging data that includes only visual cameras. In still other aspects, the nature of the associations between relevant industrial events (e.g., process failures such as paper breaks) and process conditions leading to those failures may render it technically challenging top predict future industrial events when similar conditions are encountered.

Sheet breaks are one of the most common runnability issues on pulp, paper, and tissue machines (e.g., paper machines). Paper machines may be equipped with camera systems that helps operators identify the location where the break started and provide an image of a developing break. Often operators may use this information to identify the root cause of the break. For example, if a break is caused by a lump of fiber embedded in paper, one can deduce that the problem is with paper formation. However, in most cases operators can identify the type of defect but not the root cause (e.g., cannot identify the root cause from visual camera imaging alone). Often, defect identification occurs after a break occurs (e.g., an operator identifies the root cause of a break following an investigation after the break occurs). As such, it can be technically challenging to identify potential breaks prior to them occurring, in order to reduce paper machine downtime.

Various aspects of the systems describe herein comprise visual and infrared cameras that may be configured to predict the probability of a break based on the camera input (e.g., by displaying camera, IR, and other data to an operator for use in identifying breakage causes). Identified breakage causes can then be fed into a machine learning model for use in predicting future sheet breaks before they occur. In general, the prediction may include a prediction as to whether a sheet break may occur when paper is not strong enough to withstand forces exerted by a particular paper machine. For example, a wet spot detected by an IR camera in otherwise dry paper may create a weak spot which can turn into a hole or an edge crack, depending on the wet spot location, and this can happen even if the forces exerted on the paper web are within normal operating conditions. As such, the system may use one or more IR cameras to identify wet spots in order to generate a prediction as to a likelihood of a sheet break based on a position of the wet spot, size of the wet spot, etc. In order to identify potential sheet beaks resulting from particular wet spot locations and sizes, the system may require training data in the form of wet spot data leading up to prior sheet breaks in order to correlate particular moisture profiles with potential breakage events. Additionally, a defect free paper web subjected to excessive forces in a particular paper machine location may exceed what the paper web can withstand and result in a sheet break. The system may similarly require user input as training data for correlating such forces to potential future breakage events. Additionally, a combination of weak spots and excessive forces may result in a high probability that a sheet break will occur.

As such, certain aspects of the present system provide improvements to computing systems used for enabling a user to identify certain abnormalities in an industrial process and correlate those abnormalities to certain industrial events (e.g., breakage events or other events described herein) by, for example, reducing cumbersome or time-consuming processes for viewing visual imaging data for a particular industrial process (e.g., portion thereof) in association synchronized imaging data from other portions of the process, infrared imaging data from particular portions of the process, and representations of process features thereof (e.g., attribute profiles) for various portions of the process. Additional or alternative aspects reduce cumbersome, time-consuming processes for identifying relevant industrial events within the overall process, navigating to different video feeds across the process that may provide insight as to the industrial event, accessing attribute profile data derived from an appropriate portion of the industrial process related to the industrial event, accessing infrared imaging data along with particular imaging data, etc. Such cumbersome processes require the use of arbitrary commands to access each camera feed related to a particular event, at the appropriate time leading up to and subsequent to the event. These problems can be addressed by various user interface features described herein. For instance, a client application can seamlessly integrate imaging data from various sources in association with attribute profiles of process features identified within the imaging data in a single, easy-to-digest interface. A user can provide input (e.g., via the user interface) related to particular feature characteristics of the process and their association with identified industrial events (e.g., breakage events). The input can then be provided as training data for a machine learning model used to predict future breakage vents. Thus, the structure and associated functionality of the interface features described herein can provide improvements in the field of user interface generation and display in addition to improvements in receiving user input usable for training the various machine learning models described herein.

Various aspects of the system provide improved techniques for predicting paper breaks and automating corrective actions before the break occurs. In various aspects, the system comprises any suitable computing system (e.g., any suitable system described herein) such as any computing system suitable for performing the computing functionality described above.

Example Computing Environment

Figure 14:
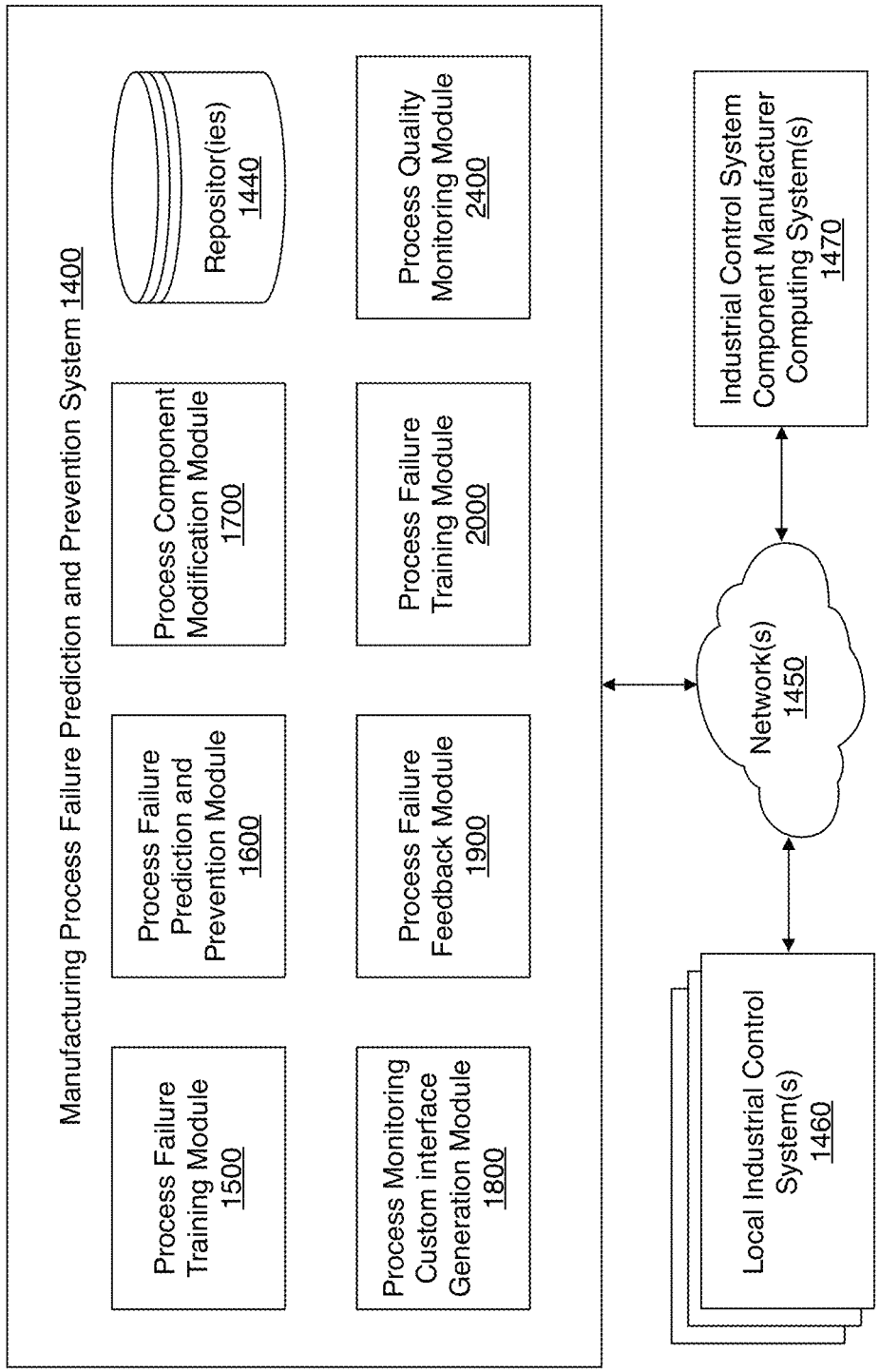
FIG. 14 depicts an example of a computing environment that can be used for predicting manufacturing process failures and implementing preventative actions to prevent the process failures according to various aspects.

FIG. 14 depicts an example of a computing environment that can be used for generating a prediction as to a failure in a manufacturing process and generating (e.g. and facilitating implementation of) a preventative action to prevent the failure.

In various aspects, a manufacturing process failure prediction and prevention system 1400 is provided within the computing environment that includes software components and/or hardware components to generate predictions as to process failures (e.g., identify potential future paper breaks based on various operating parameters and imaging data) and generate a recommendation for preventing or otherwise reducing a likelihood of the failure (e.g., paper break). In some aspects, the manufacturing process failure prediction and prevention system 1400 receives training data form a plurality of local industrial control systems 1460 as those control systems collect failure data and associated data for each failure. For example, local industrial control systems 1460 may record imaging data (e.g., IR image data) for a particular manufacturing process (e.g., paper production line) and provide the imaging data to the manufacturing process failure prediction and prevention system 1400 (e.g., provide imaging data for a time that leads up to and corresponds to an identified paper break or other manufacturing failure). The local industrial control systems 1460 may further record other data related to the failure and provide the data to the manufacturing process failure prediction and prevention system 1400. The manufacturing process failure prediction and prevention system 1400 may then use the data and other data about various failures experienced at a plurality of manufacturing plants (e.g., each of which is operated by and/or monitored by a respective local industrial control system 1460 to train a machine learning model and/or rules-based model for predicting potential future failures (e.g., paper breaks) based on current operating parameters and imaging data at a particular manufacturing plant. The manufacturing process failure prediction and prevention system 1400 may further provide component failure data to an industrial control system component manufacturer computing system 1470 for use in modifying operating parameters (e.g., default operating parameters), redesigning, and/or otherwise improving performance of the component by reducing paper breaks and other manufacturing failures attributable to the component. In various embodiments, each of the manufacturing process failure prediction and prevention system 1400, the local industrial control system(s) 1460 and/or the industrial control system component manufacturer computing system(s) 1470 may communicate via a suitable network 1450.

In some aspects, each of the local industrial control system(s) sharing at least one machine component (e.g., machine type) that produce a particular paper type (e.g., grade, size, etc.) may provide suitable training data.

In some instances, the manufacturing process failure prediction and prevention system 1400 may include one or more repositories 1440 that can be used for storing failure data, sensor data, operating condition data, imaging data, and the like.

In some aspects, the manufacturing process failure prediction and prevention system 1400 executes a process failure training module 1500 to train a machine learning model using historical operational data and manufacturing process failure data (e.g., related to a paper break in a paper manufacturing process). In some aspects, the process failure training module 1500 receives manufacturing process failure data and trains at least one of a machine learning model or rules-based model for a first task of predicting future failures. In other aspects, the process failure training module 1500 receives preventative action success data and uses the preventative action success data to train at least one of a machine learning model or a rules-based model for a second task of generating preventative action recommendations.

In additional or alternative aspects, the manufacturing process failure prediction and prevention system 1400 executes a process failure prediction and prevention module 1600. The process failure prediction and prevention module 1600 receives current imaging data, force data, and profile data for a manufacturing process and uses the imaging data, force data, and profile data to generate a prediction as to a failure in the manufacturing process (e.g., a paper break), for example, using any suitable machine-learning model described herein. The process failure prediction and prevention module 1600 may further identify a preventative action for the predicted failure and facilitate performance of the preventative action.

In additional or alternative aspects, the manufacturing process failure prediction and prevention system 1400 executes a process component modification module 1700. In some aspects, the process component modification module 1700 determines failure data for particular components of a manufacturing process and transmits the failure data to component manufacturer computing systems for use in modifying the component or an operating parameter thereof.

In additional or alternative aspects, the manufacturing process failure prediction and prevention system 1400 executes a process monitoring custom interface generation module 1800. Further detail is provided below regarding the configuration and functionality of the process failure training module 1500, process failure prediction and prevention module 1600, process component modification module 1700, process monitoring custom interface generation module 1800, and process failure feedback module 1900, and process failure training module 2000 according to various aspects of the disclosure.

Process Failure Training Module

Figure 15:
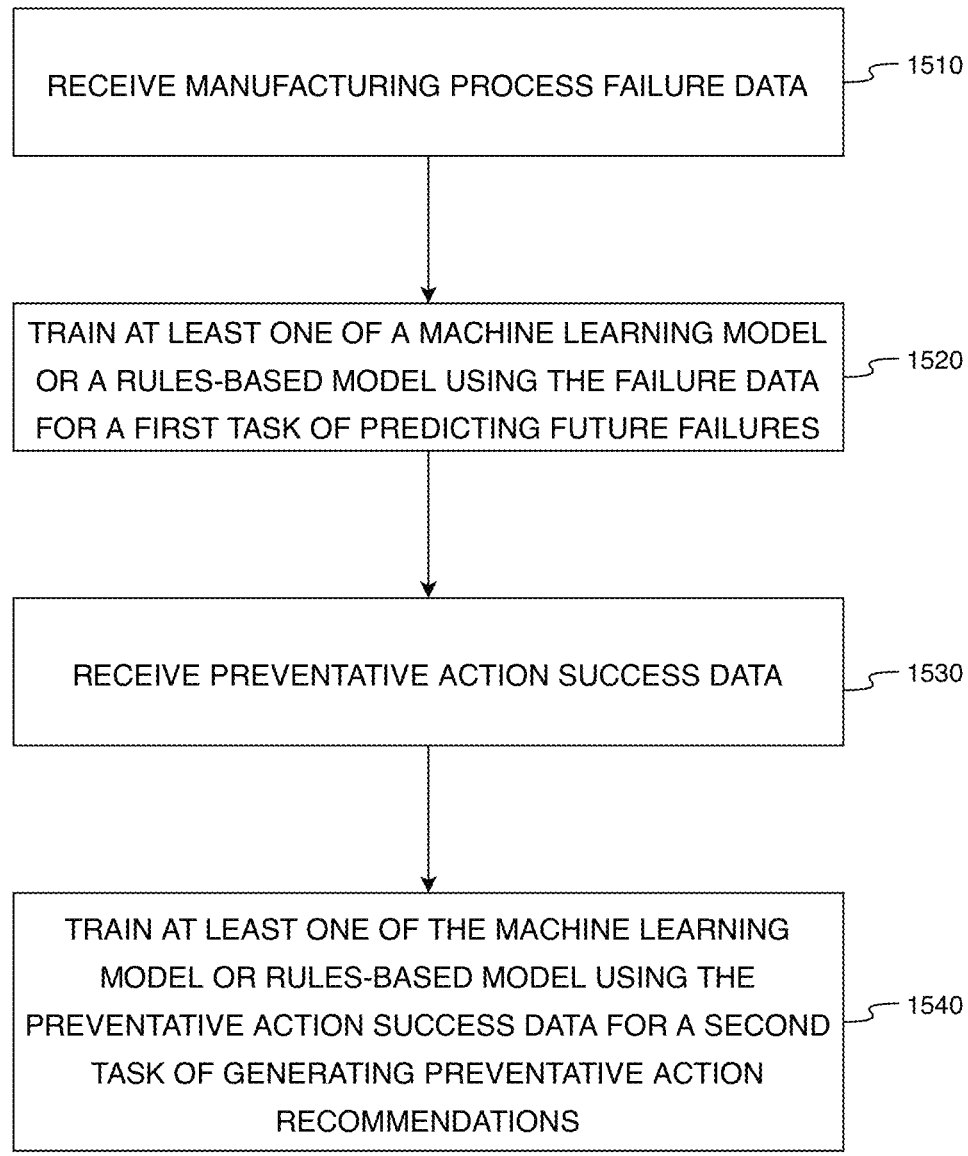
FIG. 15 depicts an example of a process for training a machine learning model to predict manufacturing process failures and generate recommended preventative actions in accordance with various embodiments of the disclosure.

FIG. 15 depicts an example of process performed by a process failure training module 1500. This process include operations that the manufacturing process failure prediction and prevention system 1400 may execute to train a machine learning model using historical operational data and manufacturing process failure data (e.g., related to a paper break in a paper manufacturing process). For instance, the flow diagram shown in FIG. 15 may correspond to operations carried out, for example, by computing hardware found in the manufacturing process failure prediction and prevention system 1400 as the computing hardware executes the process failure training module 1500.

At operation 1510, the process failure training module 1500 receives manufacturing process failure data. In some aspects, the manufacturing process failure prediction and prevention system 1400 receives manufacturing process failure data from each of a plurality of local industrial control systems 1460. For example, each of the plurality of local industrial control systems 1460 may be deployed are various manufacturing plants. Each of the local industrial control systems 1460 may monitor process data and failure data at the respective manufacturing plants and provide the manufacturing process failure data for each respective plant to the manufacturing process failure prediction and prevention system 1400. In this way, the manufacturing process failure prediction and prevention system 1400 may derive training data for the manufacturing process failure prediction and prevention system 1400 from a plurality of data sources, which may, for example, increase an accuracy of the model used to predict potential future manufacturing failure (e.g., paper breaks).

In some aspects, the manufacturing process failure data includes, for example, historical data on prior paper breaks at various paper manufacturing plants as well as material factors, identified wet spots, and other sensor readings leading up to the break. This data may be collected by computing hardware operated by each respective local industrial control system 1460. For example, paper machines (e.g., and other manufacturing equipment) may be equipped with camera systems that helps operators identify the location where the break started and provide an image of a developing break. Often operators may use this information to identify the root cause of the break. For example, if a break is caused by a lump of fiber embedded in paper, one can deduce that the problem is with paper formation. However, in most cases operators can identify the type of defect but not the root cause. Often, defect identification often occurs after a break occurs. As such, it can be technically challenging to identify potential breaks prior to them occurring, in order to reduce paper machine downtime.

Various aspects of the systems describe herein comprise visual and infrared cameras that may be configured to predict the probability of a break based on the camera input. In general, the prediction may include a prediction as to whether a sheet break may occur when paper is not strong enough to withstand forces exerted by a particular paper machine. For example, a wet spot detected by an IR camera in otherwise dry paper may create a weak spot which can turn into a hole or an edge crack, depending on the wet spot location, and this can happen even if the forces exerted on the paper web are within normal operating conditions. As such, the system may use one or more IR cameras to identify wet spots in order to generate a prediction as to a likelihood of a sheet break based on a position of the wet spot, size of the wet spot, etc. Alternatively, a defect free paper web subjected to excessive forces in a particular paper machine location may exceed what the paper web can withstand and result in a sheet break. Additionally, a combination of weak spots and excessive forces may result in a high probability that a sheet break will occur.

In particular embodiments, the system is configured to analyze and process video from one or more visual cameras to determine amplitudes and frequencies of the paper web movements caused by the forces of the paper machine process. For example, by measuring the amplitudes and frequencies of a press release point, the system can analyze the dynamic forces impacting the web at the press location and identify the machine components that produce forces at a given frequency. The same approach may apply to paper edge and dry line movements, along with many other parameters measurable by one or more imaging devices. Therefore, being able to track frequencies and amplitudes in real time may provide data for generating a prediction as to which point the paper is likely to break may allow the system to predict sheet breaks caused by undue forces.

The system may use LWIR (long wave infrared) cameras to generate heat maps that represent paper web temperature distribution. Since paper temperature is proportional to paper moisture content temperature data can be used to generate a prediction as to whether a particular sheet may break (e.g., due to a wet spot). This is because the paper strength depends mainly on the inter-fiber bonding which, when disrupted by water immersion, may leave only about 2-3% of the dry tensile strength. In some aspects, the system is configured to derive moisture data for the paper web using any suitable technique described herein.

Accordingly, the system 1400 may receive paper web moisture data as well as vibrational and force data in addition to incident data for particular paper breaks. The system 1400 may then use this data as training data for at least one of a machine-learning model or a rules-based model for performing a task of predicting a future break based on prior paper break data and associated paper data.

At operation 1520, the process failure training module 1500 trains at least one of a machine-learning model or a rules-based model using the failure data for a first task of predicting future failures (e.g., before the failures occur). In various aspects, the machine learning model may be trained using historical data on paper break events and associated data for each event (e.g., moisture, vibration, and other data). Accordingly, the machine learning model may be configured using a variety of different types of supervised or unsupervised trained models such as, for example, support vector machine, naive Bayes, decision tree, neural network, and/or the like.

At operation 1530, the process failure training module 1500 receives preventative action success data. In some aspects, the manufacturing process failure prediction and prevention system 1400 receives, for each identified failure event in the training data, a preventative action data for each preventative action taken prior to the failure event. The system may also receive preventative action data for potential failures predicted by the system (e.g., preventative actions taken prior to the failure occurring, when the other modules discussed herein have predicted a potential future paper break (e.g., failure event). The preventative action success data may include data regarding whether the predicted event occurred following the preventative action (i.e., which may provide success information for the preventative action).

At operation 1540, the manufacturing process failure prediction and prevention system 1400 trains the at least one of the machine learning model or the rules-based model using the preventative action success data for a second task of generating preventative action recommendations based on identified potential future failures (e.g., predicted paper breaks). In various aspects, the machine learning model may be trained using historical data on paper break prevention success each event (e.g., what action was taken for a predicted failure, and how effective the action was at preventing the failure). Accordingly, the machine learning model may be configured using a variety of different types of supervised or unsupervised trained models such as, for example, support vector machine, naive Bayes, decision tree, neural network, and/or the like. In various embodiments, the system may train multiple machine learning models, rather than training the same model for different tasks.

For illustrative purposes, the process failure training module 1500 is described with reference to implementations described above with respect to one or more examples described herein. Other implementations, however, are possible. In some aspects, the steps in FIG. 15 may be implemented in program code that is executed by one or more computing devices such as any suitable device or combination of devices described herein. In some aspects, one or more operations shown in FIG. 15 may be omitted or performed in a different order. Similarly, additional operations not shown in FIG. 15 may be performed.

Process Failure Prediction and Prevention Module

Figure 16:
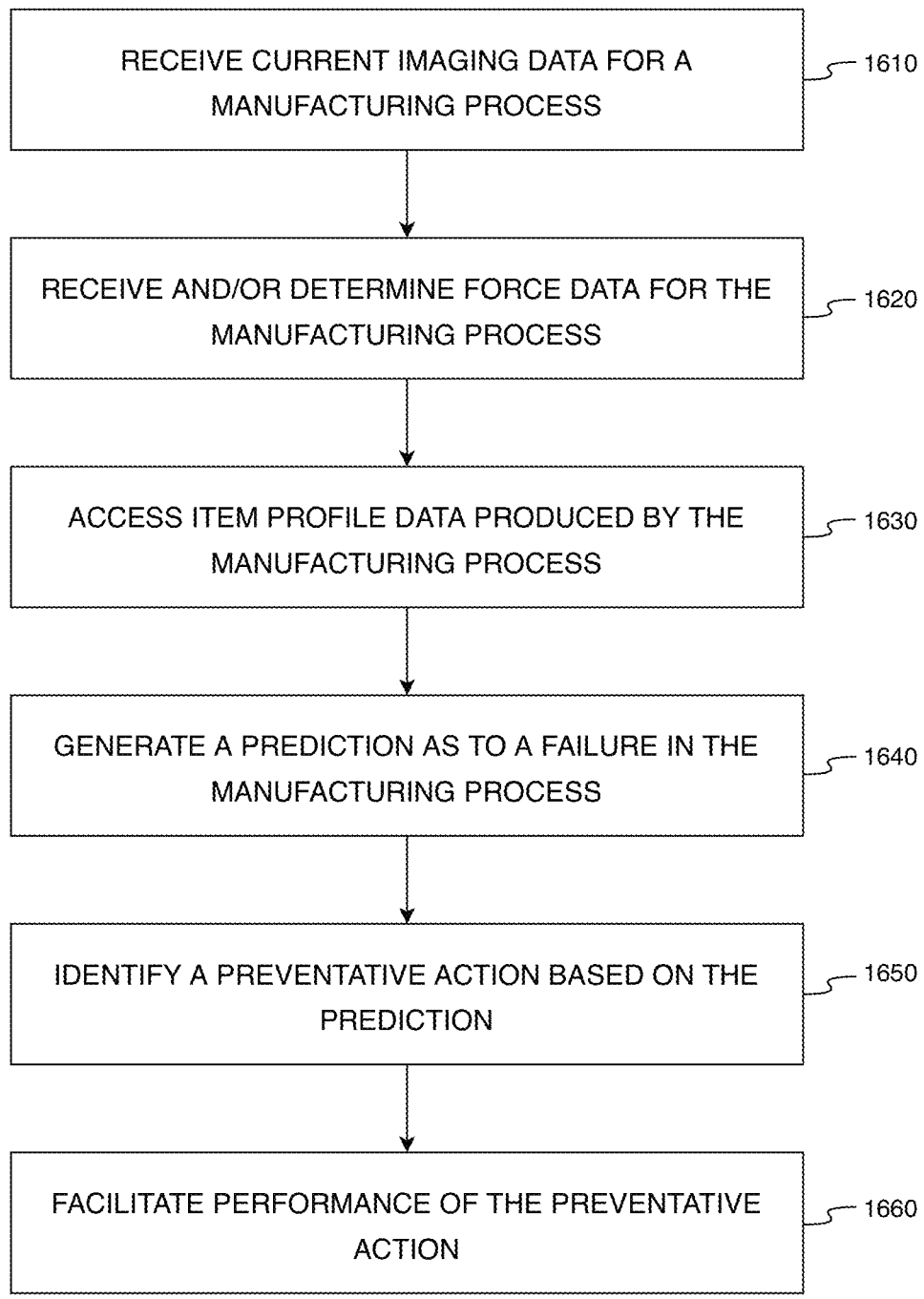
FIG. 16 depicts an example of a process for predicting manufacturing process failures and generating and implementing recommended preventative actions in accordance with various embodiments of the disclosure.

FIG. 16 depicts an example of process performed by a process failure prediction and prevention module 1600. This process include operations that the manufacturing process failure prediction and prevention system 1400 may execute to generate a prediction as to a failure in the manufacturing process (e.g., a paper break), for example, using any suitable machine-learning model described herein. The process failure prediction and prevention module 1600 may further identify a preventative action for the predicted failure and facilitate performance of the preventative action. For instance, the flow diagram shown in FIG. 16 may correspond to operations carried out, for example, by computing hardware found in the manufacturing process failure prediction and prevention system 1400 (e.g., or other suitable system) as the computing hardware executes the process failure prediction and prevention module 1600. In some aspects, the process failure prediction and prevention module 1600 is executed by a computing system other than the manufacturing process failure prediction and prevention system 1400 (e.g., a computing system other than the computing system that executes the process failure training module 1500).

At operation 1610, the manufacturing process failure prediction and prevention system 1400 (e.g., or other system) receives current imaging data for a manufacturing process. In various embodiments, the imaging data may be used to identify moisture content on various portions of a paper web in a paper manufacturing line. For example, the imaging data may include thermal mapping data. The process may involve mapping the temperature profile to a correlated moisture profile representing a moisture distribution across the paper web. For example, a wet spot detected by an IR camera in otherwise dry paper may create a weak spot which can turn into a hole or an edge crack, depending on the wet spot location, and this can happen even if the forces exerted on the paper web are within normal operating conditions. As such, the system may use one or more IR cameras to identify wet spots in order to generate a prediction as to a likelihood of a sheet break based on a position of the wet spot, size of the wet spot, etc.

Next, at operation 1620, the manufacturing process failure prediction and prevention system 1400 receives and/or determines force data for the manufacturing process. In particular embodiments, the system is configured to analyze and process video from one or more visual cameras to determine amplitudes and frequencies of the paper web movements caused by the forces of the paper machine process. For example, by measuring the amplitudes and frequencies of a press release point, the system can analyze the dynamic forces impacting the web at the press location and identify the machine components that produce forces at a given frequency. The same approach may apply to paper edge and dry line movements, along with many other parameters measurable by one or more imaging devices. Therefore, being able to track frequencies and amplitudes in real time may provide data for generating a prediction as to which point the paper is likely to break may allow the system to predict sheet breaks caused by undue forces. In other aspects, the system may determine force data for various components of the process and the paper web itself using any suitable technique described herein.

At operation 1630, the manufacturing process failure prediction and prevention system 1400 accesses item profile data produced by the manufacturing process. For example, the manufacturing process failure prediction and prevention system 1400 may access paper thickness, paper weight, and other physical property data for the paper or other article being manufactured.

At operation 1640, the manufacturing process failure prediction and prevention system 1400 generates a prediction as to a failure in the manufacturing process. In some aspects, generating the prediction involves causing a machine learning model to generate the prediction.

In various aspects, the system 1400 may process the heat maps, identified moisture locations, moisture size and shape, and amplitude and frequencies of paper web movement using a rules-based model, a machine-learning model, or both to generate a prediction as to a likelihood of a break. For example, the rules-based model, machine learning model, or combination of both may be configured to process the heat maps, identified, moisture locations, moisture size and shape, amplitude and frequencies of paper web movement, and/or the like in determining the likelihood that a particular break will occur in a particular location. For example, the rules-based model, machine learning model, or combination of both may be configured to generate a prediction based on the location of a wet spot, current vibration levels, etc.

For example, according to particular aspects, the system may use a rules-based model to generate the prediction. The rules-based model may comprise a set of rules that assigns respective breakage risks to each of a plurality of paper factors (e.g., paper grade, identified wet spot location etc.). For example, the set of rules may define one or more rules for assigning impact values based on material type, manufacturing process, etc. Accordingly, the system may maintain the set of rules in some type of data storage, from which the system can access the set of rules for generating the prediction as to the likelihood of a break.

According to other aspects, system may utilize a machine learning model in generating the prediction (or identifying a potential and/or likely break). Here, the machine learning model may be trained using historical data on prior breaks and material factors, identified wet spots, and other sensor readings leading up to the break. In various aspects, the training data may be derived from a plurality of industrial systems across plurality of locations. Accordingly, the machine learning model may be configured using a variety of different types of supervised or unsupervised trained models such as, for example, support vector machine, naive Bayes, decision tree, neural network, and/or the like.

In particular embodiments, the system may implement one or more neural networks to perform any of the big data processing techniques described herein. A neural network, according to various embodiments, comprises: (1) a plurality of nodes that mimic the operation of the human brain; (2) a training mechanism that analyzes supplied information, and (3) a paper break prediction engine for predicting a potential breakage. In various embodiments, each of the nodes comprises one or more weighted input connections, at least one transfer function that combines the inputs, and an output connection. In particular embodiments, the neural network is a variational AE neural network, a denoising AE neural network, or any other suitable neural network.

In various embodiments, the machine learning model and/or neural network may utilize one or more of: (1) frequencies and amplitudes of paper machine components (representing the forces exerted on the paper); (2) detected weak spots (representing paper vulnerabilities); (3) paper machine speed; (4) manufactured paper grade; (5) any other paper machine parameter pertaining to machine runnability; and/or (6) any other suitable factors. In some aspects, the system may use these factors as inputs related to predicting paper breaks. In particular aspects, the training data may enable the neural network and/or other machine learning model to apply identified relationships between the forces exerted on the paper, paper vulnerabilities, and the sheet breaks to identify future sheet breaks before they occur. Applying these operations, the system may determine the probability of a sheet break for the current paper machine conditions and alert the operator or take a prescribed corrective action.

At operation 1650, the manufacturing process failure prediction and prevention system 1400 identifies a preventative action based on the prediction. In some aspects, identifying the preventative action may involve causing a machine learning model to generate a recommendation as to a preventative action to take to rectify and/or prevent the predicted failure (e.g., paper break). In some aspects, the system may analyze past preventative action success data to identify particular preventative actions that have prevented prior predicted breaks. The system may then correlate particular actions with successful breakage prevention to generate a recommendation as to a preventative action for a particular predicted break (e.g., based on the break type, location, machine components involved, etc.).

At operation 1660, the manufacturing process failure prediction and prevention system 1400 facilitates performance of the preventative action. In some aspects, facilitate performance of the preventative action may include modifying one or more operating parameters of the manufacturing process. This may include, for example, modifying a motor speed of one or more components, modifying a feed rate, etc. In other aspects, facilitating performance of the preventative action may include initiating a cleaning process for one or more components of the manufacturing process. In still other aspects, facilitating the preventative action may include generating one or more alarms, alerts, or the like for notifying one or more plant operators of the potential failure (e.g., paper break).

In some aspects, in response to identifying a potential sheet break, the system is configured to automate a response. In some aspects, the automated response may include one or more of: (1) triggering an alarm; (2) stopping a paper machine; (3) modifying an operating speed of at least one paper machine component; (4) reducing pressure on one or more machine components (e.g., rolls); (5) washing one or more felt components; and (6) etc. In other aspects, the system may implement (e.g., cause implementation of) any suitable preventative action which may at least lessen a likelihood that a predicted break will occur.

For illustrative purposes, the process failure prediction and prevention module 1600 is described with reference to implementations described above with respect to one or more examples described herein. Other implementations, however, are possible. In some aspects, the steps in FIG. 16 may be implemented in program code that is executed by one or more computing devices such as any suitable device or combination of devices described herein. In some aspects, one or more operations shown in FIG. 16 may be omitted or performed in a different order. Similarly, additional operations not shown in FIG. 16 may be performed.

Process Component Modification Module

Figure 17:
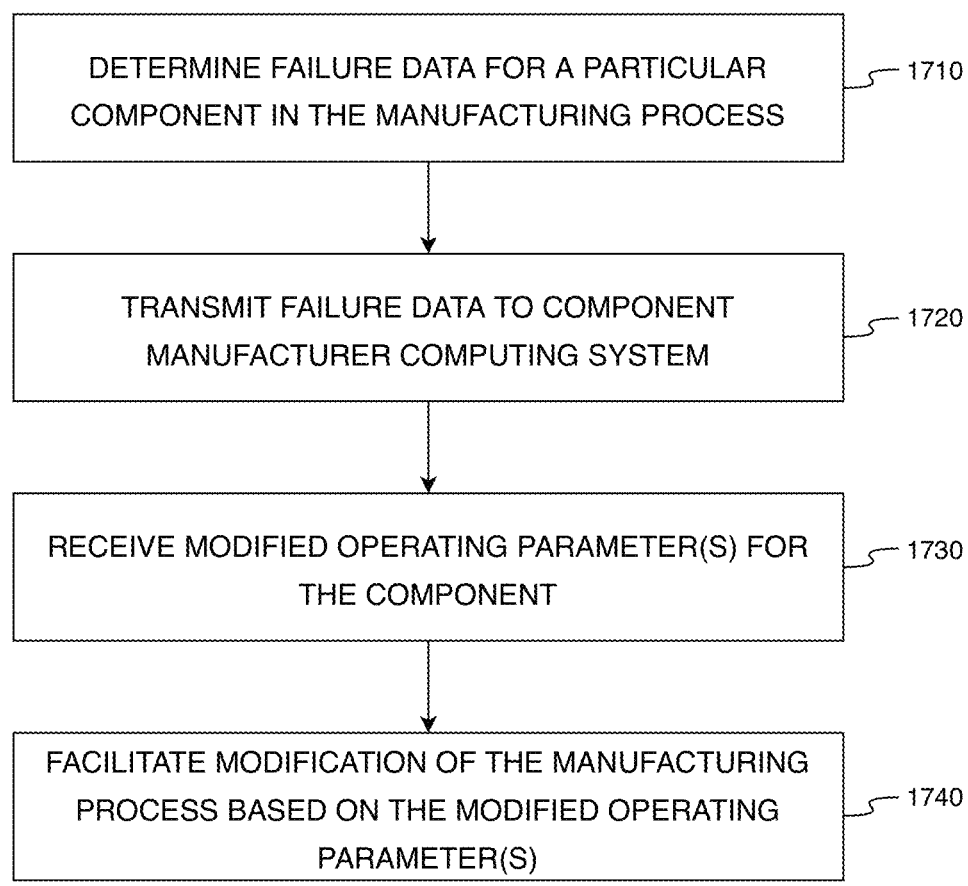
FIG. 17 depicts an example of a process for modifying manufacturing process components and/or operating parameters in accordance with various embodiments of the disclosure.

FIG. 17 depicts an example of process performed by a process component modification module 1700. This process include operations that the manufacturing process failure prediction and prevention system 1400 may execute to determine failure data for particular components of a manufacturing process and transmits the failure data to component manufacturer computing systems for use in modifying the component or an operating parameter thereof. For instance, the flow diagram shown in FIG. 17 may correspond to operations carried out, for example, by computing hardware found in the manufacturing process failure prediction and prevention system 1400 as the computing hardware executes the process component modification module 1700. In other aspects, the operations may be carried out by computing hardware found in the industrial control system component manufacturer computing system(s) 1470.

At operation 1710, the process component modification module 1700 determines failure data for a particular component in the manufacturing process. The system may, for example, identify a component that would have been the root of a predicted break should it occur.

At operation 1720, the process component modification module 1700 transmits failure data to a component manufacture computing system (e.g., industrial control system component manufacturer computing system 1470). The system may, for example identify a manufacturer of one or more components involved in a predicted break and transmit the prediction data to a computing system associated with each component manufacture. In some aspects, the manufacturers may identify weak points in the machine to provide feedback for potential re-designs of equipment to reduce an instance of paper breakage on a particular machine. In particular aspects, the manufacturer may identify modified operating parameters for components that may reduce potential breaks (e.g., reducing default operating speed, modifying cleaning schedule, etc.). The manufacturing computing system may then transmit the modified operation parameters for local industrial control systems 1460 for implementation at their respective processing plants. In some aspects, the system comprises a communications network accessible by different industrial control systems at different plant locations. In various embodiments, the communications network is configured to share historical data regarding breakage and associated imaging data, sensor measurements, etc.

At operation 1730, the process component modification module 1700 receives modified operating parameter(s) for the components 1730. Then, at operation 1740, the process component modification module 1700 facilitates modification of the manufacturing process based on the modified operating parameters(s). For example, the process component modification module 1700 may distribute the modified operating parameters for implementation at each of a plurality of local industrial control systems 1460 that operate respective instances of the manufacturing process (e.g., papermaking process or other industrial control process). In this way, a component manufacturer may redesign or reconfigure particular components using data provided by the system 1400 in order to improve the performance of that component within the process.

For illustrative purposes, the process component modification module 1700 is described with reference to implementations described above with respect to one or more examples described herein. Other implementations, however, are possible. In some aspects, the steps in FIG. 17 may be implemented in program code that is executed by one or more computing devices such as any suitable device or combination of devices described herein. In some aspects, one or more operations shown in FIG. 17 may be omitted or performed in a different order. Similarly, additional operations not shown in FIG. 17 may be performed.

Process Monitoring Custom Interface Generation Module

Figure 18:
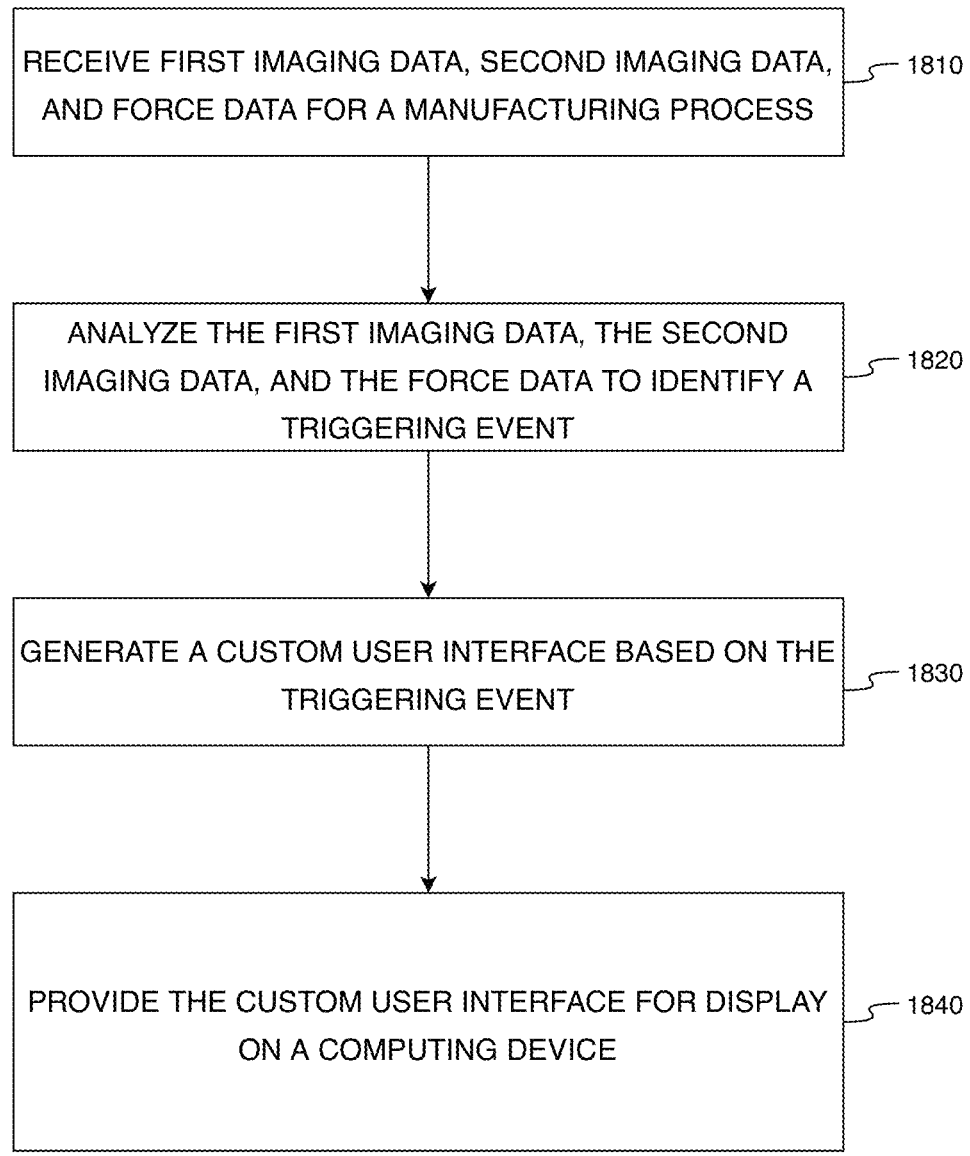
FIG. 18 depicts an example of a process for generating custom interfaces related to manufacturing processes and manufacturing process failures in accordance with various embodiments of the disclosure.

FIG. 18 depicts an example of process performed by a process monitoring custom interface generation module 1800. This process include operations that the manufacturing process failure prediction and prevention system 1400 may execute to generate and display imaging data and related analysis related to a particular industrial process (e.g., related to a paper break in a paper manufacturing process). For instance, the flow diagram shown in FIG. 18 may correspond to operations carried out, for example, by computing hardware found in the manufacturing process failure prediction and prevention system 1400 as the computing hardware executes the process monitoring custom interface generation module 1800.

At operation 1810, the process monitoring custom interface generation module 1800 receives first imaging data, second imaging data, and force data for a manufacturing or industrial process. In particular embodiments, the first imaging data may include visual imaging data (e.g., video) from one or more cameras positioned along an industrial process. In various embodiments, the second imaging data may be used to identify moisture content on various portions of a paper web in a paper manufacturing line (or other component of a manufacturing or industrial process). For example, the imaging data may include thermal mapping data. The process may involve mapping the temperature profile to a correlated moisture profile representing a moisture distribution across the paper web. For example, a wet spot detected by an IR camera in otherwise dry paper may create a weak spot which can turn into a hole or an edge crack, depending on the wet spot location, and this can happen even if the forces exerted on the paper web are within normal operating conditions. As such, the system may use one or more IR cameras to identify wet spots in order to generate user interfaces that include the infrared imaging and/or moisture data to enable an operator to ascertain a cause of a paper break, and provide the identified cause as training data for a machine learning model (e.g., any model described herein). The system may further receive and/or determine force data for the manufacturing process. In particular embodiments, the system is configured to analyze and process video from one or more visual cameras to determine amplitudes and frequencies of the paper web movements caused by the forces of the paper machine process. For example, by measuring the amplitudes and frequencies of a press release point, the system can analyze the dynamic forces impacting the web at the press location and identify the machine components that produce forces at a given frequency. The same approach may apply to paper edge and dry line movements, along with many other parameters measurable by one or more imaging devices. Therefore, being able to track frequencies and amplitudes in real time may provide data for may enable the system to generate visual representations of the force data for inclusion in the user interfaces described herein. In other aspects, the system may determine force data for various components of the process and the paper web itself using any suitable technique described herein.

In some aspects, at operation 1820, the system analyzes the data to identify a triggering event. In some aspects, the triggering event may include any suitable event such as a paper breakage event. In various aspects, the user interface generation process described herein may include providing a substantially current view of a manufacturing process. In other aspects, the system may be configured to generate custom interfaces that provide imaging and other data around the identified triggering event (e.g., moisture data leading up to the triggering event, attribute data leading up to the triggering event, imaging data leading up to and at the triggering event, etc.). In this way, a user may review the custom interface for a particular event to easily review all relevant data (i.e., both visible and invisible to the human eye) in order to ascertain a cause of the event (e.g., and provide the cause as training data in a machine learning model as described herein).

At operation 1830, the system generates a custom user interface based on the triggering event. For example, in various aspects, the system generates a custom interface that includes at least one image of the industrial process and a visual representation of a data structure representing an attribute array described herein. In other aspects, the custom interface incorporates infrared imaging data to provide moisture content for a portion of a paper web in association with the attribute array data. In this way, the custom interface enables a user to easily review data leading up to a triggering event in order to ascertain a cause of the event based on the data.

Figure 26:
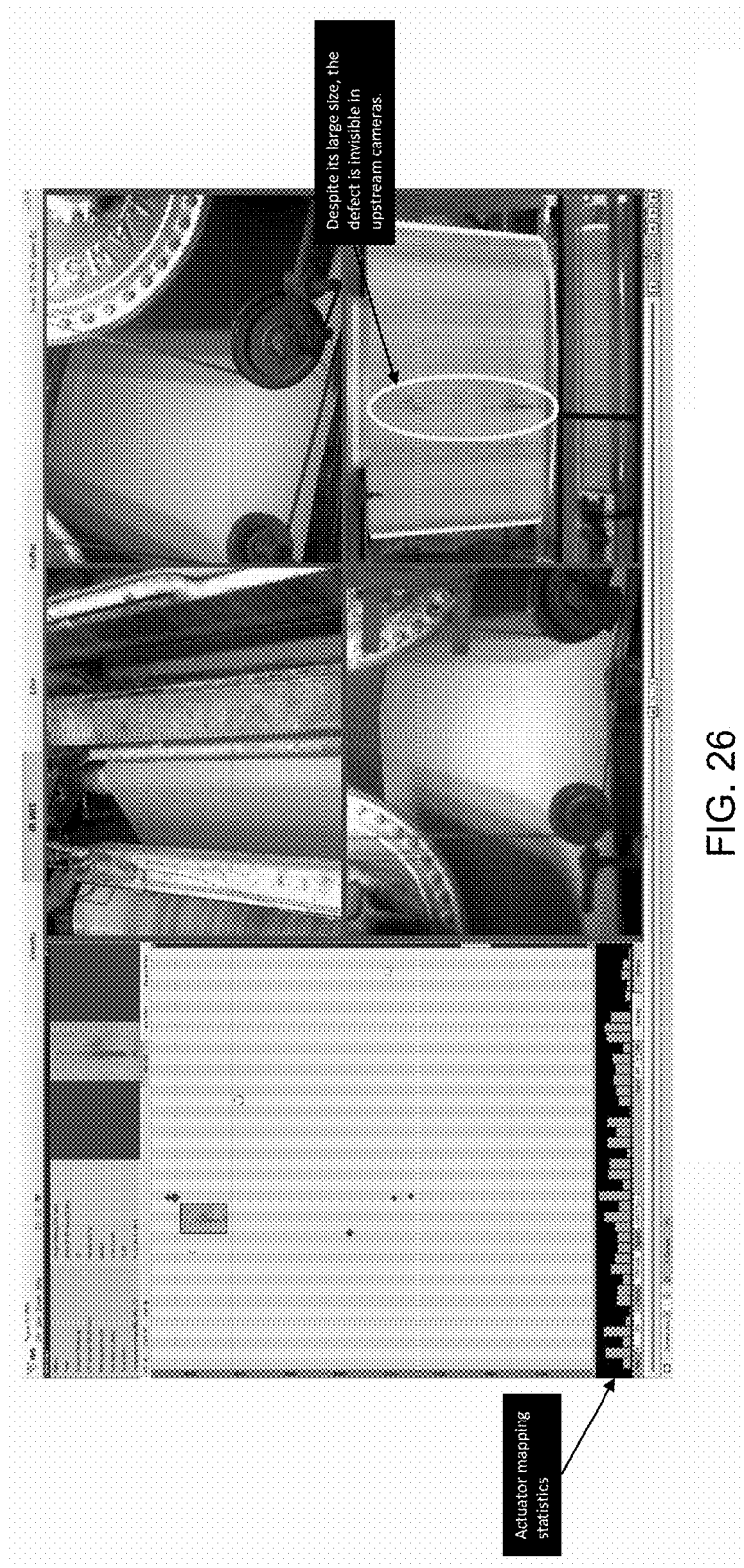
FIG. 26 depicts an exemplary user interface that a use may encounter in the context of various aspects of the present system.

In some aspects, the system may be configured to correlate infrared and visual imaging data. For example, the system may identify a defect (e.g., spot, streak, etc.) in a particular location on a paper web and automatically provide a visual image of the same area (e.g., by automatically cropping the visual image to the same portion of the paper web on which the defect has been identified via infrared imaging). FIG. 26 depicts an interface showing both visual and infrared imaging on a portion of paper web (e.g., with an identified portion with an invisible-to-the-eye defect that is visible on the IR image).

As may be understood in light of this disclosure, the attribute profiles may have either a linear or a non-linear correlation to mapped profiles of measurements for one or more properties used by the entity in controlling the one or more processing parameters of an industrial process. For example, a brightness profile extracted from brightness values from a set of pixels found in media recorded of a paper web using a video camera may correlate to a profile of thickness measurements normally generated by a caliber gauge during manufacturing of paper. Likewise, a temperature profile may be generated from extracting temperature values from a set of pixels found in media recorded of the paper web using an infrared camera that may correlate to a profile of moisture measurements normally taken by a moisture sensor during manufacturing of paper. Accordingly, the one or more attribute profiles generated from the set of pixels can be mapped to profiles (referred to as mapped profiles) of the properties used in controlling the one or more processing parameters of the industrial process. Visual representations of these profiles may then be incorporated into the custom interfaces described herein.

Figure 21:
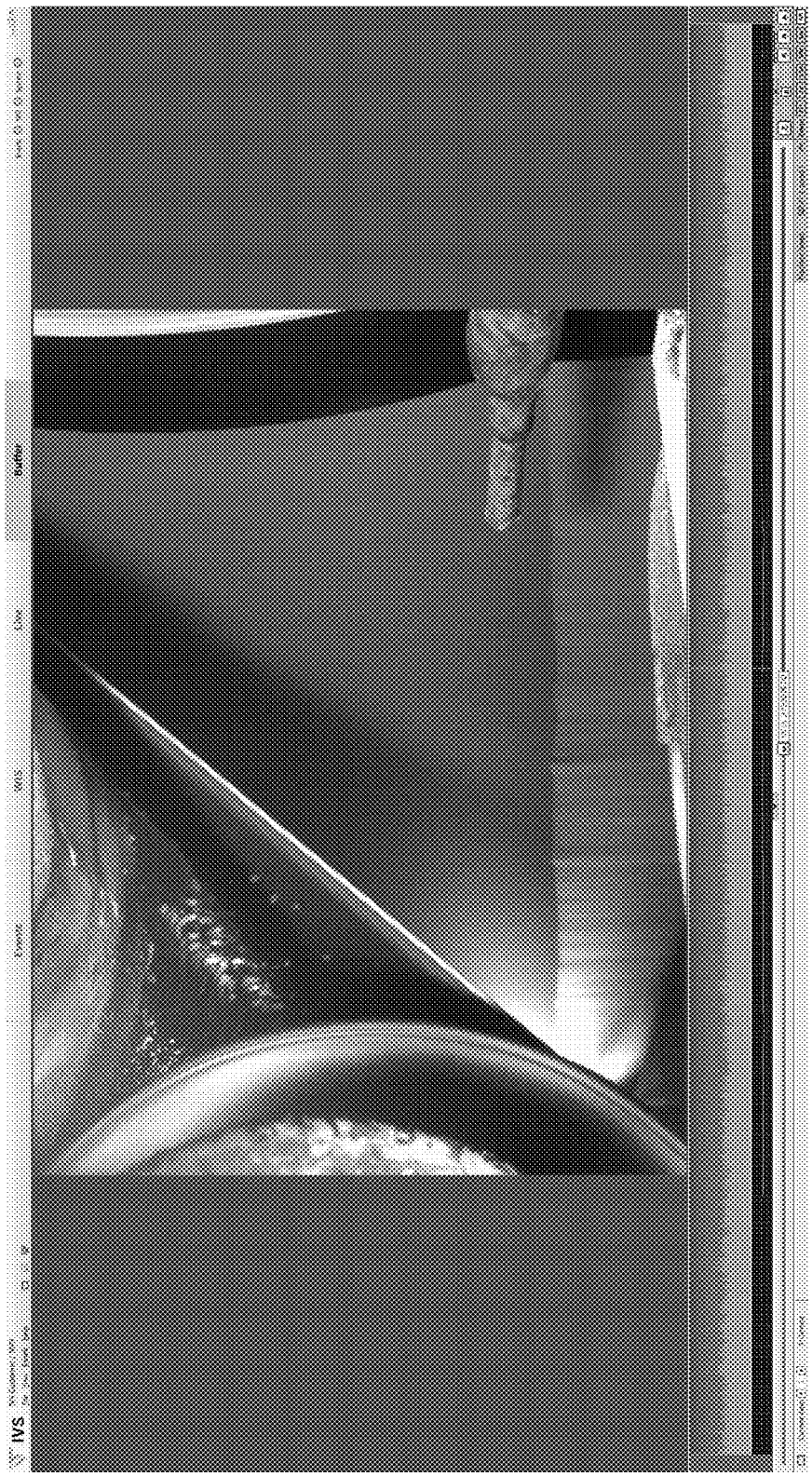
FIGS. 21-23 depict exemplary user interfaces that a use may encounter in the context of various aspects of the present system.
Figure 22:
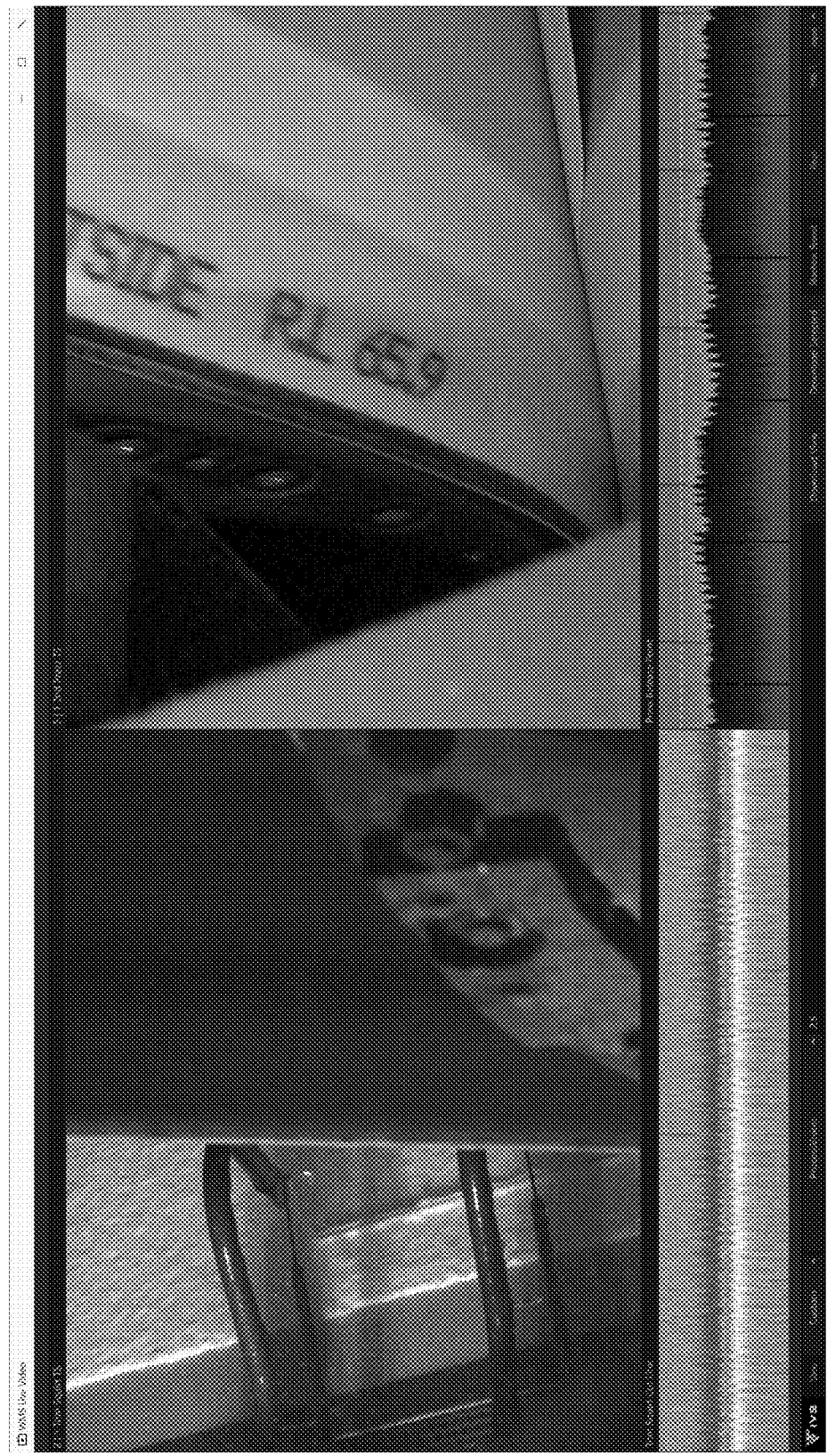
Figure 23:
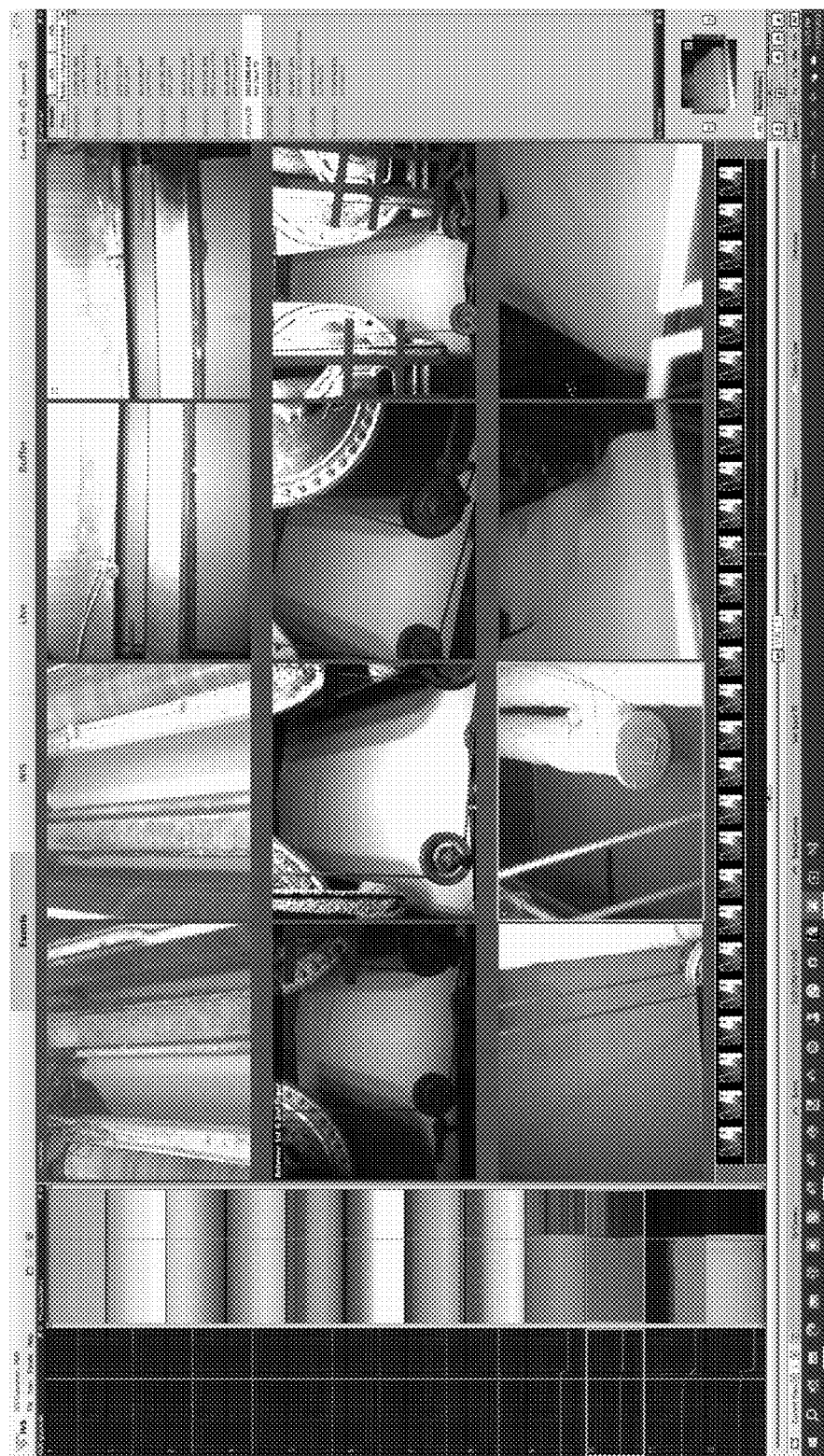

FIGS. 21-23 depict exemplary use interfaces that a user may encounter when accessing the custom user interfaces described herein. FIG. 21 depicts a representation of a paper roll release point (e.g., a video image of the release point) along with position and frequency measurements for the release point. By margining this data into a single interface, a user can easily view data related to the release point around a time of a triggering event that occurs in the field of view of the camera (e.g. and identify a cause of the triggering event in order to provide the cause as training data to any machine learning model described herein). FIG. 22 depicts an exemplary interface that includes an alarm in response to identification of a triggering event. In various aspects, the system may generate these custom interfaces in response to identified triggering events (e.g., in response to identifying operating parameters outside of a predefined limit) to facilitate easy review by an operator. FIG. 23 depicts a user interface that includes multiple synchronized video feeds in addition to infrared data and attribute profiles over time for a particular section of a paper web. By incorporating all of the data in one screen, the system may facilitate a straightforward identification, by a view of the interface, of a cause of a particular event. The user may then provide the identified cause as feedback for use as training data to a machine learning model.

Returning to FIG. 18, at operation 1840, the system provides the custom user interface for display on a computing device.

For illustrative purposes, the process monitoring custom interface generation module 1800 is described with reference to implementations described above with respect to one or more examples described herein. Other implementations, however, are possible. In some aspects, the steps in FIG. 18 may be implemented in program code that is executed by one or more computing devices such as any suitable device or combination of devices described herein. In some aspects, one or more operations shown in FIG. 18 may be omitted or performed in a different order. Similarly, additional operations not shown in FIG. 18 may be performed.

Process Failure Feedback Module

Figure 19:
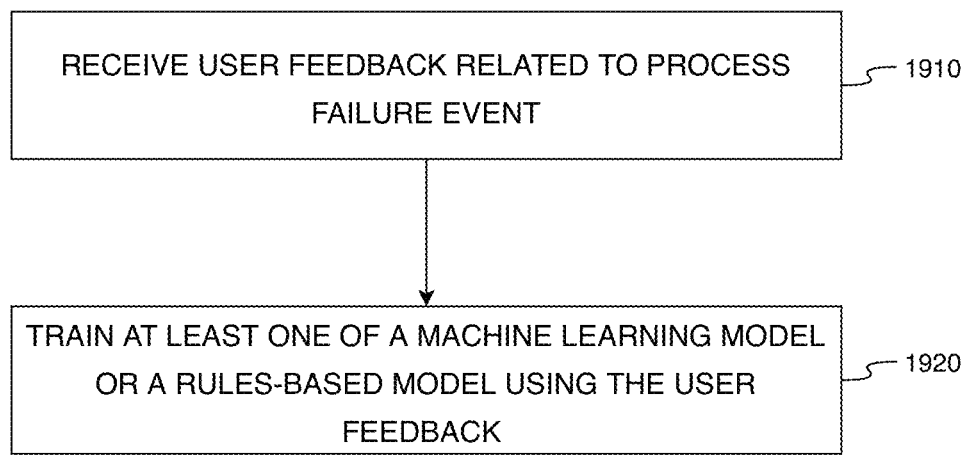
FIG. 19 depicts an example of a process for providing training data to train a machine learning model to predict manufacturing process in accordance with various embodiments of the disclosure.

FIG. 19 depicts an example of process performed by a process failure feedback module 1900. This process include operations that the manufacturing process failure prediction and prevention system 1400 may execute to receive feedback related to an identified process failure event, and provide the feedback as training data to a machine learning model for predicting future failure events. For instance, the flow diagram shown in FIG. 19 may correspond to operations carried out, for example, by computing hardware found in the manufacturing process failure prediction and prevention system 1400 as the computing hardware executes the process failure feedback module 1900.

At operation 1910, the process failure feedback module 1900 receives user feedback related to a process failure event. In some aspect, the feedback may include an identified cause of a particular event (e.g., paper breakage event) identified by the user by reviewing the interfaces described herein.

At operation 1920, the process failure feedback module 1900 trains at least one of a machine learning model or a rules-based model using the user feedback.

For illustrative purposes, the process failure feedback module 1900 is described with reference to implementations described above with respect to one or more examples described herein. Other implementations, however, are possible. In some aspects, the steps in FIG. 19 may be implemented in program code that is executed by one or more computing devices such as any suitable device or combination of devices described herein. In some aspects, one or more operations shown in FIG. 19 may be omitted or performed in a different order. Similarly, additional operations not shown in FIG. 19 may be performed.

Process Failure Training Module

Figure 20:
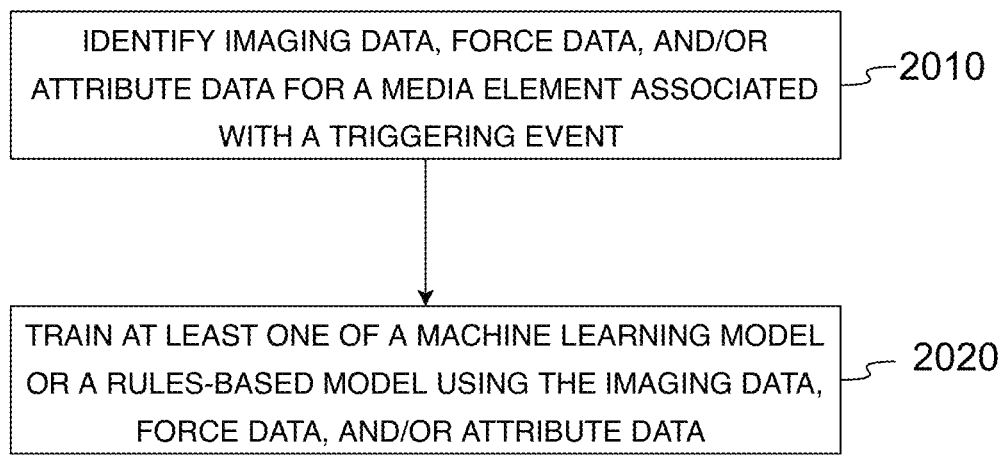
FIG. 20 depicts an example of a process for training a machine learning model to predict manufacturing process failures in accordance with various embodiments of the disclosure.

FIG. 20 depicts an example of process performed by a process failure training module 2000. This process includes operations that the manufacturing process failure prediction and prevention system 1400 may execute to providing imaging and other data related to an identified training event as training data to a machine learning model for predicting future failure events. For instance, the flow diagram shown in FIG. 20 may correspond to operations carried out, for example, by computing hardware found in the manufacturing process failure prediction and prevention system 1400 as the computing hardware executes the process failure training module 20000.

At operation 2010, the process failure training module 2000 identifies imaging data, force data, and/or attribute data for a media element associated with a triggering event related to a process failure event. In some aspects, the system identifies the imaging data, force data, and/or attribute data by identifying such data used in generating the custom interface via which a user identified a cause of the event.

At operation 2020, the process failure training module 2000 trains at least one of a machine learning model or a rules-based model imaging data, force data, and/or attribute data. In this way, the system may enable the machine learning and/or rules-based model to identify future breaks before they occur, by correlating the data utilized by a user in ascertaining an event cause with the actual event.

For illustrative purposes, the process failure training module 2000 is described with reference to implementations described above with respect to one or more examples described herein. Other implementations, however, are possible. In some aspects, the steps in FIG. 20 may be implemented in program code that is executed by one or more computing devices such as any suitable device or combination of devices described herein. In some aspects, one or more operations shown in FIG. 20 may be omitted or performed in a different order. Similarly, additional operations not shown in FIG. 20 may be performed.

Process Component Modification Module

Figure 24:
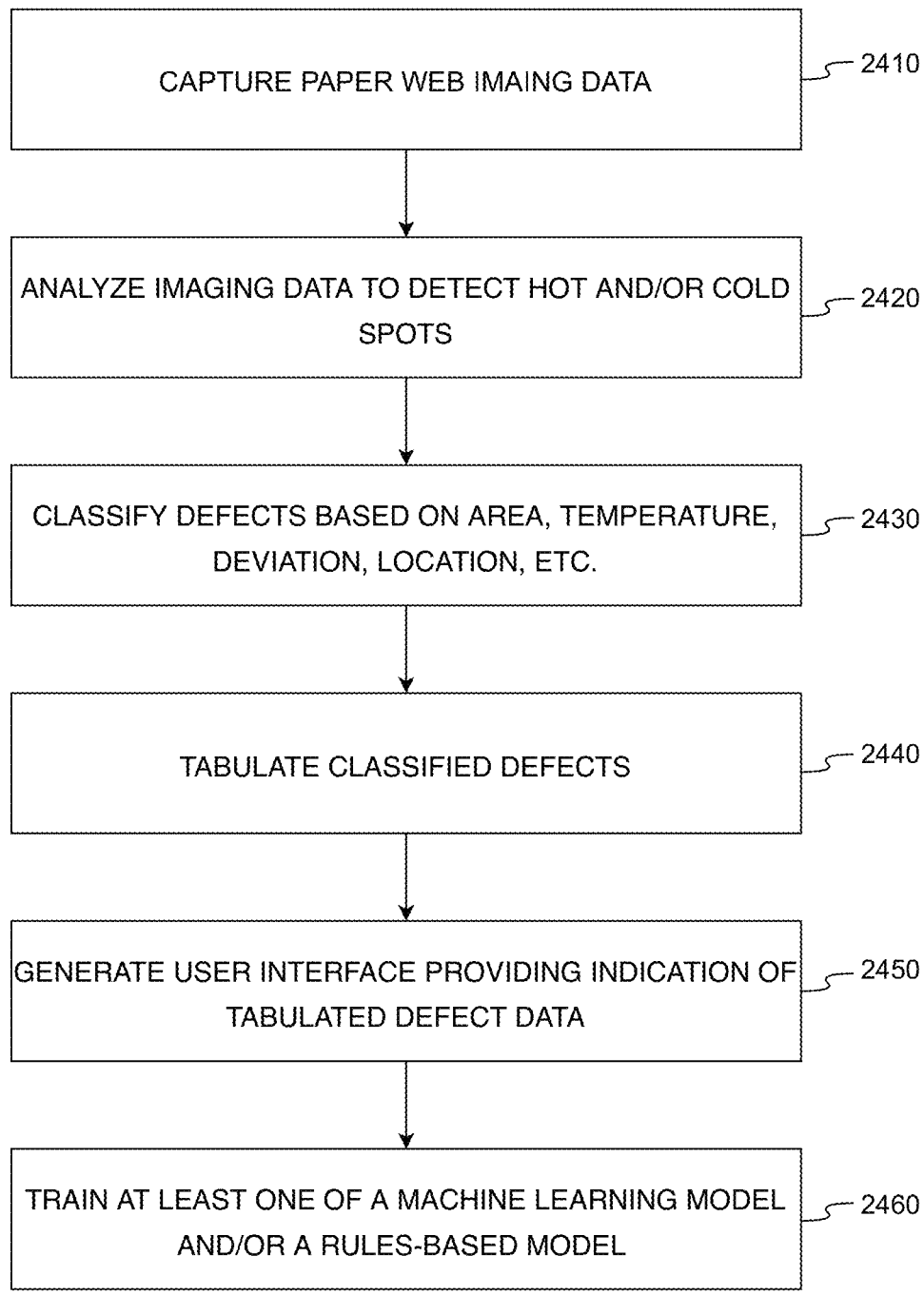
FIG. 24 depicts an example of a process for monitoring the quality of a product produced by a manufacturing process in accordance with various embodiments of the disclosure.

FIG. 24 depicts an example of process performed by a process quality monitoring module 2400. This process include operations that the manufacturing process failure prediction and prevention system 1400 may execute to monitor the quality of an industrial process. For example, the process may monitor the article of manufacture (e.g., paper) produced from the process to determine that the article meets and/or exceeds one or more quality requirements related to the process. For instance, the flow diagram shown in FIG. 24 may correspond to operations carried out, for example, by computing hardware found in the manufacturing process failure prediction and prevention system 1400 as the computing hardware executes the process quality monitoring module 2400. In other aspects, the operations may be carried out by computing hardware found in the industrial control system component manufacturer computing system(s) 1470.

In some aspects, the process quality monitoring module 2400 is configured to monitor paper web using infrared and other imaging devices suitable for capturing a heat map of the web in order to identify temperature distribution within a camera field of view. In some aspects, temperature of paper is inversely proportional to paper moisture, so the heat map may also provide information related to moisture distribution across the paper web. Full image heat mapping may enable the system to identify areas within a paper web that differ in temperature (e.g., from a mean value, from adjoining portions of the web, from an expected value in a certain portion of the production line, etc.).

As may be understood by one skilled in the art, paper mills may desire to provide paper within customer specifications. Often, mills are equipped with devices for measuring paper quality that allow operators to make process adjustments, remove portions of paper web that don't meet specifications, or reclassify paper that isn't up to certain standards (e.g., by modifying a rating of at least a portion of a paper web that does not meet at least one manufacturing requirement from a first classification level to a second, lower classification level). On-line and off-line devices may be configured to measure paper mechanical and chemical properties and to identify visible defects. Non-visible defects that are otherwise undetectable through these devices may also exist, however. As such, there is a need for improved techniques for identifying invisible (to the human eye) paper defects. In some aspects, the process quality monitoring module 2400 utilizes infrared cameras to capture, detect, and classify hot and cold spots in the paper web. These defects can then be classified based on their location in the web, temperature, etc.

At operation 2410, the process quality monitoring module 2400 captures paper web imaging data. In some aspects, the system may be configured to capture imaging data for one or more portions of a paper web along a paper manufacturing line. In some aspects, the imaging data may include any suitable imaging data such as one or more still images, video images, infrared images, visual images, etc. In a particular embodiment, the system is configured to capture infrared imaging data of a portion of a paper web for additional analysis by the system.

At operation 2420, the process quality monitoring module 2400 analyzes the imaging data to detect hot and/or cold spots. The system may, for example, identify particular portions of the paper web with temperature variations outside of a particular range (e.g., or within a particular range). In some aspects, and in any embodiment described herein, the system may identify streaks in addition to and/or in place of spots. It should be understood that any reference to identifying spots in the current application also should be understood to include streaks (e.g., which may include longer spots).

In some aspects, analyzing the imaging to detect hot and/or cold spots comprises analyzing the thermal imaging data to identify portions of an article of manufacture (e.g., metal, extruded metal, paper web, non-paper web, composite item, polymer object, plastic, etc.) that have a thermal property other than an expected thermal property for the material that makes up the article of manufacture.

For example, a particular material may have an expected set of thermal properties. In some aspects, certain portions of the material may include impurities that cause that portion of the material to deviate from the expected thermal properties. As an example, a particular metal (e.g., copper) may be extruded into metal tubing as part of a manufacturing process. The metal may have an expected thermal conductivity (e.g., measurable via IR imaging following extrusion while the pipe is still cooling). If certain portions of the pipe include one or more impurities (e.g., copper oxide), those portions may have a different temperature. As such, IR imaging can be used to identify temperature deviations in locations on an article of manufacturing that aren't necessarily 'hot' or 'cold' spots. Such spots may be spots with an other-than-expected temperature profile based on the material of the article. Such spots can then be classified (e.g., as defects) using any suitable technique described herein.

In still another example, IR imaging may be utilized to determine that a particular component of an article of manufacture has a temperature profile outside of an expected range. For example, particular manufacturing processes may require checks for contaminants (e.g., metal contaminants in a paper product). In such instances, infrared imaging may be utilized on an article of manufacture to identify contaminants (e.g., which may be considered defects) by their temperature profile (e.g., following a heating or cooling step in the manufacturing process). For example, metal contaminants may retain heat longer than surrounding materials (e.g., paper), enabling the system described herein to detect metal and other contaminants based on their thermal properties. This may, for example, eliminate additional processing steps used to identify those contaminants in traditional processes (e.g., with x-ray, metal detector, etc.).

At operation 2430, the process quality monitoring module 2400 classifies defects in the paper web based on an area, temperature, deviation, location, etc. of the detected hot and/or cold spots. The system may, for example, identify machine component (e.g., actuator) as a cause of a defect in a particular location. The system may use LWIR (long wave infrared) cameras to generate heat maps that represent paper web temperature distribution. Since paper temperature is proportional to paper moisture content temperature data can be used to generate a prediction as to whether a particular sheet may break (e.g., due to a wet spot). This is because the paper strength depends mainly on the inter-fiber bonding which, when disrupted by water immersion, may leave only about 2-3% of the dry tensile strength. As such, in various aspects, the system may be configured to generate a prediction that a sheet break is likely to originate at or near a wet spot even if the forces exerted by the paper machine are normal. The system is configured to process heat maps in substantially real time to detect areas of lower temperature and the system then classifies these areas by their location on the paper web, size, intensity (net difference in temperature) and gradient (the degree of change from normal temperature). The CD (cross direction) location of the weak spot is important since a weak spot can be tolerated inside of the paper web but not at the paper edges. The size is important because a larger spot has a higher probability of being subjected to destructive forces. The intensity is important since a lower temperature corresponds to a higher moisture content and thus lower tensile strength. The gradient is important since the paper is more likely to break near a high gradient point. Other parameters such as shape, edge uniformity, etc., can also be used to fully classify the weak spot.

At operation 2440, the process quality monitoring module 2400 tabulates the classified defects. The system may, for example, tabulate trends in defects in the form of defect maps. The system, in other aspects, may generate a reel map and/or web map indicating the location of an identified defect and trends in defects over time.

At operation 2450, the process quality monitoring module 2400 generates a user interface that provides an indication of the tabulated defect data. In some aspects, the defect maps can be used to trigger paper markers in order to enable an operator to reject certain portions of the paper web.

At operation 2460, the process quality monitoring module 2400 trains at least one of a machine learning model and/or a rule-based model using the defect data. In various aspects, the machine learning model may be trained using historical data on paper break events and associated data for each event (e.g., moisture, vibration, and other data) along with correlations to defect location, area, temperature, etc. Accordingly, the machine learning model may be configured using a variety of different types of supervised or unsupervised trained models such as, for example, support vector machine, naive Bayes, decision tree, neural network, and/or the like using the training data.

In some aspects, the training data may include an indication of a particular defect type in the paper web along with correlating factors that caused the identification of the defect type. For example, training data for a first classified defect may include: (1) temperature data for the paper web at the location of the defect; (2) temperature deviation data for the paper web at the location of the defect (e.g., a relative temperature when compared to nearby portions of the web); (3) area data for the defect (i.e., a location within the paper web at which the defect was identified based on the imaging data); and/or (4) any other supporting data related to the identification of the defect, its classification, etc. In this way, the machine learning model and/or rules-based model can use the training data to improve the accuracy of the model when predicating and/or identifying defects based on provided imaging data. In particular other aspects, the system may provide imaging data of a paper web to at least one of the machine-learning model and/or rules-based model to generate a prediction as to a future defect and/or to classify a particular defect based on parameters of the defect (i.e., temperature, variation, location, etc.).

In some aspects, the system may examine LWIR data for a finished paper web. In other aspects, the system may receive LWIR data from imaging devices positioned along the papermaking process to identify defects as they arise in the web (e.g., and provide better correlation data for identifying defect causes in the form of machine components that are causing defects). The system may, for example, include several LWIR cameras along the production line to identify weak sports as they occur. This may, for example, enable the system to enact some changes upstream of the defect's introduction to improve the process and reduce and/or eliminate defects.

For illustrative purposes, the process quality monitoring module 2400 is described with reference to implementations described above with respect to one or more examples described herein. Other implementations, however, are possible. In some aspects, the steps in FIG. 24 may be implemented in program code that is executed by one or more computing devices such as any suitable device or combination of devices described herein. In some aspects, one or more operations shown in FIG. 24 may be omitted or performed in a different order. Similarly, additional operations not shown in FIG. 24 may be performed.

Example System Architecture

Figure 25:
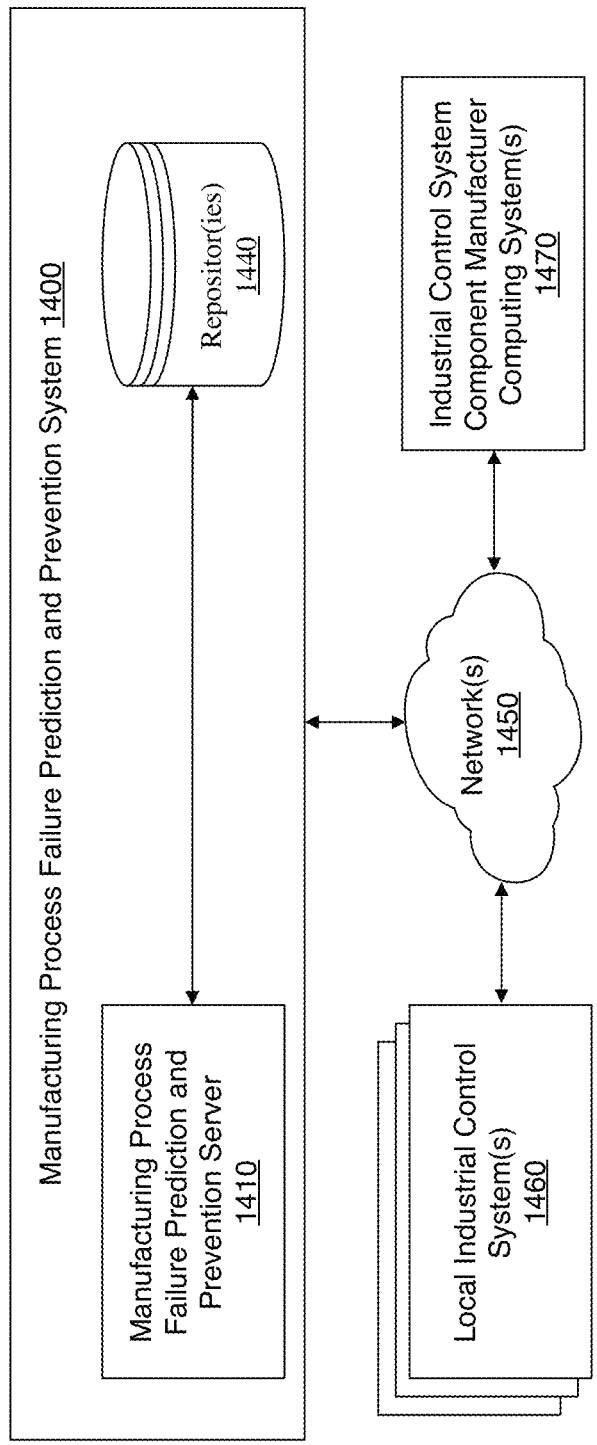
FIG. 25 depicts an example of a system architecture that may be used in accordance with various aspects of the present disclosure.

FIG. 25 is a block diagram of an example of a system architecture that can be used for generating a prediction as to a failure in a manufacturing process and generating (e.g., and facilitating implementation of) a preventative action to prevent the failure in various aspects as detailed herein. As may be understood from FIG. 18, the system architecture in some aspects may include a manufacturing process failure prediction and prevention system 1400 that comprises one or more manufacturing process failure prediction and prevention servers 1410 and a data repository 1440. The data repository 1440 may be made up of computing components such as servers, routers, data storage, networks, and/or the like that are used on the manufacturing process failure prediction and prevention system 1400 to store and manage data processed as part of the systems described herein.

As previously noted, the manufacturing process failure prediction and prevention system 1400 may provide functionality to one or more local industrial control system(s) 1460 and/or industrial control system component manufacturer computing system(s) 1470 that is available over one or more networks 150. Here, the local industrial control system(s) 1460 may access the functionality to generate a prediction of a failure event at a manufacturing plant operated by the local industrial control system 1460 based on current imaging, vibration and other data observed by the local industrial control system 1460.

Accordingly, the manufacturing process failure prediction and prevention servers 1410 may execute a set of modules as described herein. Furthermore, the manufacturing process failure prediction and prevention servers 1410 may provide one or more interfaces that allow the manufacturing process failure prediction and prevention system 1400 to communicate with the local industrial control system(s) 1460 and/or the industrial control system component manufacturer computing system(s) 1470 such as one or more suitable application programming interfaces (APIs), direct connections, and/or the like.

CONCLUSION

It should be understood that various aspects of the system architecture described above may be applicable to other types of system architectures, in general. While this specification contains many specific embodiment details, these should not be construed as limitations on the scope of any invention or of what may be claimed, but rather as descriptions of features that may be specific to particular embodiments of particular inventions. Certain features that are described in this specification in the context of separate embodiments may also be implemented in combination in a single embodiment. Conversely, various features that are described in the context of a single embodiment may also be implemented in multiple embodiments separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination.

Similarly, while operations may be described in a particular order, this should not be understood as requiring that such operations be performed in the particular order described or in sequential order, or that all described operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for the purposes of limitation.

What is claimed is:

1. A computer-implemented data processing method for identifying and classifying defects in a paper web produced by a manufacturing process, the method comprising:
receiving, by computing hardware, current thermal imaging data for a paper web;
analyzing, by the computing hardware, the thermal imaging data to identify a first portion of the paper web having a temperature that deviates from a surrounding portion of the paper web, the first portion comprising: at least one hot spot, at least one hot streak, at least one cold spot, or at least one cold streak on the paper web;
determining, by the computing hardware for the first portion of the paper web, a set of properties for the first portion of the paper web, the set of properties comprising
a cross-direction location of the first portion having the temperature deviation with respect to an edge of the paper web;
processing, by the computing hardware, the set of properties for the first portion of the paper web using at least one of a rules-based model, a machine-learning model, or a classification model to produce a defect classification for the first portion of the paper web;
generating, by the computing hardware based on the defect classification, a graphical user interface comprising defect map for the paper web, the defect map comprising at least the first portion of the paper web and a visual indication of the defect classification;
providing, by the computing hardware, the graphical user interface for display on a computing device; and
providing, by the computing hardware, the defect classification to at least one of a second machine-learning model or a second rules-based model to cause the second machine-learning model or the second rules-based model to generate a prediction as to an occurrence of a breakage event on the first portion of the paper web based on the defect classification.

2. The method of claim 1, further comprising:
receiving, by the computing hardware via the graphical user interface, feedback data related to the defect classification; and
responsive to receiving the feedback data, providing the feedback data as training data for one or more of the rules-based model, the machine-learning model, or the classification model.

3. The method of claim 1, further comprising:
determining, by the computing hardware based on the defect classification, a manufacturing risk for the manufacturing process;
identifying, by the computing hardware based on the manufacturing risk, a corrective action to take in response to the manufacturing risk; and
performing, by the computing hardware, at least a portion of the corrective action.

4. The method of claim 1, further comprising:
analyzing, by the computing hardware, the thermal imaging data to identify a second portion of the paper web having a second temperature that deviates from the surrounding portion of the paper web;
determining, by the computing hardware for the second portion of the paper web, a second set of properties for the second portion of the paper web, the second set of properties comprising one or more of:
second location data for the second portion of the paper web;
a second temperature of the second portion;
a second shape of the second portion of the paper web;
a second edge uniformity of the second portion of the paper web; or
a second temperature deviation of the second portion with respect to the surrounding portion of the paper web;
processing, by the computing hardware, the second set of properties for the second portion of the paper web using at least one of the rules-based model, the machine-learning model, or the classification model to produce a second defect classification for the second portion of the paper web; and
providing, by the computing hardware, an indication of the second defect classification on a computing device.

5. A system comprising:
a non-transitory computer-readable medium storing instructions; and
a processing device communicatively coupled to the non-transitory computer-readable medium, wherein the processing device is configured to execute the instructions and thereby perform operations comprising:
determining temperature data for at least part of an article of manufacture in a manufacturing process;
analyzing the temperature data to identify a first portion of the article of manufacture having a temperature that deviates from a surrounding portion of the first portion, the first portion comprising: at least one hot spot, at least one hot streak, at least one cold spot, or at least one cold streak on the article of manufacture;

determining, for the first portion of the article of manufacture, a set of properties comprising one or more of:
 a temperature of the first portion of the article of manufacture; or
 a material type of the article of manufacture;

processing the set of properties for the first portion of the article of manufacture using at least one of a rules-based model, a machine-learning model, or a classification model to produce a defect classification for the first portion of the article of manufacture, the defect classification comprising an identification of a contaminant in the article of manufacture having a thermal property that differs from a thermal property of the article of manufacture; and providing an indication of the defect classification for display on a computing device; and providing the defect classification to at least one of a second machine-learning model or a second rules-based model to cause the second machine-learning model or the second rules-based model to generate a prediction as to an occurrence of a breakage event on the first portion of the article of manufacture based on the defect classification.

6. The system of claim 5, wherein the article of manufacture comprises at least one of:
 a paper web;
 a non-paper web; or
 an extruded material.

7. The system of claim 5, wherein analyzing the temperature data to identify the first portion of the article of manufacture having a temperature that deviates from a surrounding portion of the first portion comprises:
 determining an expected temperature profile for the article of manufacture based on the material type of the article of manufacture; and
 identifying the first portion of the article of manufacture having the temperature that deviates from the surrounding portion of the first portion comprises identifying the first portion as an impurity that has a temperature other than the expected temperature.

8. The system of claim 5, wherein determining the temperature data for the at least part of the article of manufacture in the manufacturing process comprises determining the temperature at at least one of:
 during the manufacturing process; or
 substantially immediately following the manufacturing process.

9. A computer-implemented data processing method for identifying and classifying potential defects in an article of manufacture, the method comprising:
 determining temperature data from thermal imaging data for at least part of an article of manufacture in a manufacturing process;
 analyzing, by computing hardware, the temperature data to identify a first portion of the article of manufacture having a temperature that deviates from an expected temperature;
 determining, by the computing hardware for the first portion of the article of manufacture, a set of properties for the first portion of the article of manufacture, the set of properties comprising one or more of:
  location data for the first portion of the article of manufacture with respect to the article of manufacture;
  an absolute temperature of the article of manufacture;
  a shape of the first portion of the article of manufacture; or
  a temperature deviation of the first portion with respect to the expected temperature;

processing, by the computing hardware, the set of properties for the first portion of the article of manufacture using at least one of a rules-based model, a machine-learning model, or a classification model to produce a defect classification for the first portion of the article of manufacture;

providing, by the computing hardware, an indication of the defect classification for display on a computing device;

providing, by the computing hardware, the defect classification to at least one of a second machine-learning model or a second rules-based model to cause the second machine-learning model or the second rules-based model to generate a prediction as to an occurrence of a breakage event on the first portion of the article of manufacture based on the defect classification.

10. The method of claim 9, wherein:
the expected temperature is determined based on one or more material properties of the article of manufacture; and
processing the set of properties for the first portion of the article of manufacture using at least one of the rules-based model, the machine-learning model, or the classification model to produce the defect classification for the first portion of the article of manufacture further comprises processing the one or more material properties of the article of manufacture with the set of properties to produce the defect classification for the first portion of the article of manufacture.

11. The method of claim 9, wherein the article of manufacture comprises at least one of:
 a paper web;
 a non-paper web;
 an extruded material;
 a polymer; or
 a metal.

12. The method of claim 9, wherein:
 the defect classification includes an indication of a defect concern level;
 the method further comprises:
  determining, by the computing hardware, an action based on the defect concern level; and
  causing, by the computing hardware, performance of the action.

13. The method of claim 12, wherein the action comprises reclassifying at least a portion of the article of manufacture from a first type of classification to a second type of classification.

14. The method of claim 12, further comprising:
 identifying additional portions of the article of manufacture having respective temperatures that deviate from the expected temperature over time; and
 generating a graphical user interface comprising a defect map comprising a representation of the article of manufacture and an indication of a respective location of each of the additional portions of the article of manufacture.

15. The method of claim 14, wherein the indication of the defect classification comprises a trend in defects over time determined based on the identified additional portions of the article of manufacture having the respective temperatures that deviate from the expected temperature over time.

16. The method of claim 9, wherein the set of properties comprise the location data for the first portion of the article of manufacture with respect to the article of manufacture, the shape of the first portion of the article of manufacture, and the temperature deviation of the first portion with respect to the expected temperature.

17. The method of claim 9, further comprising:
determining, by the computing hardware, second temperature data from second thermal imaging data for the first portion of the article of manufacture in the manufacturing process; and
analyzing, by the computing hardware, the second temperature data and the defect classification to determine a defect origin for the first portion of the article of manufacture in the manufacturing process.

18. The method of claim 1, further comprising:
responsive to the prediction of the occurrence of the breakage event, facilitating performance of a preventative action, wherein the preventative action comprises at least one of:
modifying an operating parameter of at least one machine component used in the manufacturing process;
activating a cleaning component for manufacturing process;
activating a siren;
generating an alert and transmitting the alert to a computing device; or
at least temporarily ceasing the manufacturing process.

19. The method of claim 18, further comprising processing the prediction and historical preventative action success data using at least one of a third rules-based model or a third machine-learning model to select the preventative action.

* * * * *